United States Patent
Low et al.

(10) Patent No.: US 12,150,981 B2
(45) Date of Patent: Nov. 26, 2024

(54) CHIMERIC ANTIGEN RECEPTOR-EXPRESSING T CELLS AS ANTI-CANCER THERAPEUTICS

(71) Applicant: Purdue Research Foundation, West Lafayette, IN (US)

(72) Inventors: Philip S. Low, West Lafayette, IN (US); Haiyan Chu, West Lafayette, IN (US); Yong Gu Lee, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 491 days.

(21) Appl. No.: 17/387,892

(22) Filed: Jul. 28, 2021

(65) Prior Publication Data

US 2022/0000996 A1    Jan. 6, 2022

Related U.S. Application Data

(63) Continuation of application No. 15/296,666, filed on Oct. 18, 2016, now abandoned, which is a continuation of application No. 14/654,227, filed as application No. PCT/US2013/076986 on Dec. 20, 2013, now abandoned.

(60) Provisional application No. 61/740,384, filed on Dec. 20, 2012.

(51) Int. Cl.
| | |
|---|---|
| A61K 47/54 | (2017.01) |
| A61K 35/17 | (2015.01) |
| A61K 39/00 | (2006.01) |
| A61K 47/55 | (2017.01) |
| A61K 47/60 | (2017.01) |
| A61K 47/69 | (2017.01) |

(52) U.S. Cl.
CPC .......... *A61K 39/0013* (2013.01); *A61K 35/17* (2013.01); *A61K 47/545* (2017.08); *A61K 47/551* (2017.08); *A61K 47/555* (2017.08); *A61K 47/60* (2017.08); *A61K 47/6901* (2017.08); *A61K 2039/5156* (2013.01); *A61K 2039/5158* (2013.01); *A61K 2039/585* (2013.01)

(58) Field of Classification Search
None
See application file for complete search history.

(56) References Cited

U.S. PATENT DOCUMENTS

| | | |
|---|---|---|
| 4,690,915 A | 9/1987 | Rosenbera |
| 4,946,778 A | 8/1990 | Ladner et al. |
| 5,087,616 A | 2/1992 | Myers et al. |
| 5,116,964 A | 5/1992 | Capon et al. |
| 5,202,238 A | 4/1993 | Fell, Jr. et al. |
| 5,216,132 A | 6/1993 | Basi |
| 5,359,046 A | 10/1994 | Capon et al. |
| 5,372,930 A | 12/1994 | Colton et al. |
| 5,482,856 A | 1/1996 | Fell, Jr. et al. |
| 5,514,582 A | 5/1996 | Capon et al. |
| 5,525,503 A | 6/1996 | Rudd et al. |
| 5,538,866 A | 7/1996 | Israeli et al. |
| 5,670,148 A | 9/1997 | Sherwin et al. |
| 5,686,281 A | 11/1997 | Roberts |
| 5,712,149 A | 1/1998 | Roberts |
| 5,714,147 A | 2/1998 | Capon et al. |
| 5,741,899 A | 4/1998 | Capon et al. |
| 5,747,292 A | 5/1998 | Greenberg et al. |
| 5,830,755 A | 11/1998 | Nishimura et al. |
| 5,834,256 A | 11/1998 | Finer et al. |
| 5,837,544 A | 11/1998 | Capon et al. |
| 5,843,728 A | 12/1998 | Seed et al. |
| 5,851,828 A | 12/1998 | Seed et al. |
| 5,858,740 A | 1/1999 | Finer et al. |
| 5,861,156 A | 1/1999 | George et al. |
| 5,906,936 A | 5/1999 | Eshhar et al. |
| 5,908,638 A | 6/1999 | Huber et al. |
| 5,912,170 A | 6/1999 | Seed et al. |
| 5,912,172 A | 6/1999 | Eshhar et al. |
| 5,914,109 A | 6/1999 | Zolla-Pazner et al. |
| 5,935,818 A | 8/1999 | Israeli et al. |
| 5,969,102 A | 10/1999 | Bram et al. |
| 6,004,781 A | 12/1999 | Seed |
| 6,004,811 A | 12/1999 | Seed et al. |
| 6,077,947 A | 6/2000 | Capon et al. |
| 6,083,751 A | 7/2000 | Feldhaus et al. |
| 6,103,521 A | 8/2000 | Capon et al. |
| 6,117,656 A | 9/2000 | Seed |
| 6,132,718 A | 10/2000 | Hansen et al. |
| 6,218,187 B1 | 4/2001 | Finer et al. |
| 6,261,787 B1 | 7/2001 | Davis et al. |
| 6,319,494 B1 | 11/2001 | Capon et al. |
| 6,392,013 B1 | 5/2002 | Seed et al. |

(Continued)

FOREIGN PATENT DOCUMENTS

| | | |
|---|---|---|
| CN | 102775500 | 11/2012 |
| CN | 106132436 A | 11/2016 |

(Continued)

OTHER PUBLICATIONS

Altschul et al., Basic Local Alignment Search Tool, Journal of molecular biology, Oct. 1990, pp. 403-410.

(Continued)

*Primary Examiner* — Michael D Burkhart

(74) *Attorney, Agent, or Firm* — Schwegman Lundberg & Woessner, P.A.

(57) ABSTRACT

Cytotoxic lymphocytes expressing chimeric antigen receptors (CAR) that target and bind small conjugate molecules (SCM) are disclosed, as well as methods of using the cells and the SCMs in the treatment of cancer.

31 Claims, 12 Drawing Sheets

Specification includes a Sequence Listing.

(56) References Cited

U.S. PATENT DOCUMENTS

| | | |
|---|---|---|
| 6,406,697 B1 | 6/2002 | Capon et al. |
| 6,407,221 B1 | 6/2002 | Capon et al. |
| 6,410,014 B1 | 6/2002 | Seed et al. |
| 6,410,319 B1 | 6/2002 | Raubitschek et al. |
| 6,432,403 B1 | 8/2002 | Philips |
| 6,451,995 B1 | 9/2002 | Cheuna et al. |
| 6,521,602 B1 | 2/2003 | Patel et al. |
| 6,524,572 B1 | 2/2003 | Li |
| 6,699,972 B1 | 3/2004 | Roffler et al. |
| 6,753,162 B1 | 6/2004 | Seed et al. |
| 6,759,243 B2 | 7/2004 | Kranz et al. |
| 6,770,749 B2 | 8/2004 | Ellenhorn et al. |
| 6,953,668 B1 | 10/2005 | Israeli et al. |
| 7,037,647 B1 | 5/2006 | Israeli et al. |
| 7,049,136 B2 | 5/2006 | Seed et al. |
| 7,052,906 B1 | 5/2006 | Lawson et al. |
| 7,070,995 B2 | 7/2006 | Jensen |
| 7,105,159 B1 | 9/2006 | Israeli et al. |
| 7,217,421 B1 | 5/2007 | McArthur et al. |
| 7,265,209 B2 | 9/2007 | Jensen |
| 7,320,787 B2 | 1/2008 | Seed et al. |
| 7,348,004 B2 | 3/2008 | Peters et al. |
| 7,354,587 B1 | 4/2008 | Hansen |
| 7,354,762 B2 | 4/2008 | Jensen |
| 7,381,408 B2 | 6/2008 | Mezo et al. |
| 7,404,956 B2 | 7/2008 | Peters et al. |
| 7,435,596 B2 | 10/2008 | Campana et al. |
| 7,446,179 B2 | 11/2008 | Jensen et al. |
| 7,446,190 B2 | 11/2008 | Sadelain et al. |
| 7,446,191 B2 | 11/2008 | Jensen |
| 7,482,005 B2 | 1/2009 | Kim |
| 7,514,537 B2 | 4/2009 | Jensen |
| 7,569,663 B2 | 8/2009 | Tykocinski et al. |
| 7,572,891 B2 | 8/2009 | Belldegrun et al. |
| 7,618,817 B2 | 11/2009 | Campbell |
| 7,632,497 B2 | 12/2009 | Stavenhagen |
| 7,655,461 B2 | 2/2010 | Finn et al. |
| 7,666,424 B2 | 2/2010 | Cheung et al. |
| 7,723,111 B2 | 5/2010 | Hwu et al. |
| 7,741,465 B1 | 6/2010 | Eshhar et al. |
| 7,871,817 B2 | 1/2011 | Voss et al. |
| 7,906,620 B2 | 3/2011 | Eisenbach et al. |
| 7,919,079 B2 | 4/2011 | Simmons et al. |
| 7,939,059 B2 | 5/2011 | Yang et al. |
| 7,994,298 B2 | 8/2011 | Zhang et al. |
| 7,998,736 B2 | 8/2011 | Morgan et al. |
| 8,105,830 B2 | 1/2012 | Weidanz et al. |
| 8,148,154 B2 | 4/2012 | Cheung et al. |
| 8,163,887 B2 | 4/2012 | Hansen |
| 8,211,422 B2 | 7/2012 | Eshhar et al. |
| RE43,586 E | 8/2012 | Israeli et al. |
| 8,252,914 B2 | 8/2012 | Zhang et al. |
| 8,324,353 B2 | 12/2012 | Jensen |
| 8,388,972 B2 | 3/2013 | Martin et al. |
| 8,389,282 B2 | 3/2013 | Sadelain et al. |
| 8,399,645 B2 | 3/2013 | Campana et al. |
| 8,409,577 B2 | 4/2013 | Thompson et al. |
| 8,450,112 B2 | 5/2013 | Li et al. |
| 8,465,743 B2 | 6/2013 | Rosenberg et al. |
| 8,486,911 B2 | 7/2013 | Okada et al. |
| 8,497,118 B2 | 7/2013 | Jensen |
| 8,741,306 B2 | 6/2014 | Belldegrun et al. |
| 8,802,374 B2 | 8/2014 | Jensen |
| 8,809,050 B2 | 8/2014 | Vera et al. |
| 8,822,196 B2 | 9/2014 | Rosenberg et al. |
| 8,822,647 B2 | 9/2014 | Jensen |
| 8,859,229 B2 | 10/2014 | Rabinovich et al. |
| 8,877,199 B2 | 11/2014 | Rader et al. |
| 8,906,682 B2 | 12/2014 | June et al. |
| 8,911,993 B2 | 12/2014 | June et al. |
| 8,932,830 B2 | 1/2015 | Peters et al. |
| 8,946,385 B2 | 2/2015 | Kawai |
| 8,956,860 B2 | 2/2015 | Vera et al. |
| 9,023,621 B2 | 5/2015 | Gurney et al. |
| 9,040,669 B2 | 5/2015 | Cheung et al. |
| 9,062,127 B2 | 6/2015 | Voss et al. |
| 9,074,000 B2 | 7/2015 | Scheinberg et al. |
| 9,089,520 B2 | 7/2015 | Brenner |
| 9,101,584 B2 | 8/2015 | June et al. |
| 9,101,609 B2 | 8/2015 | Tan et al. |
| 9,102,760 B2 | 8/2015 | June et al. |
| 9,102,761 B2 | 8/2015 | June et al. |
| 9,111,061 B2 | 8/2015 | Otsuka et al. |
| 9,133,436 B2 | 9/2015 | Riley et al. |
| 9,156,915 B2 | 10/2015 | Waldman et al. |
| 9,163,258 B2 | 10/2015 | Riddell et al. |
| 9,175,308 B2 | 11/2015 | Shiku et al. |
| 9,181,527 B2 | 11/2015 | Sentman et al. |
| 9,211,321 B2 | 12/2015 | Karlsson-Parra et al. |
| 9,212,229 B2 | 12/2015 | Schonfeld et al. |
| 9,220,728 B2 | 12/2015 | Sadelain et al. |
| 9,226,936 B2 | 1/2016 | Hu et al. |
| 9,233,125 B2 | 1/2016 | Davila et al. |
| 9,242,014 B2 | 1/2016 | Kipps et al. |
| 9,266,960 B2 | 2/2016 | Morgan et al. |
| 9,272,002 B2 | 3/2016 | Powell, Jr. et al. |
| 9,273,283 B2 | 3/2016 | Sentman |
| 9,279,008 B2 | 3/2016 | Scholler et al. |
| 9,334,330 B2 | 5/2016 | Birkle et al. |
| 9,345,748 B2 | 5/2016 | Morgan et al. |
| 9,352,036 B2 | 5/2016 | McBride et al. |
| 9,359,447 B2 | 6/2016 | Feldman et al. |
| 9,365,641 B2 | 6/2016 | June et al. |
| 9,393,268 B2 | 7/2016 | Waldman et al. |
| 9,393,292 B2 | 7/2016 | Brenner |
| 9,394,364 B2 | 7/2016 | Ho et al. |
| 9,394,368 B2 | 7/2016 | Brogdon et al. |
| 9,402,865 B2 | 8/2016 | Powell et al. |
| 9,402,888 B2 | 8/2016 | Hildegund et al. |
| 9,408,904 B2 | 8/2016 | Wright et al. |
| 9,409,992 B2 | 8/2016 | Ho et al. |
| 9,409,994 B2 | 8/2016 | Ho et al. |
| 9,416,190 B2 | 8/2016 | Ho et al. |
| 9,422,351 B2 | 8/2016 | Scholler et al. |
| 9,434,935 B2 | 9/2016 | Spencer et al. |
| 9,446,105 B2 | 9/2016 | Powell et al. |
| 9,447,194 B2 | 9/2016 | Jensen |
| 9,453,075 B2 | 9/2016 | Cheung et al. |
| 9,464,140 B2 | 10/2016 | June et al. |
| 9,469,684 B2 | 10/2016 | Finn et al. |
| 9,476,028 B2 | 10/2016 | Karlsson-Parra et al. |
| 9,481,728 B2 | 11/2016 | June et al. |
| 9,487,800 B2 | 11/2016 | Schonfeld et al. |
| 9,492,499 B2 | 11/2016 | Jaynes et al. |
| 9,492,529 B2 | 11/2016 | Karlsson-Parra et al. |
| 9,493,740 B2 | 11/2016 | Brenner et al. |
| 9,499,629 B2 | 11/2016 | June et al. |
| 9,499,855 B2 | 11/2016 | Hyde et al. |
| 9,511,092 B2 | 12/2016 | Campana et al. |
| 9,518,123 B2 | 12/2016 | June et al. |
| 9,522,955 B2 | 12/2016 | Rosenberg et al. |
| 9,540,445 B2 | 1/2017 | June et al. |
| 9,540,448 B2 | 1/2017 | Scheinberg et al. |
| 9,561,291 B2 | 2/2017 | Kovesdi et al. |
| 9,562,087 B2 | 2/2017 | Ring et al. |
| 9,567,399 B1 | 2/2017 | Campbell et al. |
| 9,572,836 B2 | 2/2017 | June et al. |
| 9,572,837 B2 | 2/2017 | Wu |
| 9,573,988 B2 | 2/2017 | Brogdon et al. |
| 9,574,014 B2 | 2/2017 | Williams et al. |
| 9,587,020 B2 | 3/2017 | Wu et al. |
| 9,587,237 B2 | 3/2017 | Hyde et al. |
| 9,597,357 B2 | 3/2017 | Gregory et al. |
| 9,605,049 B2 | 3/2017 | Campana |
| 9,623,049 B2 | 4/2017 | Eshhar et al. |
| 9,624,292 B2 | 4/2017 | Voss et al. |
| 9,624,306 B2 | 4/2017 | Morgan et al. |
| 9,629,877 B2 | 4/2017 | Cooper et al. |
| 9,636,388 B2 | 5/2017 | Lawman et al. |
| 9,636,416 B2 | 5/2017 | Peters et al. |
| 9,642,906 B2 | 5/2017 | Ramos et al. |
| 9,650,428 B2 | 5/2017 | Sampath et al. |
| 9,657,105 B2 | 5/2017 | Forman et al. |
| 9,662,405 B2 | 5/2017 | Waldman et al. |

(56) References Cited

U.S. PATENT DOCUMENTS

| | | |
|---|---|---|
| 9,663,756 B1 | 5/2017 | Lipkens et al. |
| 9,663,763 B2 | 5/2017 | Sentman |
| 9,669,058 B2 | 6/2017 | Li et al. |
| 9,670,281 B2 | 6/2017 | Lim et al. |
| 9,676,867 B2 | 6/2017 | Marasco et al. |
| 9,688,740 B2 | 6/2017 | Choi et al. |
| 9,688,760 B2 | 6/2017 | Kufer et al. |
| 9,694,033 B2 | 7/2017 | Yi et al. |
| 9,701,758 B2 | 7/2017 | Cooper et al. |
| 9,708,384 B2 | 7/2017 | Scholler et al. |
| 9,714,278 B2 | 7/2017 | June et al. |
| 9,717,745 B2 | 8/2017 | He |
| 9,725,519 B2 | 8/2017 | Masuko et al. |
| 9,733,245 B2 | 8/2017 | Kawai |
| 9,738,726 B2 | 8/2017 | Dimitrov et al. |
| 9,745,368 B2 | 8/2017 | Milone et al. |
| 9,765,142 B2 | 9/2017 | Dimitrov et al. |
| 9,765,156 B2 | 9/2017 | June et al. |
| 9,765,330 B1 | 9/2017 | Niazi et al. |
| 9,765,342 B2 | 9/2017 | Kochenderfer |
| 9,777,061 B2 | 10/2017 | Ebersbach et al. |
| 9,777,064 B2 | 10/2017 | Wang et al. |
| 9,783,591 B2 | 10/2017 | June et al. |
| 9,789,174 B2 | 10/2017 | Karlsson-Parra et al. |
| 9,790,267 B2 | 10/2017 | Kaplan |
| 9,790,278 B2 | 10/2017 | Sentman et al. |
| 9,790,282 B2 | 10/2017 | Orentas et al. |
| 9,790,467 B2 | 10/2017 | Kevlahan et al. |
| 9,796,783 B2 | 10/2017 | Agerstam et al. |
| 9,802,997 B2 | 10/2017 | Mahr et al. |
| 9,803,022 B2 | 10/2017 | Ho et al. |
| 9,808,486 B2 | 11/2017 | Georgiou et al. |
| 9,809,581 B2 | 11/2017 | Chen et al. |
| 9,815,901 B2 | 11/2017 | Brogdon et al. |
| 9,815,908 B2 | 11/2017 | Schonfeld et al. |
| 9,821,011 B1 | 11/2017 | Sentman |
| 9,821,012 B2 | 11/2017 | Wu et al. |
| 9,822,340 B1 | 11/2017 | Sentman |
| 9,828,399 B2 | 11/2017 | Tremblay et al. |
| 9,828,435 B2 | 11/2017 | Evans et al. |
| 9,833,476 B2 | 12/2017 | Zhang et al. |
| 9,833,480 B2 | 12/2017 | Junghans et al. |
| 9,834,545 B2 | 12/2017 | Chen et al. |
| 9,834,590 B2 | 12/2017 | Campana et al. |
| 9,840,548 B2 | 12/2017 | Mahr et al. |
| 9,845,362 B2 | 12/2017 | Mukherjee |
| 9,849,092 B2 | 12/2017 | Peyman |
| 9,855,297 B2 | 1/2018 | Duchateau et al. |
| 9,855,298 B2 | 1/2018 | Bot et al. |
| 9,856,322 B2 | 1/2018 | Campana et al. |
| 9,856,497 B2 | 1/2018 | Qi et al. |
| 9,856,501 B2 | 1/2018 | O'Keefe et al. |
| 9,862,756 B2 | 1/2018 | Mahr et al. |
| 9,862,775 B2 | 1/2018 | Kwon et al. |
| 9,868,774 B2 | 1/2018 | Orentas et al. |
| 9,868,951 B2 | 1/2018 | Hu et al. |
| 9,873,894 B2 | 1/2018 | Conway et al. |
| 9,879,087 B2 | 1/2018 | DeSander et al. |
| 9,885,021 B2 | 2/2018 | Bollard et al. |
| 9,889,160 B2 | 2/2018 | Jantz et al. |
| 9,889,161 B2 | 2/2018 | Jantz et al. |
| 9,890,393 B2 | 2/2018 | Duchateau et al. |
| 9,914,909 B2 | 3/2018 | Brown et al. |
| 10,117,897 B2 | 11/2018 | Sadelain et al. |
| 11,311,576 B2 | 4/2022 | Jensen et al. |
| 11,759,480 B2 | 9/2023 | Low et al. |
| 11,779,602 B2 | 10/2023 | Low et al. |
| 11,850,262 B2 | 12/2023 | Low et al. |
| 2001/0031252 A1 | 10/2001 | Low et al. |
| 2002/0004052 A1 | 1/2002 | Berd et al. |
| 2002/0018783 A1 | 2/2002 | Sadelain et al. |
| 2002/0111474 A1 | 8/2002 | Capon et al. |
| 2002/0132983 A1 | 9/2002 | Junghans et al. |
| 2003/0077249 A1 | 4/2003 | Bebbington et al. |
| 2003/0170238 A1 | 9/2003 | Gruenberg et al. |
| 2003/0171546 A1 | 9/2003 | Jensen et al. |
| 2003/0175288 A1 | 9/2003 | Itoh |
| 2003/0215427 A1 | 11/2003 | Jensen |
| 2004/0043401 A1 | 3/2004 | Sadelain et al. |
| 2005/0113564 A1 | 5/2005 | Campana et al. |
| 2005/0129671 A1 | 6/2005 | Cooper et al. |
| 2006/0018878 A1 | 1/2006 | Cooper et al. |
| 2006/0067920 A1 | 3/2006 | Jensen et al. |
| 2006/0155115 A1 | 7/2006 | Jakobsen et al. |
| 2007/0031438 A1 | 2/2007 | Junghans et al. |
| 2007/0036773 A1 | 2/2007 | Cooper et al. |
| 2008/0051380 A1 | 2/2008 | Auerbach et al. |
| 2008/0188000 A1 | 8/2008 | Reik et al. |
| 2009/0011984 A1 | 1/2009 | Yla-Herttuala et al. |
| 2009/0191172 A1 | 7/2009 | Cooper et al. |
| 2009/0202501 A1 | 8/2009 | Zhang et al. |
| 2009/0257994 A1 | 10/2009 | Jensen |
| 2009/0324630 A1 | 12/2009 | Jensen |
| 2010/0135974 A1 | 6/2010 | Eshhar et al. |
| 2010/0178276 A1 | 7/2010 | Sadelain et al. |
| 2010/0278830 A1 | 11/2010 | Shoemaker et al. |
| 2011/0172254 A1 | 7/2011 | Leamon et al. |
| 2011/0178279 A1 | 7/2011 | Williams et al. |
| 2012/0093842 A1 | 4/2012 | Eshhar et al. |
| 2012/0213783 A1 | 8/2012 | Rosenberg et al. |
| 2012/0302466 A1 | 11/2012 | Sentman |
| 2013/0058936 A1 | 3/2013 | Bruenker et al. |
| 2013/0143895 A1 | 6/2013 | McAllister et al. |
| 2013/0149337 A1 | 6/2013 | Cooper et al. |
| 2013/0156794 A1 | 6/2013 | Eshhar et al. |
| 2013/0287748 A1 | 10/2013 | June et al. |
| 2013/0287752 A1 | 10/2013 | Davila et al. |
| 2013/0302466 A1 | 11/2013 | Joerg |
| 2013/0309267 A1 | 11/2013 | Simmons et al. |
| 2013/0309258 A1 | 12/2013 | June et al. |
| 2013/0323834 A1 | 12/2013 | Brenner |
| 2013/0344066 A1 | 12/2013 | Faham et al. |
| 2014/0004132 A1 | 1/2014 | Brenner et al. |
| 2014/0004137 A1 | 1/2014 | Ovaa et al. |
| 2014/0017170 A1 | 1/2014 | Irvine et al. |
| 2014/0050708 A1 | 2/2014 | Powell et al. |
| 2014/0099309 A1 | 4/2014 | Powell et al. |
| 2014/0120136 A1 | 5/2014 | Katsikis et al. |
| 2014/0134142 A1 | 5/2014 | Smith et al. |
| 2014/0134720 A1 | 5/2014 | Stauss et al. |
| 2014/0227237 A1 | 8/2014 | June et al. |
| 2014/0234348 A1 | 8/2014 | Scholler et al. |
| 2014/0255363 A1 | 9/2014 | Metelitsa et al. |
| 2014/0271582 A1 | 9/2014 | Forman et al. |
| 2014/0271635 A1 | 9/2014 | Brogdon et al. |
| 2014/0274909 A1 | 9/2014 | Orentas et al. |
| 2014/0286973 A1 | 9/2014 | Powell |
| 2014/0286987 A1 | 9/2014 | Spencer et al. |
| 2014/0294861 A1 | 10/2014 | Scholler et al. |
| 2014/0301993 A1 | 10/2014 | Powell et al. |
| 2014/0308259 A1 | 10/2014 | Scholler et al. |
| 2014/0322183 A1 | 10/2014 | Milone et al. |
| 2014/0322212 A1 | 10/2014 | Brogdon et al. |
| 2014/0322275 A1 | 10/2014 | Brogdon et al. |
| 2014/0356398 A1 | 12/2014 | Riddell et al. |
| 2014/0378389 A1 | 12/2014 | Robbins et al. |
| 2015/0073154 A1 | 3/2015 | Davis |
| 2015/0110760 A1 | 4/2015 | Zhang et al. |
| 2015/0139943 A1 | 5/2015 | Campana et al. |
| 2015/0152181 A1 | 6/2015 | Sentman et al. |
| 2015/0211023 A1 | 7/2015 | Shiboleth et al. |
| 2015/0225470 A1 | 8/2015 | Zhang et al. |
| 2015/0225480 A1 | 8/2015 | Powell et al. |
| 2015/0238631 A1 | 8/2015 | Kim et al. |
| 2015/0283178 A1 | 10/2015 | June et al. |
| 2015/0306141 A1 | 10/2015 | Jensen et al. |
| 2015/0307564 A1 | 10/2015 | Young et al. |
| 2015/0307842 A1 | 10/2015 | Sentman |
| 2015/0320799 A1 | 11/2015 | Low et al. |
| 2015/0328292 A1 | 11/2015 | Spencer et al. |
| 2015/0368342 A1 | 12/2015 | Wu et al. |
| 2016/0008398 A1 | 1/2016 | Sadelain et al. |
| 2016/0046700 A1 | 2/2016 | Foster et al. |
| 2016/0046724 A1 | 2/2016 | Brogdon et al. |

(56) References Cited

U.S. PATENT DOCUMENTS

| | | |
|---|---|---|
| 2016/0046729 A1 | 2/2016 | Schonfeld et al. |
| 2016/0051651 A1 | 2/2016 | Brogdon et al. |
| 2016/0058857 A1 | 3/2016 | Spencer et al. |
| 2016/0068601 A1 | 3/2016 | Brogdon et al. |
| 2016/0076056 A1 | 3/2016 | Reik et al. |
| 2016/0096892 A1 | 4/2016 | Brogdon et al. |
| 2016/0120907 A1 | 5/2016 | Sentman |
| 2016/0129109 A1 | 5/2016 | Davila et al. |
| 2016/0151465 A1 | 6/2016 | Slawin et al. |
| 2016/0166613 A1 | 6/2016 | Spencer et al. |
| 2016/0175359 A1 | 6/2016 | Spencer et al. |
| 2016/0185861 A1 | 6/2016 | Bedoya et al. |
| 2016/0222119 A1 | 8/2016 | Scholler et al. |
| 2016/0243258 A1 | 8/2016 | Scharenberq et al. |
| 2016/0250258 A1 | 9/2016 | Delaney et al. |
| 2016/0340649 A1 | 11/2016 | Brown et al. |
| 2016/0361360 A1 | 12/2016 | Chang et al. |
| 2017/0002017 A1 | 1/2017 | Andrez et al. |
| 2017/0015746 A1 | 1/2017 | Jensen |
| 2017/0029531 A1 | 2/2017 | Crane |
| 2017/0029774 A1 | 2/2017 | Jensen et al. |
| 2017/0044240 A1 | 2/2017 | Waqner et al. |
| 2017/0081411 A1 | 3/2017 | Engels et al. |
| 2017/0087185 A1 | 3/2017 | Crane et al. |
| 2017/0152297 A1 | 6/2017 | Jensen et al. |
| 2017/0166877 A1 | 6/2017 | Bayle et al. |
| 2017/0209543 A9 | 7/2017 | Jensen et al. |
| 2017/0224733 A1 | 8/2017 | Badie et al. |
| 2017/0267742 A1 | 9/2017 | Jensen et al. |
| 2017/0306303 A1 | 10/2017 | Taunton et al. |
| 2017/0340672 A1 | 11/2017 | Wu et al. |
| 2017/0342124 A1 | 11/2017 | Scholler et al. |
| 2017/0356010 A1 | 12/2017 | Frost et al. |
| 2017/0360910 A1 | 12/2017 | Wanq et al. |
| 2017/0368098 A1 | 12/2017 | Chen et al. |
| 2018/0009891 A1 | 1/2018 | Jensen |
| 2018/0016539 A1 | 1/2018 | Dinq et al. |
| 2018/0022795 A1 | 1/2018 | Milone et al. |
| 2018/0022828 A1 | 1/2018 | Schonfeld et al. |
| 2018/0142198 A1 | 5/2018 | Sharei et al. |
| 2018/0142239 A1 | 5/2018 | Yu et al. |
| 2018/0214527 A1 | 8/2018 | Want et al. |
| 2018/0282692 A1 | 10/2018 | Rawlinqs et al. |
| 2018/0320133 A1 | 11/2018 | Forman et al. |
| 2018/0327781 A1 | 11/2018 | Scharenberq et al. |
| 2019/0000881 A1 | 1/2019 | Sadelain et al. |
| 2019/0016776 A1 | 1/2019 | Jensen |
| 2019/0091308 A1 | 3/2019 | Low et al. |
| 2019/0161531 A1 | 5/2019 | Pule et al. |
| 2019/0209611 A1 | 7/2019 | Eckardt et al. |
| 2019/0224237 A1 | 7/2019 | Jensen et al. |
| 2019/0255109 A1 | 8/2019 | Low et al. |
| 2019/0292517 A1 | 9/2019 | Cheung et al. |
| 2019/0388468 A1 | 12/2019 | Lock et al. |
| 2020/0023009 A1 | 1/2020 | Low et al. |
| 2020/0054676 A1 | 2/2020 | Low et al. |
| 2020/0087399 A1 | 3/2020 | Jensen et al. |
| 2020/0123224 A1 | 4/2020 | Scharenberg |
| 2020/0354477 A1 | 11/2020 | Jensen et al. |
| 2020/0405760 A1 | 12/2020 | Low et al. |
| 2021/0147871 A1 | 5/2021 | Scharenberg et al. |
| 2021/0308267 A1 | 10/2021 | Low et al. |
| 2021/0317407 A1 | 10/2021 | Jensen et al. |
| 2021/0340573 A1 | 11/2021 | Scharenberg et al. |
| 2021/0346431 A1 | 11/2021 | Messmann et al. |
| 2022/0000996 A1 | 1/2022 | Low et al. |
| 2022/0017920 A1 | 1/2022 | Scharenberg et al. |
| 2022/0257652 A1 | 8/2022 | Jensen et al. |
| 2022/0280648 A1 | 9/2022 | Low et al. |
| 2022/0409747 A1 | 12/2022 | Low et al. |
| 2023/0068879 A1 | 3/2023 | Jensen et al. |
| 2023/0172981 A1 | 6/2023 | Jensen et al. |
| 2023/0322925 A1 | 10/2023 | Jensen et al. |
| 2023/0348624 A1 | 11/2023 | Scharenberg et al. |

FOREIGN PATENT DOCUMENTS

| | | |
|---|---|---|
| CN | 106163547 A | 11/2016 |
| EP | 0340793 | 11/1989 |
| EP | 2177230 A1 | 4/2010 |
| EP | 10009345 | 9/2010 |
| EP | 2537416 | 11/2014 |
| EP | 2934532 | 10/2015 |
| EP | 2614077 B1 | 8/2016 |
| EP | 3653212 | 5/2020 |
| EP | 4282419 | 11/2023 |
| JP | 2015525765 A | 9/2015 |
| JP | 2016534995 A | 11/2016 |
| JP | 2017507919 A | 3/2017 |
| WO | WO 1986/04356 | 7/1986 |
| WO | WO 1992/10591 | 6/1992 |
| WO | WO 1992/15322 | 9/1992 |
| WO | WO 1992/15671 | 9/1992 |
| WO | WO-9215322 A1 | 9/1992 |
| WO | WO-9530014 A1 | 11/1995 |
| WO | WO 1997/23613 | 7/1997 |
| WO | WO-9723613 A2 | 7/1997 |
| WO | WO 1997/34634 | 9/1997 |
| WO | WO-9734634 A1 | 9/1997 |
| WO | WO 1999/58572 | 11/1999 |
| WO | WO-9958572 A1 | 11/1999 |
| WO | WO-0014257 | 3/2000 |
| WO | WO 2000/023573 | 4/2000 |
| WO | WO-0023573 A2 | 4/2000 |
| WO | WO 1995/30014 | 11/2000 |
| WO | WO 2001/091625 | 12/2001 |
| WO | WO 2002/088334 | 11/2002 |
| WO | WO 2005/079836 | 9/2005 |
| WO | WO-2005079836 A1 | 9/2005 |
| WO | WO-2005044716 A2 | 9/2005 |
| WO | WO 2006/029879 | 3/2006 |
| WO | WO 2006/036445 | 4/2006 |
| WO | WO-2006036445 A2 | 4/2006 |
| WO | WO 2008/031577 | 3/2008 |
| WO | WO-2008031577 A1 | 3/2008 |
| WO | WO 2008/045437 | 4/2008 |
| WO | WO-2008045437 A2 | 4/2008 |
| WO | WO 2008/057437 | 5/2008 |
| WO | WO 2008/121420 | 10/2008 |
| WO | WO-2008121420 A1 | 10/2008 |
| WO | WO-2009091826 A2 | 7/2009 |
| WO | WO 2009/091826 | 9/2009 |
| WO | WO-2009117117 A1 | 9/2009 |
| WO | WO 2010/025177 | 3/2010 |
| WO | WO 2011/041093 | 4/2011 |
| WO | WO-2011041093 A1 | 4/2011 |
| WO | WO 2011/059836 | 5/2011 |
| WO | WO-2011059836 A2 | 5/2011 |
| WO | WO 2012/031744 | 3/2012 |
| WO | WO-2012028241 A1 | 3/2012 |
| WO | WO-2012031744 A1 | 3/2012 |
| WO | WO 2012/054825 | 4/2012 |
| WO | WO-2012054825 A1 | 4/2012 |
| WO | WO 2012/028241 | 6/2012 |
| WO | WO 2012/079000 | 6/2012 |
| WO | WO 2012/082841 | 6/2012 |
| WO | WO-2012079000 A1 | 6/2012 |
| WO | WO 2012/099973 | 7/2012 |
| WO | WO-2012099973 A2 | 7/2012 |
| WO | WO 2012/129514 | 9/2012 |
| WO | WO-2012129514 A1 | 9/2012 |
| WO | WO 2012/138475 | 10/2012 |
| WO | WO 2013/019615 | 2/2013 |
| WO | WO-2013019615 A2 | 2/2013 |
| WO | WO 2013/039889 | 3/2013 |
| WO | WO 2013/044225 | 3/2013 |
| WO | WO-2013044225 A1 | 3/2013 |
| WO | WO 2013/063419 | 5/2013 |
| WO | WO 2013/067492 | 5/2013 |
| WO | WO 2013/071154 | 5/2013 |
| WO | WO-2013063419 A2 | 5/2013 |
| WO | WO-2013067492 A1 | 5/2013 |
| WO | WO-2013071154 A1 | 5/2013 |
| WO | WO 2013/088446 | 6/2013 |

(56) References Cited

FOREIGN PATENT DOCUMENTS

| | | |
|---|---|---|
| WO | WO 2013/093809 | 6/2013 |
| WO | WO-2013088446 A1 | 6/2013 |
| WO | WO-2013093809 A1 | 6/2013 |
| WO | WO 2013/112986 | 8/2013 |
| WO | WO 2013/123061 | 8/2013 |
| WO | WO 2013/126726 | 8/2013 |
| WO | WO-2013112986 A1 | 8/2013 |
| WO | WO-2013123061 A1 | 8/2013 |
| WO | WO-2013126726 A1 | 8/2013 |
| WO | WO 2013/166321 | 11/2013 |
| WO | WO 2013/177247 | 11/2013 |
| WO | WO-2013166321 A1 | 11/2013 |
| WO | WO 2014/011984 | 1/2014 |
| WO | WO-2014011987 A1 | 1/2014 |
| WO | WO 2014/031687 | 2/2014 |
| WO | WO-2014031687 A1 | 2/2014 |
| WO | WO 2014/039523 | 3/2014 |
| WO | WO 2014/043441 | 3/2014 |
| WO | WO-2014039523 A1 | 3/2014 |
| WO | WO 2014/055668 | 4/2014 |
| WO | WO 2014/055771 | 4/2014 |
| WO | WO 2014i055771 | 4/2014 |
| WO | WO-2014055668 A1 | 4/2014 |
| WO | WO-2014068388 A1 | 5/2014 |
| WO | WO 2014/099671 | 6/2014 |
| WO | WO 2014/100385 | 6/2014 |
| WO | WO 2014/100615 | 6/2014 |
| WO | WO-2014099671 A1 | 6/2014 |
| WO | WO-2014100385 A1 | 6/2014 |
| WO | WO 2015/107075 | 7/2014 |
| WO | WO 2014/124143 | 8/2014 |
| WO | WO 2014/130635 | 8/2014 |
| WO | WO-2014124143 A1 | 8/2014 |
| WO | WO-2014127261 A1 | 8/2014 |
| WO | WO-2014130635 A1 | 8/2014 |
| WO | WO 2014/152177 | 9/2014 |
| WO | WO 2014/153002 | 9/2014 |
| WO | WO-2014152177 A1 | 9/2014 |
| WO | WO-2014153002 A1 | 9/2014 |
| WO | WO 2015/057834 | 4/2015 |
| WO | WO 2015/057852 | 4/2015 |
| WO | WO-2015107075 A1 | 7/2015 |
| WO | WO 2015/123496 | 8/2015 |
| WO | WO-2015123496 A1 | 8/2015 |
| WO | WO 2015/188135 | 10/2015 |
| WO | WO-2015164594 A1 | 10/2015 |
| WO | WO-2015188135 A1 | 12/2015 |
| WO | WO 2016/025322 | 2/2016 |
| WO | WO 2016/025454 | 2/2016 |
| WO | WO-2016025454 A2 | 2/2016 |
| WO | WO-2016073755 A2 | 5/2016 |
| WO | WO 2016/102965 | 6/2016 |
| WO | WO-2016098078 A2 | 6/2016 |
| WO | WO 2016/054520 | 7/2016 |
| WO | WO 2016/109668 | 7/2016 |
| WO | WO 2016/132366 | 8/2016 |
| WO | WO-2016132366 A1 | 8/2016 |
| WO | WO 2016/149665 | 9/2016 |
| WO | WO 2016/154621 | 9/2016 |
| WO | WO-2016154621 A1 | 9/2016 |
| WO | WO 2016/168766 | 10/2016 |
| WO | WO 2016/168769 | 10/2016 |
| WO | WO 2016/168773 | 10/2016 |
| WO | WO-2016168773 A2 | 10/2016 |
| WO | WO 2016/201300 | 12/2016 |
| WO | WO 2016/210447 | 12/2016 |
| WO | WO 2017/029511 | 2/2017 |
| WO | WO 2017/029512 | 2/2017 |
| WO | WO-2017025638 A1 | 2/2017 |
| WO | WO 2017/035362 | 3/2017 |
| WO | WO 2017/062628 | 4/2017 |
| WO | WO 2017/068360 | 4/2017 |
| WO | WO 2017/068361 | 4/2017 |
| WO | WO-2017062628 A1 | 4/2017 |
| WO | WO 2017/123548 | 7/2017 |
| WO | WO-2017114497 A1 | 7/2017 |
| WO | WO-2017123548 A1 | 7/2017 |
| WO | WO 2017/136829 | 8/2017 |
| WO | WO 2017/137758 | 8/2017 |
| WO | WO 2017/137759 | 8/2017 |
| WO | WO 2017/143150 | 8/2017 |
| WO | WO-2017136829 A1 | 8/2017 |
| WO | WO-2017143094 A1 | 8/2017 |
| WO | WO-2017143150 A1 | 8/2017 |
| WO | WO 2017/165245 | 9/2017 |
| WO | WO 2017/165571 | 9/2017 |
| WO | WO 2017/177149 | 10/2017 |
| WO | WO 2017/180587 | 10/2017 |
| WO | WO 2017/214167 | 12/2017 |
| WO | WO 2017/214170 | 12/2017 |
| WO | WO 2017/216561 | 12/2017 |
| WO | WO 2017/216562 | 12/2017 |
| WO | WO-2017214167 A1 | 12/2017 |
| WO | WO-2017214170 A2 | 12/2017 |
| WO | WO-2018013797 A1 | 1/2018 |
| WO | WO 2018/031694 | 2/2018 |
| WO | WO-2018031694 A1 | 2/2018 |
| WO | WO 2018/075794 | 4/2018 |
| WO | WO 2018/075807 | 4/2018 |
| WO | WO 2018/075813 | 4/2018 |
| WO | WO-2018075794 A1 | 4/2018 |
| WO | WO-2018075807 A1 | 4/2018 |
| WO | WO-2018075813 A1 | 4/2018 |
| WO | WO 2018/080541 | 5/2018 |
| WO | WO-2018080541 A1 | 5/2018 |
| WO | WO 2018/102761 | 6/2018 |
| WO | WO 2018/111763 | 6/2018 |
| WO | WO 2018/111834 | 6/2018 |
| WO | WO-2018102761 A1 | 6/2018 |
| WO | WO-2018115146 A1 | 6/2018 |
| WO | WO 2018/148224 | 8/2018 |
| WO | WO-2018152451 A1 | 8/2018 |
| WO | WO 2018/160622 | 9/2018 |
| WO | WO 2018/165194 | 9/2018 |
| WO | WO 2018/165198 | 9/2018 |
| WO | WO 2018/170150 | 9/2018 |
| WO | WO 2018/175453 | 9/2018 |
| WO | WO-2018165194 A1 | 9/2018 |
| WO | WO-2018165198 A1 | 9/2018 |
| WO | WO-2018170150 A2 | 9/2018 |
| WO | WO-2018175453 A1 | 9/2018 |
| WO | WO 2018/213332 | 11/2018 |
| WO | WO-2018213332 A1 | 11/2018 |
| WO | WO 2019/028190 | 2/2019 |
| WO | WO 2019/033050 | 2/2019 |
| WO | WO-2019028190 A1 | 2/2019 |
| WO | WO-2019033050 A1 | 2/2019 |
| WO | WO-2019144091 A1 | 7/2019 |
| WO | WO-2019144095 A1 | 7/2019 |
| WO | WO-2019156795 A1 | 8/2019 |
| WO | WO-2019165237 A1 | 8/2019 |
| WO | WO-2019210057 A1 | 10/2019 |
| WO | WO-2020033129 A1 | 2/2020 |
| WO | WO-2020033272 A1 | 2/2020 |
| WO | WO-2021007109 A1 | 1/2021 |
| WO | WO-2021055641 A1 | 3/2021 |
| WO | WO-2021076788 A2 | 4/2021 |
| WO | WO-2021154839 A1 | 8/2021 |
| WO | WO-2021158523 A1 | 8/2021 |
| WO | WO-2021158534 A1 | 8/2021 |
| WO | WO-2021178887 A1 | 9/2021 |
| WO | WO-2022015955 A1 | 1/2022 |
| WO | WO-2022109162 A1 | 5/2022 |
| WO | WO-2022164935 A1 | 8/2022 |
| WO | WO-2023240248 A2 | 12/2023 |

OTHER PUBLICATIONS

Altschul et al., "Local Alignment Statistics, [27] Multiple Alignment and Phylogenetic Trees," Methods in Enzymology 266:460-480 (1996).

Amin et al., "The Eighth Edition AJCC Cancer Staging Manual Continuing to Build a Bridge From a Population-Based to a More

(56) References Cited

OTHER PUBLICATIONS

"Personalized" Approach to Cancer Staging," CA Cancer J Cun 67(2):93-99 (2017).
Berger et al., "Safety of targeting ROR1 in primates with chimeric antigen receptor modified T cells," Cancer Immunology Research, 3(2):206-216 (2015).
Betancur et al., "Nonpeptide antagonists of neuropeptide receptors: tools for research and therapy," Trends Pharmacol Sci. 18(10): 372-386 (1997).
Carpenter, R. O., et al. "B-cell Maturation Antigen is a Promising Target for Adoptive T-cell Therapy of Multiple Myeloma," Clinical Cancer Research, 2013, vol. 19(8), pp. 2048-2060.
Cheng et al., "Hapten-directed targeting to single-chain antibody receptors," Cancer Gene Therapy, 11(5):380-388 (2004).
Chothia, et al., "Conformations of immunoglobulin hypervariable regions," Nature, Dec. 28, 1989, vol. 342, pp. 877-883.
Cianciulli, A. et al., "Folic Acid Is Able to Polarize the Inflammatory Response in LPS Activated Microglia by Regulating Multiple Signaling Pathways", Mediators of Inflammation, 2016, 10 pages.
Cooper et al., "Enhanced antilymphoma efficacy of CD19-redirected influenza MP1-specific CTLs by cotransfer of T cells modified to present influenza MP1," Blood 2005, vol. 105 No. 4 pp. 1622-1631.
Deng et al, "Antitumor activity of NKG2D CAR-T cells against human colorectal cancer cells in vitro and in vivo," Am J Cancer Res 9(5)945-958 (2019).
Extended European Search Report issued by the European Patent office for Application No. 18761400.3, dated Sep. 24, 2020, 7 pages.
Extended European Search report issued by the European Patent Office for Application No. 19741309.9, dated Oct. 5, 2021, 12 pages.
Extended European Search Report issued by the European Patent Office for Application No. 19757681.2, dated Nov. 25, 2021, 9 pages.
Extended European Search report issued by the European Patent Office for Application No. 23169858.0, dated Oct. 30, 2023, 9 pages.
Extended European Search Report issued by the European Patent Office for Application No. EP17779919, dated Nov. 6, 2019, 7 pages.
Fang, R.H., et al., "Lipid-insertion Enables Targeting Functionalization of Erythrocyte Membrane-cloaked Nanoparticles," Nanoscale, Oct. 2013, vol. 5(19), pp. 8884-8888.
FDA Approval Letter dated Apr. 23, 2014, for Biologics License Application for SYLVANT™ (siltuximab), 12 pages.
FDA Approval Letter dated Jan. 8, 2010, for Biologics License Application for Acternra (tocilizumab), 9 pages.
Figini, M, et al., "Panning phage antibody libraries on cells: isolation of human Fab fragments against ovarian carcinoma using guided selection," Cancer Res (Mar. 1, 1998); 58(5):991-996.
Gu et al., "Abstract LB-187: New methods for controlling CAR Tcell-mediated cytokine storms : Cancer Research", Proceedings: AACR Annual Meeting 2017, (Jul. 1, 2017), Retrieved from the Internet Sep. 28, 2021: URL:https://cancerres.aacrjournals.org/content/77/13 Supplement/LB-187, 4 pages.
Hennig I.M., et al., "Substance-P Receptors in Human Primary Neoplasms: Tumoral and Vascular Localization," International Journal of Cancer, 1995, vol. 61(6), pp. 786-792.
Honegger et al., "A mutation designed to alter crystal packing permits structural analysis of a tight- binding fluorescein-scFv complex," Protein Science 14(10): 2537-2549 (2005).
Hong, Soon-Sun et al., "A Novel Small-Molecule Inhibitor Targeting the IL-6 Receptor β Subunit, Glycoprotein 130," J Immunol 2015; 195:237-245; Prepublished online May 29, 2015; doi: 10.4049/jimmunol.1402908 http://www.jimmunol.org/content/195/1/237.
International Search Report and Written Opinion dated Mar. 27, 2019 for PCT/US2019/014478, 8 pages.
International Search Report and Written Opinion issued by the International Searching Authority for Application No. PCT/US2017/026618, completed Aug. 30, 2017, 12 pages.
International Search Report and Written Opinion issued by the International Searching Authority for Application No. PCT/US2019/019191, completed Jun. 11, 2021, 11 pages.
International Search Report issued in Appl. No. PCT/US2019/014472 (Apr. 26, 2019), 15 pages.
International Search Report prepared for PCT/US2013/076986, mailed Apr. 28, 2014, 15 pages.
Johnson et al., "Kabat database and its applications: 30 years after the first variability plot," Nucleic Acids Res., 28(1): 214-218 (2000).
Kanduluru et al., "Design, Synthesis, and Evaluation of a Neurokinin-1 Receptor-Targeted Near-IR Dye for Fluorescence-Guided Surgery of Neuroendocrine Cancers," Bioconjugate Chem. 27, 2157-2165 (2016).
Kim et al., "NMR Structural Studies of Interactions of a Small, Nonpeptidyl Tpo Mimic with the Thrombopoietin Receptor Extracellular Juxtamembrane and Transmembrane Domains," J Biol Chem (2007) 282(19)14253-14261.
Kranz et al., "Partial elucidation of an anti-hapten repertoire in BALB/c mice comparative characterization of several monoclonal antiFLuorescyl antibodies," Mol Immunol (1981) 18(10), 889-898.
Kunik et al., "Paratome: an online tool for systematic identification of antigen-binding regions in antibodies based on sequence or structure," Nucl Acids Res. 40:W521-W524 (2012).
Le; Robert Q. et al. "FDA Approval Summary: Tocilizumab for Treatment of ChimericAntigen Receptor T Cell-Induced Severe or Life-Threatening CytokineRelease Syndrome," The Oncologist 23:943-947 (2018).
Lee et al., "Use of a Single CAR T Cell and Several Bispecific Adapters Facilitates Eradication of Multiple Antigenically Different Solid Tumors," Cancer Res 79:387-396 (2019).
Lefranc, MP. et al., "IMGT unique numbering for immunoglobulin and T cell receptor variable domains and Ig superfamily V-like domains," Developmental & Comparative Immunology, Jan. 2003, 27(1), pp. 55-77.
Li et al, "CAIX-specific CAR-T Cells and Sunitinib Show Synergistic Effects Against Metastatic Renal Cancer Models," Journal of Immunotherapy 43 16-4328 (2020).
Lu et al: "Preclinical Evaluation of Bispecific Adaptor Molecule Controlled Folate Receptor CAR-T Cell Therapy With Special Focus on Pediatric Malignancies", Frontiers in Oncology, vol. 9, pp. 1-20 (2019).
Maeda, et al., "Tumor vascular permeability and the EPR effect in macromolecular therapeutics: a review," Journal of Controlled Release 65 (2000), pp. 271-284 (14 pages).
Makabe et al., "Thermodynamic consequences of mutations in Vernier zone residues of a humanized anti-human epidermal growth factor receptor murine antibody," Journal of Biological Chemistry, 283(2):1156-1166 (2008).
Martin et al., "Modeling antibody hypervariable loops: a combined algorithm," Proc Natl Acad Sci (USA), 86:9268-9272 (1989).
Maus et al., "Antibody-modified T cells: CARs take the front seat for hematologic malignancies," Blood 123(17):2626-2635 (2014).
Miguel Muñoz, Rafael Coveñas, "Substance P," Encyclopedia of Endocrine Diseases (Second Edition), vol. 1, pp. 571-578 (2018).
Molecular Cloning A Laboratory Manual, 4th Edition, Cold Spring Harbor Laboratory Press, (2012) Green and Sambrook, TOC, 34 pages (2012).
Morgan, R. A. et al., "Case Report of a Serious Adverse Event Following the Administration of T Cells Transduced With a Chimeric Antigen Receptor Recognizing ERBB2," Molecular Therapy, vol. 18, No. 4, pp. 843-851 (Apr. 2010).
Nolan K F, et al, "Bypassing immunization: optimized design of 'designer T cells' against carcinoembryonic antigen (CEA)-expressing tumors, and lack of suppression by soluble CEA," Clinical Cancer Research (Dec. 1999); 5(12): 3928-3941.
PCT Search Report and Written Opinion prepared for PCT/US2018/020095, completed Jul. 17, 2018, 12 pages.
Peng-Cheng, "Evaluation of a Carbonic Anhydrase IX-Targeted near-Infrared Dye for Fluorescence-Guided Surgery of Hypoxic Tumors," Mol. Pharmaceutics, 13:1618-1625 (2016).

(56) References Cited

OTHER PUBLICATIONS

Peprotech, Recombinant Human 4-IBB Receptor, https://www.peprotech.com/recombinant- human-4-1 bb-receptor, downloaded Jul. 25, 2018, 5 pages, dated 2017.
Pule et al., "Virus-specific T cells engineered to coexpress tumor-specific receptors: persistence and antitumor activity in individuals with neuroblastoma," Nat. Med. (2008); 14: 1264-1270.
Sambrook, et al., Molecular Cloning: A Laboratory Manual, 3rd Edition, Cold Spring Harbor Laboratory Press, Cold Spring Harbor, New York, 2001, 9.47-9.55.
Samudrala et al., "Ab Initio Protein Structure Prediction Using a Combined Hierarchical Approach," Proteins, Structure, Function and Genetics Suppl., 3:194-198 (1999).
Sang et al., "The research development of Chimeric Antigen Receptor T-cells in hematological malignancies," Practical Oncology Journal, vol. 30, No. 5, (Oct. 28, 2016), pp. 473-476.
Schwesinger et al., "Unbinding forces of single antibody-antigen complexes correlate with their thermal dissociation rates," PNAS (2000) 97(18), 9972-9977.
Shishkin A.M., Development of a method of adoptive immunotherapy of cancer-embryonic antigen positive human tumors, Moscow, FGBU "Russian Scientific Center of radiology and nuclear medicine," 2015, 23 pages including English Summary.
Sun et al., "Immunotherapy with CAR-Modified T cells: toxicities and overcoming strategies," Journal of Immunology Research, 2018:1-10 (2018).
Tamada et al., Correction Feb. 14, 2013, "Redirecting Gene-Modified T Cells Toward Various Cancer Types Using Tagged Antibodies," Clinical Cancer Research 2012:18(23)6436-6445, 2 pages.
Uherek, C, et al., "Retargeting of natural killer-cell cytolytic activity to ErbB2 expressing cancer cells results in efficient and selective tumor cell destruction," Blood (2002); 100: 1265-1273.
U.S. Appl. No. 62/253,465, inventor Kim:Chanhyuk, filed Nov. 10, 2015.
Van Blitterswijk et al., "Anticancer mechanisms and clinical application of alkylphospholipids," Biochimica et Biophysica Acta (2013) 1831(3)663-674.
Van Der Luit et al., "A new class of anticancer alkylphospholipids uses lipid rafts as membrane gateways to induce apoptosis in lymphoma cells," Mol Cancer Ther (2007) 6(8)2337-2345.
Van Der Stegen et al., "The pharmacology of second-generation chimeric antigen receptors." Nature reviews Drug Discovery 14(7):499-509 (2015).
Van Rhijn I. V., et al., "Human Autoreactive T Cells Recognize CD1band Phospholipids," Proceedings of the National Academy of Sciences, Nov. 30, 2015, vol. 113(2), pp. 380-385.
Wang et al., "Current status and perspectives of chimeric antigen receptor modified T cells for cancer treatment," Protein Cell2017, 8(12):896-925.
Webpage, COVID-19 Treatment Guidelines—Interleukin-6 Inhibitors, dated Sep. 26, 2022, 5 pages, retrieved online on Oct. 7, 2022 at https://www.covid19treatmentguidelines.nih.gov/therapies/immunomodulators/interleukin-6-inhibitors/.
Wikipedia, Interleukin 10, https://en.wikipedia.org/w/index.php?title=Interleukin_10&oldid=835415026, downloaded Apr. 8, 2018, 16 pages, undated.
Zarour, "Reversing T-cell dysfunction and exhaustion in cancer," Clinical Cancer Research, 22(8): 1856-1864 (2016).
Zheng, F. et al., "Relationship between levels of serum folate and inflammatory cytokines in hypertension cases". Zhongguo Redai Yixue (2015), 15(5), 521-524.
U.S. Appl. No. 62/253,467, filed Nov. 10, 2015, Young et al.
U.S. Appl. No. 61/473,409, filed Apr. 8, 2011, Morgan et al.
U.S. Appl. No. 61/701,056, filed Sep. 14, 2012, Robbins et al.
U.S. Appl. No. 61/891,347, filed Oct. 15, 2013, Cao et al.
U.S. Appl. No. 61/895,704, filed May 25, 2013, Cao et al.
U.S. Appl. No. 62/009,054, filed Jun. 6, 2014, Young et al.
U.S. Appl. No. 62/009,056, filed Jun. 6, 2014, Cao et al.
U.S. Appl. No. 62/030,514, filed Jul. 29, 2014, Wang et al.
U.S. Appl. No. 62/030,526, filed Jul. 29, 2014, Wang et al.
U.S. Appl. No. 62/059,752, filed Mar. 10, 2014, Kim et al.
U.S. Appl. No. 62/108,947, filed Jan. 28, 2015, Kim et al.
U.S. Appl. No. 62/148,063, filed Apr. 15, 2015, Young et al.
U.S. Appl. No. 62/148,070, filed Apr. 15, 2015, Kim et al.
U.S. Appl. No. 62/253,465, filed Nov. 10, 2015, Kim et al.
"Chain A, 4m5.3 Anti-Fluorescein Single Chain Antibody Fragment (Scfv)" (4 pages), retrieved from https://www.ncbi.nlm.nih.gov/protein/62738392?report=genbank&log$=protalign&blast_rank=I&RID=UW AEY60801 Ron Oct. 12, 2016.
"Common Terminology Criteria for Adverse Events (CTCAE)" National Cancer Institute Common Toxicity Criteria version 4.03 (NCI-CTCAE v4.03 (2010) (196 pages).
"Recent patent applications in chimeric antigen receptors," *Nature Biotechnology*, 2014, 32, 239.
"Recombinant Human 4-IBB Receptor" (1 page), retrieved from https://www.peprotech.com/en- US/Pages/Product/Recombinant Human 4-IBB Receptor/310-15 on May 13, 2016.
"TNF Superfamily Pathway," ThermoFinder Scientific.
"Tumor necrosis factor receptor superfamily," HUGO Gene Nomenclature Committee.
"UniProtKB—P20334 (TNR9_MOUSE)" (11 pages), retrieved from http://www.uniprot.org/uniprot/P20334 on Oct. 14, 2016.
"UniProtKB—P24161 (CD3Z_MOUSE)" (12 pages), retrieved from http://www.uniprot.org/uniprot/P24I6I on Oct. 14, 2016.
Abate-Daga, et al., "Abstracts for the 25th Annual Scientific Meeting of the International Society for Biological Therapy of Cancer," Journal of Immunotherapy (2010); 33(8): 859-920 (http://journals.lww.com/immunotherapyjournal/Citation/2010/10000/Abstracts_for_the_25th_Annual_Scientific_Meeting.13.aspx).
Abken, H. et al. "Chemeric T-Cell Receptors: Highly Specific Tools To Target Cytotoxic T-Lymphocytes To Tumour Cells," Cancer Treatment Reviews (1997); 23:97-112.
Abken, H., et al., "Tuning tumor-specific T-cell activation: a matter of costimulation?" Trends in Immunology vol. 23 No. May 2002: 240-45.
Abstracts for the 26th Annual Scientific Meeting of the Society for Immunotherapy of Cancer (SITC), J Immunother., vol. 34, No. 9, Nov.-Dec. 2011 (62 pages).
Airenne et al., "Recombinant avidin and avidin-fusion proteins", Biomolecular Engineering 16 {I 999) 87-92.
Alcover et al., "A soluble form of the human CD8 alpha chain expressed in the baculovirus system: Biochemical characterization and binding to MHC Class I", Molecular Immunology, vol. 30, No. I, pp. 55-67, 1993.
Alexander et al., "Indoleamine 2,3-Dioxygenase Expression in Transplanted NOD Islets Prolongs Graft Survival After Adoptive Transfer of Diabetogenic Splenocytes," Diabetes 2002, vol. 51 pp. 356-365.
Alonso-Camino et al. "CARbodies: Human Antibodies Against Cell Surface Tumor Antigens Selected From Repertoires Displayed on T Cell Chimeric Antigen Receptors." (2013) Mal Ther Nucl Acids 2, e93 (11 pages).
Altenschmidt, U. et al. "Adoptive transfer of in vitro-targeted, activated T lymphocytes results in total tumor regression," J. Immunol. (1997); 159:5509-15.
Altenschmidt, U., et al., "Specific cytotoxic T lymphocytes in gene therapy," J. Mol. Med. (1997); 75, 259-266.
Altvater, B., et al., "284 (CD244) Signaling by Recombinant Antigen-specific Chimeric Receptors Costimulates Natural Killer Cell Activation to Leukemia and Neuroblastoma Cells", Clin Cancer Res 2009;15(15) Aug. 1, 2009: 4857-66.
Alvarez-Vallina, L. et al., "Antigen-specific targeting of CD28-mediated T cell co-stimulation using chimeric single-chain antibody variable fragment-CD28 receptors," Eur. J. Immunol, 1996, 26, 2304-2309.
An et al., "IgG2m4, an engineered antibody isotype with reduced Fe function," mAbs 2009, Landes Bioscience, 1:6, 572-579.
Ang et al., "Generating a Chimeric Antigen Receptor To Redirect T-Cell Specificity after Infusion", Molecular Therapy vol. 19, Suonlement 1, May 2011, S137-S138.
Arch, R, et al., "4-1BB and Ox40 Are Members of a Tumor Necrosis Factor (TNF)-Nerve Growth Factor Receptor Subfamily That Bind

(56) References Cited

OTHER PUBLICATIONS

TNF Receptor-Associated Factors and Activate Nuclear Factor kB," Molecular And Cellular Biology (1998); 558-565.
Aruffo, A, et al., "Molecular cloning of a CD28 cDNA by a high-efficiency COS cell expression system," Proc. Nati. Acad. Sci. USA (1987); 84: 8573-8577.
AVD-Avidin precursor, UniProtKB-P02701 (AVID_CHICK).
Baba et al., "N-Linked Carbohydrate on Human Leukocyte Antigen-C and Recognition by Natural Killer Cell Inhibitory Receptors", Human Immunology 61, 1202-1218 (2000).
Bader, ET, et al., "Directed evolution of antibody fragments with monovalent femtomolar antigen-binding affinity," PNAS, 97(20), 10701-05, 2000.
Baniyash et al., "The T Cell Antigen Receptor Zeta Chain Is Tyrosine Phosphorylated open Activation" The Journal of Biological Chemistry, vol. 263, No. 34, Issue of Dec. 5, 1988, pp. 18225-18230.
Barber et al. "Chimeric NKG2D Receptor-Bearing T Cells as Immunotherapy for Ovarian Cancer," Cancer Res. (2007);67(10): 5003-5008.
Barber, et al., "Chimeric NKG2D Receptor-Expressing T Cells as an Immunotherapy for Multiple Myeloma," Exp Hematol. (Oct. 2008); 36(10):1318-28.
Barber, et al., "Immunotherapy with chimeric NKG2D receptors leads to long-term tumor-free survival and development of host antitumor immunity in murine ovarian cancer," J. immunol 180:72-78 (2008).
Barber, et al., J Immunol. (Aug. 1, 2014); 193(3): 1513: (Erratum to Barber et al. "Immunotherapy with chimeric NKG2D receptors leads to long-term tumor-free survival and development of host antitumor immunity in murine ovarian cancer," J. Immunol. (2008); 180:72-78).
Barber, et al., "Chimeric NKG2D expressing T cells eliminate immunosuppression and activate immunity within the ovarian tumor microenvironment," J. Immunol. (2009); 183:6939-47.
Barocas et al., "A population-based study of renal cell carcinoma and prostate cancer in the same patients," BJU International, (2006) 97(1): 33-36.
Barrett et al., Chimeric Antigen Receptor Therapy for Cancer Annual Review of Medicine vol. 65: 333-347 (2014).
Bauer et al., "Activation of NK Cells and T Cells by NKG2D, a Receptor for Stress-Inducible MICA," Science 1999, vol. 285 DD. 727-729.
Bauer, A, et al., Differential signal transduction via T-cell receptor CD3'2, CD3C-,v, and CD3'q2 isoforms,• Proc. Nati. Acad. Sci. USA (1991); 88: 3842-3846.
Baum et al. "Retrovirus vectors: toward the plentivirus?" (2006) Molecular Therapy: The Journal of the American Society of Gene Therapy. 13:1050-1063.
Becker, M. L. B., et al., "Expression of a hybrid immunoglobulin-T cell receptor protein in transgenic mice," Cell (1989); 58:911-921.
Bedzyk, WD et al., "Active site structure and antigen binding properties of idiotypically cross-reactive anti-fluorescein monoclonal antibodies," J Biol Chem., 1990, 265,133-138.
Bejcek, 8, et al., "Development and Characterization of Three Recombinant Single Chain Antibody Fragments (scFvs) Directed against the CD19 Antigen1," Cancer Research 55, (1995); 2346-2351.
Berg et al., "Section 3.2 Primary Structure: Amino Acids Are Linked by Peptide Bonds to Form Polypeptide Chains" Biochemistry. 5th Ed. New York. W.H. Freeman; 2002, pp. 1-16.
Berger, C., et al., Analysis of trans gene-specific immune responses that limit the in vivo persistence of adoptively transferred HSV-TK-modified donor T cells after allogeneic hematopoietic cell transplantation. Blood, 2006. 107(6): p. 2294-302.
BLAST Search page for "P20334[209-256]" (2 pages), retrieved from http://www.uniprot.org/blast/?about=P20334[209-256]&key=Topological%20domain on Oct. 14, 2016.
Bluemel, C., et al., Epitope distance to the target cell membrane and antigen size determine the potency ofT cell-mediated lysis by BiTE antibodies specific for a large melanoma surface antigen. Cancer Immunol Immunother (2010); 59(8): 1197-209.
Boder, ET, et al., "Directed evolution of antibody fragments with monovalent femtomolar antigen-binding affinity," PNAS, 97(20), 10701-05, 2000.
Bolhuis, R. L. et al. "Preparation for a phase I/II study using autologous gene modified T lymphocytes for treatment of metastatic renal cancer patients.," Adv. Exp. Med. Biol. (1998); 451:547-55.
Boomer et al., "Cutting Edge: A Double-Mutant Knockin of the CD28 YMNM and PYAP Motifs Reveals a Critical Role for the YMNM Motif in Regulation of T Cell Proliferation and Bcl-x L Expression" The Journal of Immunology. 2014; 192, pp. 3465-3469.
Boomer, J, et al.,. "An Enigmatic Tail of CD28 Signaling," Washington University School of Medicine (2010); 1-20.
Boulassel, M.R., et al., "Immunotherapy for B-Cell Neoplasms using T Cells expressing Chimeric Antigen Receptors: From antigen choice to clinical implementation," Sultan Qaboos Univ Med J (2012); 12(3): p. 273-85 (Epub Jul. 15, 2012).
Boursier et al., "Evidence for an Extended Structure of the T-cell Co-receptor CD8a as Deduced from the Hydrodynamic Properties of Soluble Forms of the Extracellular Region*," The Journal of Bioloaical Chemistry 1993, vol. 268, No. 3, Issue of Jan. 25, pp. 2013-2020.
Brennan et al., "Carbohydrate Recognition by a Natural Killer Cell Receptor, Ly-49C*," The Journal of Biological Chemistry 1995, vol. 270, No. 17, Issue of Apr. 28, pp. 9691-9694.
Brentjens et al., "CD19-targeted T cells rapidly induce molecular remissions in adults with chemotherapy-refractory acute lymphoblastic leukemia." Sci Transl Med. 2013 5(177) ra38 (11 pages).
Brentjens, et al., "Eradication of systemic B-cell tumors by genetically targeted human T lymphocytes co- stimulated by CD80 and interleukin-15," Nat. Med. (2003); 9: 279-286.
Brentjens, R., et al., Treatment of chronic lymphocytic leukemia with genetically targeted autologous T cells: case report of an unforeseen adverse event in a phase I clinical trial. Mol Tuer (2010); 18(4): 666-668.
Bridgeman, U.S., et al., "Structural and biophysical determinants of alpha beta T-cell antigen recognition," Immunology (Jan. 2012); 135(1): 9-18 (First published: Dec. 7, 2011).
Bruhns et al., Differential Roles of N- and C-Terminal Immunoreceptor Tyrosine-Based Inhibition Motifs During Inhibition of Cell Activation by Killer Cell Inhibitory Receptors,• The Journal of Immunology 1999; 162:3168-3175.
Bukczynski et al., "Costimulatory ligand 4-1 BBL (CD137L) as an efficient adjuvant of human antiviral cytotoxic T cell responses," Proc. Natl. Acad. Sci. USA, 2004, 101: 1291-1296.
Cambier, et al., "Antigen and Fe receptor signaling. The awesome power of the immunoreceptor tyrosine-based activation motif(ITAM)," J Immunol. (Oct. 1, 1995); 155(7):3281-5.
Camerini, D, et al,. "The T cell activation antigen CD27 is a member of the nerve growth factor/tumor necrosis factor receptor Qene family," The Journal of Immunoloav (1991); 3165-3169.
Cameron, B.J., et al., "Identification of a Titin-Derived HLA-A I-Presented Peptide as a Cross-Reactive Target for Engineered MAGE A3-Directed T Cells," Sci Transl Med (Aug. 7, 2013); 5(197):197ra103 (11 pages).
Canfield et al., The Binding Affinity of Human IgG for its High Affinity Fe Receptor Is Determined by Multiple Amino Acids in the CH2 Domain and Is Modulated by the Hinge Region,• J. Exp. Med. 1991, vol. 173 DD. 1483-1491.
Cannons et al., "4-1BB ligand induces cell division, sustains survival, and enhances effector function of CD4 and CDS T cells with similar efficacy," J Immunol. Aug. 2001, 167(3): 1313-1324.
Carlens et al. "Ex vivo T lymphocyte expansion for retroviral transduction: influence of serum-free media on variations in cell expansion rates and lymphocyte subset distribution." (2000) Exp Hematol 28(10): 1137-46.
Carpenito, C., et al., "Control of large, established tumor xenografts with genetically retargeted human T cells containing CD28 and CD137 domains," Proc Natl Acad Sci USA (2009); 106(9): 3360-5.

(56) References Cited

OTHER PUBLICATIONS

Carpenter, et al., "B-cell maturation antigen is a promising target for adoptive T-cell therapy of multiple myeloma," Clinical Cancer Research (2013); 19(8): 2048-2060 (published online Jan. 23, 2013).
Cartellieri, M. et al., "Chimeric antigen receptor-engineered T cells for immunotherapy of cancer," J. Biomedicine and Biotechnology, 2010. Article 1D 956304, 13 pages.
Cavalieri et al. "Human T lymphocytes transduced by lentiviral vectors in the absence of TCR activation maintain an intact immune competence." (2003) Blood. 102(2): 497-505.
Chalupny et al., "T-cell activation molecule 4-1BB binds to extracellular matrix proteins," Proc. Natl. Acad. Sci., USA, 89: 103360-10364 (Nov. 1992).
Chalupny, J, et al,."T-cell activation molecule 4-1BB binds to extracellular matrix proteins," Proc. Nat!. Acad. Sci. USA (1992); 89: 10360-10364.
Chang et al., "A Chimeric Receptor with NKG2D Specificity Enhances Natural Killer Cell Activation and Killing of Tumor Cells", Cancer Res 2013;73:1777-1786. Published online Jan. 9, 2013.
Cheadle et al, "Chimeric antigen receptors for T-cell based therapy" Methods Mal Biol. 2012; 907:645-66.
Chen et al. "Fusion protein linkers: property, design and functionality," Adv Drug Deliv Rev. (2013); 65: 1357-1369 (Epub Sep. 29, 2012).
Chen, et al. "Chimeric antigen receptor (CAR)-directed adoptive immunotherapy: a new era m targeted cancer therapy," Stem Cell Investig. (Jan. 18, 2014); 1:2 (2 pages).
Cho C. "Rapid identification of cytokine release syndrome after haploidentical PBSC transplantation and successful therapy with tocilizumab." *Bone Marrow Transplant.* Dec. 2016;51 (12):1620-1621, Epub Sep. 26, 2016.
Cho et al., "Macromolecular versus small-molecule therapeutics: drug discovery, development and clinical considerations" TIBTECH, vol. 14, May 1996, pp. 153-158.
Clay, et al., "Efficient transfer of a tumor antigen-reactive TCR to human peripheral blood lymphocytes confers anti-tumor reactivity," J. Immunol. (1999); 163:507-153.
Cohen et al. "Recognition of fresh human tumor by human peripheral blood lymphocytes transduced with a bicistronic retroviral vector encoding a murine anti-p53 TCR" (2005) J Immunol. 175:5799-5808.
Colcher, D. et al. "In vivo tumor targeting of a recombinant single-chain antigen-binding protein.," J. Nat. Cancer Inst. (1990); 82:1191-1197.
Cole et al., "The molecular determinants of CDS co-receptor function", 2012, Immunology, 137, 139-148.
Cooper et al. "T-cell clones can be rendered specific for CD19: toward the selective augmentation of the graft-versus-B-lineage leukemia effec" (2003) Blood. 101(4): 1637-1644.
Cooper et al., Sequence Listing, Compositions and Methods Related to a Human CD19-Specific Chimeric Antigen Receptor (H-CAR), U.S. Appl. No. 61/020,991, filed Jan. 14, 2008, 5 pages.
Cooper, "Test-driving CARs," Blood (Sep. 15, 2008); 112(6):2172-3.
Cordaro, T. A et al. "Tumor size at the time of adoptive transfer determines whether tumor rejection occurs," Eur. J. Immunol. (2000); 30: 1297-1307.
Croft, M., "The role of TNF superfamily members in T-cell function and diseases" Nature Reviews, Immunology, vol. 9, Apr. 2009, pp. 271-285.
Dai, et al., "Chimeric Antigen Receptors Modified T-Cells for Cancer Therapy," J Natl Cancer Inst (2016); 108(7): djv439 (14 pages) (First published online Jan. 27, 2016).
Dall, Peter et al., "In vivo cervical cancer growth inhibition by genetically engineered cytotoxic T cells." Cancer Immunol. Immunother. (Jan. 2005); 54(1):51-60.

Darcy, P. K. et al., "Expression in cytotoxic T lymphocytes of a single-chain anti-carcinoembryonic antigen antibody. Redirected Fas ligand-mediated lysis of colon carcinoma," Eur. J. Immunol. (1998); 28:1663-72.
Davila ML, et al., "How do CARs work?: Early insights from recent clinical studies targeting CD19," Oncoimmunology (Dec. 1, 2012); 1(9):1577-1583.
Davila M. L. et al: "Efficacy and toxicity management of 19-28z CAR T cell therapy in B cell acute lymphoblastic leukemia" Sci Transl Med. Feb. 19, 2014;6(224):224-25.
Davila Marco L. et al: "CD19-Targeted T Cells for Hematologic Malignancies—Clinical Experience to Date", Cancer Journal, vol. 21, No. 6, Jan. 1, 2015 (Jan. 1, 2015), pp. 470-474.
Davila, M.L., et al., "CD19 CAR-targeted T cells induce long-term remission and B Cell Aplasia in an immunocompetent mouse model of B cell acute lymphoblastic leukemia," PLoS One (Apr. 9, 2013); 8(4): p. e61338 (14 pages).
Debelouchina et al., "A molecular engineering toolbox for the structural biologist" Quarterly Reviews of Biophysics, 2017, 50, e7, pp. 1-41.
Definition of "Protein", Concise Dictionary of Biomedicine and Molecular Biology, 2nd Edition, Pei-Show Juo, PhD, 2002, p. 903.
Diefenbach et al., "The innate immune response to tumors and its role in the induction of T-cell immunity," Immunoloaical Reviews 2002, vol. 188: 9-21.
Dotti, et al. "Design and development of therapies using chimeric antigen receptor-expressing T cells." Immun Rev (Jan. 2014); 257(1): 107-126.
Dubrovska, A., et al., "A chemically induced vaccine strategy for prostate cancer," ACS Chem Biol (201 I); 6(11): 1223-31.
Duncan et al., Localization of the binding site for the human high-affinity Fe receptor on IgG, Nature 1998, vol. 332 pp. 563-564.
Ertl, H. C. et al., "Considerations for the clinical application of chimeric antigen receptor T cells: observations from a recombinant DNA advisory committee symposium held Jun. 15, 2010," Cancer Res., 2011, 71, 3175-3181.
Eshhar, Z., et al., "Specific activation and targeting of cytotoxic lymphocytes through chimeric single chains consisting of antibody-binding domains and the gamma or zeta subunits of the immuno-globulin and T-cell receptors," Proc. Natl. Acad. Sci. USA (1993); 90: 720-724.
Final Office Action issued by The United States Patent and Trademark Office for U.S. Appl. No. 15/296,666, dated Dec. 19, 2019, 8 pages.
Final Office Action issued by The United States Patent and Trademark Office for U.S. Appl. No. 15/296,666, dated Feb. 8, 2018, 6 pages.
Final Office Action issued by The United States Patent and Trademark Office for U.S. Appl. No. 15/296,666, dated Oct. 25, 2018, 8 pages.
Eshhar, et al, "Design of Cytotoxic T Lymphocytes with Antibody-Type Specificity against Tumor Cells Using Chimeric TcR," Journal of Cellular Biochemistry, Supplement 14B, UCLA Symposia on Molecular & Cellular Biology, Abstracts, 19th Annual Meeting, Jan. 27-Feb. 8, 1990, p. 70.
Eshhar, Z., et al., "Chimeric T cell receptor which incorporates the anti-tumour specificity of a monoclonal antibody with the cytolytic activity of T cells: a model system for immunotherapeutical approach," Br J Cancer. Suppl. (Jul. 1990); 10: 27-29.
Eshhar, Z., et al., "Functional expression of chimeric receptor genes in human T cells," J. Immunol. Meth. (2001); 248: 67-76.
Fedorov VD, et al., "PD-I- and CTLA-4-based inhibitory chimeric antigen receptors (iCARs) divert off-target immunotherapy responses," Sci Transl Med. (Dec. 11, 2013); 5(215):215ra172 (12 pages).
Feng et al., "Convergence on a Distinctive Assembly Mechanism by Unrelated Families of Activating Immune Receptors", Immunity, vol. 22, 427-438, Apr. 2005.
Feng et al., "The Assembly of Diverse Immune Receptors Is Focused on a Polar Membrane-Embedded Interaction Site", 2006. PLoS Biol 4(5):el42.
Ferrone, S., et al., "How much longer will tumor cells fool the immune system," Jmmunol. Today (2000); 21: 70-72.

(56) References Cited

OTHER PUBLICATIONS

Figini, M, et al., "Conversion of murine antibodies to human antibodies and their optimization for ovarian cancer therapy targeted to the folate receptor," Cancer Immunol Jmmunother (Apr. 2009); 58(4):531-46 (Epub Aug. 15, 2008).

Finney HM, et al., "Activation of resting human primary T cells with chimeric receptors: costimulation from CD28, inducible costimulator, CD134, and CD137 in series with signals from the TCR zeta chain," J Immunol. (2004); 172(1):104-13.

Finney, H. M., et al., "Chimeric receptors providing both primary and co-stimulatory signaling in T cells from a single gene product," J. Immunol. (1998); 161: 2791-2797.

Fitzer-Attas CJ, et al., "Harnessing Syk family tyrosine kinases as signaling domains for chimeric single chain of the variable domain receptors: optimal design for T cell activation," J Immunol. (1998); 160:145-154.

Foell et al., "CD137-mediated T cell co-stimulation terminates existing autoimmune disease in SLE-prone NZB/NZW F1 mice.," Ann NY Acad Sci. Apr. 2003; 987:230-5.

Frecha et al. "Advances in the field of lentivector-based transduction of T and B lymphocytes for gene therapy" (2010) Molecular Therapy: The Journal of the American Society of Gene Therapy. 18:1748-1757.

Friedmann-Morvinski, D., et al., "Redirected primary T cells harboring a chimeric receptor require co stimulation for their antigen-specific activation," Blood (2005); 105(8): 3087-3093.

Frost et al., "In Vitro Evaluation of Avidin Antibody Pretargeting Using • 'At-Labeled and Biotinylated Poly-L-Lysine as Effector Molecule*," Cancer 2010, Cancer Therapy With Antibodies and Immunoconiuaates, SuDDlement to Cancer, DD. 1101-1110.

Fujita, K. et al., "Prolonged disease-free period in patients with advanced epithelial ovarian cancer after adoptive transfer of tumor-infiltrating lymphocytes," Clin. Cancer Res., 1995, 1, 501-507.

Gade et al., "Targeted elimination of prostate cancer by genetically directed human T lymphocytes," Cancer Res. (2005); 65:9080-9088.

Gargalionis et al, "The molecular rationale for Src inhibition in colorectal carcinomas," Int. J. Cancer, 134:2019-2029 (2013).

Gargett, T., et al., GD2-specific CART Cells Undergo Potent Activation and Deletion Following Antigen Encounter but can be Protected From Activation-induced Cell Death by PD-1 Blockade. Mal Ther, 2016. 24(6): p. 1135-49.

Gilboa, E., "How tumors escape immune destruction and what we can do about it," Cancer Immunol. Immunother. (1999); 48: 382-385.

Gilham et al., "CAR-T cells and solid tumors: tuning T cells to challenge an inveterate foe," Trends in Molecular Medicine (2012); 18(7): 377-384 (Epub May 19, 2012).

Gilham et al., "Primary polyclonal human T lymphocytes targeted to carcino-embryonic antigens and neural cell adhesion molecule tumor antigens by CD3zeta-based chimeric immune receptors," J. Immunother, (Mar.-Apr. 2002); 25 (2): 139-151.

Gill et al., "Preclinical targeting of human acute myeloid leukemia and myeloablation using chimeric antigen receptor-modified T cells," Blood (2014); 123(15): 2343-54 (pub online Mar. 4, 2014).

Gillies, S.D. et al., "Targeting Human Cytotoxic T Lymphocytes to Kill Heterologous Epidermal Growth Factor Receptor-Bearing Tumor Cells," The Journal of Immunology (1991); 146(3): 1067-107 I.

Gong, et al., "Cancer Patient T Cells Genetically Targeted to Prostate Specific Membrane Antigen Specifically Lyse Prostate Cancer Cells and Release Cytokines in Response to Prostate-Specific Membrane Antigen," Neoplasia (1999); 1:123-7.

Gong, M. C., et al., "Prostate-specific membrane antigen (PSMA)-specific monoclonal antibodies in the treatment of prostate and other cancers," Cancer Metastasis Rev. (I 999); 18: 483-490.

Gonzalez et al., "Genetic engineering of cytolytic T lymphocytes for adoptive T-cell therapy of neuroblastoma," J Gene Med (2004); 6:704-711.

Goverman, J. et al., "Chimeric immunoglobulin-T cell receptor proteins form functional receptors: implications for T cell receptor complex formation and activation," Cell (1990); 60:929-939.

Grada et al., "TanCAR: a novel bispecific chimeric antigen receptor for cancer immunotherapy," Molecular Therapy—Nucleic Acids (2013): 2(7): Article No. e105 (internal pp. 1-11) (e-pub. Jul. 9, 2013).

Greenfield, E. A, Nguyen, K. A & Kuchroo, V. K. CD28/B7 co-stimulation: a review. Grit. Rev. Immunol. 18, 389-41 8 (1998).

Griffioen, M., et al., "Retroviral transfer of human CD20 as a suicide gene for adoptive T-cell therapy," Haematologica (2009); 94(9): 1316-20.

Griffiths et al., "The Nature of DNA" Modern Genetic Analysis. New York: W.H. Freeman; 1999, oo.1-11.

Grosenbach et al., "A recombinant vector expressing transgenes for four T-cell costimulatory molecules (OX40L, B7-1, ICAM-1, LFA-3) induces sustained CD4+ and CDS+ T-cell activation, protection from apoptosis, and enhanced cytokine production," Cellular Immunology 222 (2003) 45-57.

Gross et al., "Chimaeric T-cell receptors specific to a B-lymphoma idiotype: a model for tumour immunotherapy," Biochem. Soc. Trans. (Nov. 1995); 23(4):1079-82.

Gross et al., "Development and study of chimeric immunoglobulin/T cell receptor molecules as functional receptors that endow T cells with antibody-type specificity," Ph.D. Thesis presented to the Feinberg Graduate School, The Wiezmann Institute of Science, Rehovot, Israel (1990); 1-70.

Gross, G. et al., "Expression of immunoglobuling-T-cell receptor chimeric molecules as functional receptors with antibody-type specificity," Proc. Natl. Acad. Sci., 1989, 86, 10024-10028.

Gross, G. et al., "Generation of effector T cells expressing chimeric T cell receptor with antibody type-specificity," Transplant. Proc. (1989); 21 (I Pt 1):127-130.

Gross, G. et al., "Endowing T cells with antibody specificity using chimeric T cell receptors," Department of Chemical Immunology, FASEB J. (Dec. 1992); 6(15):3370-8.

Grupp Stephan A.: Advances in T-cell therapy for All, Best Practice & Research Clinical Haematology, vol. 27, No. 3-4, Sep. 1, 2014 (Sep. 1, 2014), pp. 222-228.

Grupp, S.A., et al., "Chimeric antigen receptor-modified T cells for acute lymphoid leukemia," N Engl J Med (2013); 368(16): 1509-18 (Epub Mar. 25, 2013).

Gruss et al., "Tumor Necrosis Factor Ligand Superfamily: Involvement in the Pathology of Malignant Lymphomas" Blood, vol. 85, No. 12, Jun. 15, 1995, pp. 3378-3404.

Guinn et al., "4-1BBL Cooperates with B7-1 and B7-2 in Converting a B Cell Lymphoma Cell Line into a Long-Lasting Antitumor Vaccine," The Journal of Immunology 162:5003-5010 (1999).

Habib-Agahi,H., Phan,T.T. and Searle,P.F. Co-stimulation with 4-1BB ligand allows extended T-cell proliferation, synergizes with CD80/CD86 and can reactivate anergic T cells Int. Immunol. 19 (12), 1383-1394 (2007).

Hackett et al. "A transposon and transposase system for human application" (2010) Molecular Therapy: The Journal of the American Society of Gene Therapy. 18:674-683.

Hansen, JD, et al., "Description of an Ectothermic TCR Coreceptor, CD8 a, in Rainbow Trout," J. Immunol., 164, 3132-3139, 2000.

Hanson, H. L. et al. Eradication of established tumors by CDS+ T cell adoptive immunotheraov. Immunity 13, 265-276 (2000).

Harper et al., "CTLA-4 and CD28 Activated Lymphocyte Molecules are Closely Related in Both Mouse and Human as to Sequence, Message, Expression, Gene Structure, and Chromosomal Location", The Journal of Immunology, vol. 147, 1037-1044, No. 3, Aug. 1, 1991.

Hatakeyama et al., "Transmembrane Signaling of Interleukin 2 Receptor," J. Exp. Med. 1987, vol. 166 pp. 362-375.

Haynes, N. M., et al., "Redirecting mouse CTL against colon carcinoma: superior signaling efficacy of single chain variable domain chimeras containing TCR-vs FcERI-y," J. Immunol. (2001); 166: 182-187.

Haynes, Nicole M., Marie B. Snook, Joseph A. Trapani, Loretta Cerruti, Stephen M. Jane, Mark J. Smyth and Philip K. Darcy "Redirecting Mouse CTL Against Colon Carcinoma: Superior Sig-

(56) References Cited

OTHER PUBLICATIONS naling Efficacy of Single-Chain Variable Domain Chimeras Containing TCR-zeta vs Fcepsi/onRI-gamma" *J Immunol 2001*; 166:182-187 (Haynes 2001).
Hege et al., "Systemic T Cell-independent Tumor Immunity after Transplantation of Universal Receptor-modified Bone Marrow into SCIO Mice", J. Exp. Med. vol. 184 Dec. 1996 oo. 2261-2269.
Hege et al., "Safety, tumor trafficking and immunogenicity of chimeric antigen receptor (CAR)-T cells specific for TAG-72 in colorectal cancer," Journal for ImmunoTherapy of Cancer 2017, 5:22.
Hekele, A. et al., "Growth retardation of tumors by adoptive transfer of cytotoxic T lymphocytes reprogrammed by CD44v6-specific scFv:zeta-chimera," Int. J. Cancer (1996); 68(2):232-8.
Herron, J.N., et al., High resolution structures of the 4-4-20 Fab-fluorescein complex in two solvent systems: effects of solvent on structure and antigen-binding affinity. Biophys J, 1994. 67(6): p. 2167-83.
Heslop, "Genetic engineering of T-cell receptors: TCR takes to titin," Blood (Aug. 8, 2013); 122(6):853-4.
Heslop, H.E., "Safer CARS," Mol Ther (2010); 18(4): p. 661-2.
Heuser, et al., "T-cell activation by recombinant immunoreceptors: impact of the intracellular signalling domain on the stability of receptor expression and antigen-specific activation of grafted T-cells," Gene Therapy (2003); 10: 1408-1419.
Ho, et al., "Adoptive Immunotherapy: Engineering T Cell Responses as Biologic Weapons for Tumor Mass Destruction," Cancer Cell (May 2003); 3:431-7.
Hombach et al., "T cell activation by recombinant FcERI y-chain immune receptors: an extracellular spacer domain impairs antigen-dependent T cell activation but not antigen recognition," Gene Therapy (2000) 7, 1067-1075.
Hombach, et al., "Adoptive Immunotherapy with Genetically Engineered T Cells: Modification of the IgGI Fe 'Spacer' Domain in the Extracellular Moiety of Chimeric Antigen Receptors Avoids 'Off-Target' Activation and Unintended Initiation ofan Innate Immune Response," Gene Ther. (Oct. 2010); 17(10):1206-13.
Huang, J., et al., Modulation by IL-2 of CD70 and CD27 expression on CDS+ T cells: importance for the therapeutic effectiveness of cell transfer immunotherapy J. Immunol. 176 (12), 7726-7735 (2006).
Hudecek, M., et al., "Receptor affinity and extracellular domain modifications affect tumor recognition by RORI-specific chimeric antigen receptor T cells," Clin Cancer Res (2013); 19(12): 3153-64 (Published Online First Apr. 25, 2013).
Hughes M. S. et al., Transfer of a TCR gene derived from a patient with a marked antitumor response conveys highly active T-cell effector functions. Hum Gene Ther Apr. 2005; 16(4):457-72).
Hunter et al., "Inhibition of Fey Receptor-Mediated Phagocytosis by a Nonphagocytic Fey Receptor," Blood, vol. 91, No. 5 (Mar. 1, 1998): pp. 1762-1768.
Hutchins, B. et al., "Site-specific coupling and sterically controlled formation of multimeric antibody fab fragments with unnatural amino acids," J. Mol. Biol., 2011, 406, 595-603.
Hutloff. A. et al., "ICOS is an inducible T-cell costimulator stmcturally and functionally related to CD28," Nature. 1999, 397, 263-266.
Hwu, et al., "The Genetic Modification of T Cells for Cancer Therapy: An Overview of Laboratory and Clinical Trials," Cancer Detection and Prevention (1994); 18(1):43-50.
Hwu, P., et al., "In Vivo Antitumor Activity of T Cells Redirected with Chimeric Antibody/T-Cell Receptor Genes," Cancer Research (Aug. 1, 1995); 55: 3369-3373.
Hwu, P. et al., "Lysis of Ovarian Cancer Cells by Human Lymphocytes Redirected with a Chimeric Gene Composed of an Antibody Variable Region and the Fe Receptor gamma-Chain," The Journal of Experimental Medicine (1993); 178, 361-366.
Imai, C. et al., "Chimeric receptors with 4-IBB signaling capacity provoke potent cytotoxicity against acute lymphoblastic leukemia," Leukemia. 2004, 18, 676-684.

Imai, K., et al., "Comparing Antibody and Small-Molecule Therapies for Cancer"; https://www.medscage.com/viewarticle/550008 (26 pages).
International Search Report for PCT/US2013/076986, dated Apr. 28, 2014.
Irving, B. A., et al., "The cytoplasmic domain of the T cell receptor zeta chain is sufficient to couple to receptor-associated signal transduction pathways" Cell (1991); 64:891-90 I.
Israeli, R. S., et al., "Expression of the prostate-specific membrane antigen," Cancer Res. (1994); 54, 1807-1811.
Janeway et al., "Appendix I. Immunologists' Toolbox" Immunobiology: The Immune System in Health and Disease. 5th ed. New York: Garland Science; 2001 (101 pages).
Janeway et al., "The structure of a typical antibody molecule" Immunobiology: The Immune System in Health and Disease. 5th Ed. New York: Garland Science; 2001, pp. 1-11.
Jang, I, et al., "Human 4-188 (CD137) Signals Are Mediated by TRAF2 and Activate Nuclear Factor-kB," Biochemical And Biophysical Research Communications (1998); 613-620.
Jena et al., "Redirecting T-cell specificity by introducing a tumor-specific chimeric antigen Receptor," Blood 2010, vol. 116, No. 7, pp. 1035-1044.
Jensen, M et al. "CD20 Is A Molecular Target For scFvFc[zeta] Receptor Redirected T Cells: Implications for Cellular Immunotherapy of CD20+ Malignancy," Biology of Blood and Marrow Transplantation (1998); 4:75-83.
Jensen, M. C., et al., Abstract #98: "Targeting Pre-B Acute Lymphoblastic Leukemia With T Cell Clones Engineered To Express A CDJ9-Specific Chimeric Immunoreceptor," Blood (Nov. 16, 2000); 96(1 I):26A.
Jensen, M. C., et al., "Human T lymphocyte genetic modification with naked DNA," Molecular Therapy (2000); 1:49-55.
Jensen, M.C., et al., Antitransgene rejection responses contribute to attenuated persistence of adoptively transferred CD20/CD1 9-specific chimeric antigen receptor redirected T cells in humans. Biol Blood Marrow Transplant, 2010. 16(9): p. 1245-56.
Johnson, L.A., et al., "Gene therapy with human and mouse T-cell receptors mediates cancer regression and targets normal tissues expressing cognate antigen," Blood (2009); 114(3):535-546.
Jonnalagadda et al., "Chimeric Antigen Receptors With Mutated IgG4 Fe Spacer Avoid Fc Receptor Binding and Improve T Cell Persistence and Antitumor Efficacy," Molecular Therapy 2015, vol. 23, No. 4, DD. 757-768.
Jung S, Pluckthun A. "Improving in vivo folding and stability of a single-chain Fv antibody fragment by loop grafting." Protein Eng. Aug. 1997; I0(8):959-66.
Jung, S. et al., "Selection for improved protein stability by phage display," J. Mol. Biol., 1999, 294, 163-180.
Junghans RP, "Is it safer CARs that we need, or safer rules of the road?," Mol Ther. (Oct. 2010); 18(10):1742-3.
Kagoya, Y., et al., Transient stimulation expands superior antitumor T cells for adoptive theraov. JCI Insight, 2017. 2(2): p. e89580 (13 pages).
Kalos, M., et al., "T cells with chimeric antigen receptors have potent antitumor effects and can establish memory in patients with advanced leukemia," Sci Transl Med (2011); 3(95): 95ra73 (13 pages).
Kandalaft, L. et al., "A phase I clinical trial of adoptive transfer of folate receptor-alpha redirected autologous T cells for recurrent ovarian cancer," Journal of Translational Medicine, 2012, 10. 157-167.
Kang, S. et al: "Therapeutic uses of anti-interleukin-6 receptor antibody", International Immunology, vol. 27, No. I, Aug. 20, 2014 (Aug. 20, 2014), pp. 21-29.
Karachaliou et al., "Common Co-activation of AXL and CDCP1 in EGFR-mutation-positive Non-smallcell Lung Cancer Associated with Poor Prognosis," EBioMedicine (2017) https://doi.org/10/1016/i.ebiom.2018.02.001.
Kariv et al., Analysis of the Site of Interaction of CD28 with Its Counterreceptors CD80 and CD86 and Correlation with Function, 157 J. Immunol.29-38 (1996).

(56) References Cited

OTHER PUBLICATIONS

Katz et al., "Recognition of HLA-Cw4 but Not HLA-Cw6 by the NK Cell Receptor Killer Cell Ig-Like Receptor Two-Domain Short Tail No. 4", J Immunol 2001; 166:7260-7267.
Kenderian, et al; CD33-specific chimeric antigen receptor T cells exhibit potent preclinical activity against human.
Kennedy, M. et al., "Optical imaging of metastatic tumors using a folate-targeted fluorescent probe," J. Biomed. Opt., 2003, 8, 636-641.
Kershaw, et al., "A phase I study on adoptive immunotherapy using gene-modified T cells for ovarian cancer," Clin. Cancer Res. (2006); 12: 6106-6115.
Kershaw, M.H. et al., "Gene-Engineered T Cells as a Superior Adjuvant Therapy for Metastatic Cancer," The Journal ofImmunology (2004); 173: 2143-2150.
Kim et al., "Protein conjugation with genetically encoded unnatural amino acids," Curr Opin Chem Biol (2013); 17:412-419 (Epub May 9, 2013).
Kim et al., "Therapeutic Potential of 4-1BB (CD137} As a Regulator for Effector CDS.. T Cells," Journal of Hematotherapy & Stem Cell Research (2001) 10:441-449.
Kim, M. et al, "Redirection of Genetically Engineered CAR-T cells Using Bifunctional Small Molecules," J. Am. Chem. Soc., 2015, 137, 2832-2835.
Kintzing et al., "Emerging Strategies for Developing Next-Generation Protein Therapeutics for Cancer Treatment" Trends in Pharmacological Sciences, vol. 37, No. 12, Dec. 2016, pp. 993-1008.
Klotz et al., "Macromolecule-Small Molecule Interactions. Strong Binding by Intramolecularly Cross-Linked Polylysine" Biochemistry. vol. 10, No. 6, Mar. 16, 1971, DD.923-926.
Kochenderfer et al., "Construction and pre-clinical evaluation of an anti-CD19 chimeric antigen receptor," Journal of Immunotherapy (2009); 32(7): 689-702.
Kochenderfer et al., "Treating B-cell cancer with T cells expressing anti-CD19 chimeric antigen receptors" 2013, Nature Reviews Clinical Oncology, 10, 267-276 (2013).
Kochenderfer, J. et al., "B-cell depletion and remissions of malignancy along with cytokine- associated toxicity in a clinical trial of anti-CDI 9 chimeric-antigen—receptor—transduced T cells," Blood, 2012, 119, 2709-2720.
Kochenderfer, J.N., et al., "Adoptive transfer of syngeneic T cells transduced with a chimeric antigen receptor that recognizes murine CD19 can eradicate lymphoma and normal B cells.," Blood (2010); 116(19):3875-86.
Kochenderfer, J. et al., "Eradication of B-lineage cells and regression of lymphoma in a patient treated with autologous T cells genetically engineered to recognize CD19," Blood, 2010, 116, 4099-4102.
Kolmar. H. et al., "Alternative binding proteins: biological activity and therapeutic potential of cystine-knot miniproteins." The FEBS Journal, 2008, 275, 26684-26690.
Kowolik, et al., "CD28 Costimulation Provided through a CD19-Specific Chimeric Antigen Receptor Enhances In vivo Persistence and Antitumor Efficacy of Adoptively Transferred T Cells," Cancer Research (Nov. 15, 2006); 66(22): 10995-11004.
Kowolik, et al., "CD28-costimulation provided through a CD-19-specific chimeric immunoreceptor enhances in vivo persistence and anti-tumor efficacy of adoptively transferred T cells," Blood (2005); 106(11): 1278 (Retrieved from http://www.bloodjournal.org/contenU106/11/1278).
Kozak, M, "At least six nucleotides preceding the AUG initiator codon enhance translation in mammalian cells," J. Mal. Biol., 196, 947-50, 1987.
Kozak, M, "At least six nucleotides preceding the AUG initiator codon enhance translation in mammalian cells," J. Mol.
Krause, et al., "Antigen-dependent CD28 Signaling Selectively Enhances Survival and Proliferation in Genetically Modified Activated Human Primary T Lymphocytes," J. Exp. Med. (1998); 188: 619-26.

Krause, A., et al., "Genetic approaches to sustain the function of tumor-specific T-lymphocytes," Mol. Ther. (2000); I (S260): 713.
Kularatne, S.A. et al., "Prostate-specific membrane antigen targeted imaging and therapy of prostate cancer using a PSMA inhibitor as a homing ligand," Mal. Pharm., 2009, 6,780-789.
Kuwana, Y. et al., "Expression of chimeric receptor composed of immunoglobulin-derived V regions and T- cell receptor-derived C regions," Biochem. Biophys. Res. Comm. (1987); 149:960-968.
Kwon, 8, et al., "cDNA sequences of two inducible T-cell genes," (1989); 86: 1963-1967.
Kwon, B, et al., "Expression Characteristics of Two Potential T Cell Mediator Genes," Cellular Immunology (1989); 414-422.
Lafage-Pochitaloff M, Costello R, Couez D, Simonetti J, Mannoni P, Mawas C, Olive D. "Human CD28 and CTLA-4 Ig superfamily genes are located on chromosome 2 at bands q33-q34" Immunogenetics 1190;31(3):198-201.
Lamers et al., "Immune responses to transgene and retroviral vector in patients treated with ex vivo-engineered T cells," Blood (2011) 117(1): 72-82.
Lamers, C. et al., "Treatment of Metastatic Renal Cell Carcinoma With Autologous T-Lymphocytes Genetically Retargeted Against Carbonic Anhydrase IX: First Clinical Experience," J. Clin. Oneal., 2006, 24, e20-22.
Lamers, C.H., et al., "Immune responses to transgene and retroviral vector in patients treated with ex vivo-engineered T cells," Blood (2011); 117(1): 72-82.
Laroche et al., "Characterization of a Recombinant Single-chain Molecule Comprising the Variable Domains of a Monoclonal Antibody Specific for Human Fibrin Fragment O-dimer*," The Journal of Biological Chemistry 1991, vol. 266, No. 25, Issue of Sep. 5, pp. 16343-16349.
Latza, U. et al., "The human OX40 homolog: cDNA structure, expression and chromosomal assignment of the ACT35 antigen," Eur. J. Immunol., 1994, 24, 677-683.
Lee, D, et al., "4-188 Signaling Activates the T Cell Factor 1 Effector/b-Catenin Pathway with Delayed Kinetics via ERK Signaling and Delayed PI3K/AKT Activation to Promote the Proliferation of CDS+T Cells," PLOS One (2013); 8: 1-11.
Lee, Blood 2015 126:1048. Erratum to Lee D. W. et al: "Current concepts in the diagnosis and management of cytokine release syndrome" Blood. Jul. 10, 2014;124(2): 188-95. doi: 10.1182/blood-2014-05-552729. Epub May 29, 2014.
Lee, Blood 2016 128:1533 Erratum to Lee D. W. et al: "Current concepts in the diagnosis and management of cytokine release syndrome" Blood. Jul. 10, 2014;124(2): 188-95. doi: 10.1182/blood-2014-05-552729. Epub May 29, 2014.
Leed. W. et al: "Current concepts in the diagnosis and management of cytokine release syndrome" Blood. Jul. 10, 2014;124(2) :188-95. doi: 10.1182/blood-2014-05-552729. Epub May 29, 2014.
Letourneur et al. "T-cell and basophil activation through the cytoplasmic tail of T-cell-receptor zeta family proteins" Proc. Natl. Acad. Sci USA (1991); 88:8905-8909.
Liebowitz, D. N., Lee, K. P. & June, C. H. Co-stimulatory approaches to adoptive immunotherapy. Curr. Opin. Oneal. 10, 533-541 (1998).
Lin et al., "Transglutaminase-catalyzed site-specific conjugation of small-molecule probes to proteins in vitro and on the surface of living cells," J. Am. Chem. Soc. (2006); 128:4542-4543.
Linenberger, "CD33-directed therapy with gemtuzumab ozogamicin in acute myeloid leukemia: progress in understanding cytotoxicity and potential mechanisms of drug resistance", Leukemia (2005) 19, 176-182.
Linette, G.P., et al., "Cardiovascular toxicity and titin cross-reactivity of affinity-enhanced T cells in myeloma and melanoma," Blood (Aug. 8, 2013); 122(6): 863-71 (Epub Jun. 14, 2013).
Liou et al., A chimeric mouse-human antibody that retains specificity for HIV gp 120 and mediates the I sis of HIV-infected cells,. J Immunol 1989; 143: 3967-3975.
Liu, H. et al., "Monoclonal antibodies to the extracellular domain of prostate-specific membrane antigen also react with tumor vascular endothelium," Cancer Res. (1997); 57: 3629-3634.
Lodish et al., "Hierarchical Structure of Proteins" Molecular Cell Biology. 4th Ed. New York: W.H. Freeman; 2000. pp. 1-25.

(56) References Cited

OTHER PUBLICATIONS

Long, A.H., et al., 4-IBB costimulation ameliorates T cell exhaustion induced by tonic signaling of chimeric antigen receptors. Nat Med, 2015. 21(6): p. 581-90.
Love et al., "ITAM-mediated Signaling by the T-Cell Antigen Receptor", Cold Spring Harb Perspect Biol 2010;2:a002485.
Lowin-Kropf et al., "Cytoskeletal Polarization of T Cells Is Regulated by an Immunoreceptor Tyrosine-based Activation Motif-dependent Mechanism," The Journal of Cell Biology 1998, vol. 140, No. 4, pp. 861-871.
Isakov et al., "PKG-theta-mediated signal delivery from the TCR/CD28 surface receptors", Frontiers in Immunology, T Cell Biology, Aug. 2012, vol. 3, Article 273, pp. 1-12.
Lu, Y. et al., "Preclinical pharmacokinetics, tissue distribution, and antitumor activity of a folate-hapten conjugate-targeted immunotheraphy in hapten-immunized mice," Molecular Cancer Therapeutics, 2006, 5, 3258-3267.
Lu, Y. et al., Preclinical pharmacokinetics, tissue distribution, and antitumor activity of a folate-hapten conjugate-targeted immunotherapy in hapten-immunized mice, Molecular Cancer Therapeutics, 2006, vol. 5, No. 12, pp. 3258-3267.
Lu, Y., et al., "Strategy to prevent drug-related hypersensitivity in folate-targeted hapten immunotherapy of cancer," AAPS J (2009); 11(3): 628-38.
Lu, Y. et al., "Folate-targeted dinitrophenyl hapten immunotherapy: effect of linker chemistry on antitumor activity and allergic potential," Mol. Pharm., 2007, 4, 695-706.
Lu, Y. et al., "Palate-targeted dinitrophenyl hapten immunotherapy: effect of linker chemistry on antitumor activity and allergic potential," Mal. Pharm., 2007, 4, 695-706.
Lueders et al., "The Long Terminal Repeat of an Endogenous Intracisternal A-Particle Gene Functions as a Promoter When Introduced into Eucaryotic Cells by Transfection" Molecular and Cellular Biology, vol. 4, No. 10, Oct. 1984, pp. 2128-2135.
Lustgarten, J., et al., "Specific Elimination of IgE Production Using T Cell Lines Expressing Chimeric T Cell Receptor Genes," European Journal of Immunology (1995); 25(10):2985-2991.
Ma, Y., et al., "Targeting of antigens to B lymphocytes via CD19 as a means for tumor vaccine development," J Immunol (2013); 190: 5588-99 (Prepublished online Apr. 29, 2013).
Ma, J. et al., "Versatile strategy for controlling the specificity and activity of engineered T cells," Proc. Natl. Acad. Sci., 2016, 113, E450-458.
Ma, Q. et al., "Carcinoembryonic antigen-immunoglobulin Fe fusion protein (CEA-Fe) for identification and activation of anti-CEA immunoglobulin-T-cell receptor-modified T cells, representative of a new class of Ig fusion proteins," Cancer Gene Therapy (2004); 11: 297-306.
Ma, Q., et al., "Genetically engineered T cells as adoptive immunotherapy of cancer," Cancer Chemother Biol Response Modif(2002); 20: 315-41.
Maher, et al., "Human T-lymphocyte cytotoxicity and proliferation TCRzeta/CD28 receptor," Nature Biotechnology (2002); 20: 70-75.
Maher, J., "Immunotherapy of malignant disease using chimeric antigen receptor engrafted T cells," ISRN Oneal (2012); Article ID 278093, 23 pages (Epub Dec. 9, 2012).
Manual pCDH Vectors (System Biosciences) (21 pages).
Marincola, F. M., et al., "Escape of human solid tumors from T cell recognition: molecular mechanisms and functional significance," Adv. Immunol. (2000); 74: 181-273.
Maude Shannon L. et al. "Chimeric Antigen Receptor T Cells for Sustained Remissions in Leukemia" N Engl J Med. Oct. 16, 2014;371(16):1507-17.
Maude Shannon L. et al. "Managing Cytokine Release Syndrome Associated With Novel T Cell-Engaging Therapies" Cancer J. Mar.-Apr. 2014;20(2):119-22.
Maus et al., "Ex vivo expansion of polyclonal and antigen-specific cytotoxic T lymphocytes by artificial APCs expressing ligands for the T-cell receptor, CD28 and 4-1BB," Nature Biotechnology, Nature Publishing Group, New York, NY, US, vol. 20, No. 2, Feb. 1, 2002, pp. 143-148.
Maus, et al., "Zoom Zoom: racing CARs for multiple myeloma," Clin Cancer Res. (Apr. 15, 2013); 19(8): 1917-9 (Epub Feb. 26, 2013).
Maus, M.V., et al., T cells expressing chimeric antigen receptors can cause anaphylaxis in humans. Cancer Immunol Res, 2013. 1(1): p. 26-31.
Mcguinness RP, et al., "Anti-tumor activity of human T cells expressing the CC49-zeta chimeric immune receptor," Hum Gene Ther. (Jan. 20, 1999); 10(2): 165-73.
Medstrand et al., "Long Terminal Repeats Are Used as Alternative Promoters for the Endothelin B Receptor and Apolipoprotein C-1 Genes in Humans", The Journal of Biological Chemistry, vol. 276, No. 3, Issue of Jan. 19, pp. 1896-1903, 2001.
Melero, I, et al., "Amplification of tumor immunity by gene transfer of the co-stimulatory 4-188 ligand: synergy with the CD28 co-stimulatory pathway," Bristol-Myers Squibb Pharmaceutical Research Institute (1998); 1116-1121.
Melief, C. J. et al., "Strategies for immunotherapy of cancer," Adv. Immunol. (2000); 75:235-282.
Midelfort, KS, et al., "Substantial Energetic Improvement with Minimal Structural Perturbation in a High Affinity Mutant Antibody," J. Mal. Biol., 343, 685-701, 2004.
Milone MC, et al., "Chimeric receptors containing CD 137 signal transduction domains mediate enhanced survival of T cells and increased antileukemic efficacy in vivo," Mol Ther. (Aug. 2009); 17(8):1453-64.
Mooney et al., "Concise Review: Neural Stem Cell-Mediated Targeted Cancer Therapies" Stem Cells Translational Medicine, 2018, pp. 740-747.
Moore et al., "Characterisation of salmon and trout CD8a and CD8I3," Molecular Immunology 42 (2005) 1225-1234.
Moore, P.A., et al., "Application of dual affinity retargeting molecules to achieve optimal redirected T-cell killing of B-cell lymphoma," Blood (2011); 117(17): 4542-51.
Moretta et al., "Activating Receptors and Coreceptors Involved in Human Natural Killer Cell-Mediated Cytolysis." Annu. Rev. Immunol. 2001. 19:197-223.
Morgan et al., "Case report of a serious adverse event following the administration of T cells transduced with a chimeric antigen receptor recognizing ERBB2," Mol. Ther. (2010); 18: 843-851.
Morgan RA, et al., "Cancer regression in patients after transfer of genetically engineered lymphocytes," Science (Oct. 6, 2006); 3I 4(5796): 126-9.
Morgan, RA, et al., "Case Report of a Serious Adverse Event Following the Administration of T Cells Transduced With a Chimeric Antigen Receptor Recognizing ERBB2," Mal. Therapy, 18(4), 843-851, 2010.
Non-Final Office Action issued by The United States Patent and Trademark Office for U.S. Appl. No. 15/296,666, dated Jul. 27, 2017, 6 pages.
Morgan, RA, et al., "Case Report of a Serious Adverse Event Following the Administration of T Cells Transduced with a Chimeric Antigen Receptor Recognizing ERBB2," Mol. Therapy, 18(4), 843-851, 2010.
Moritz, D. et al., "Cytotoxic T lymphocytes with a grafted recognition specificity for ERBB2-expressing tumor cells,".
Morrison, C, "CAR-T Field Booms as Next-Generation Platforms Attract Big Players," Nature Biotechnology (Jun. 2015); 33: 571-72.
Muller T, et al., "Expression of a CD20-specific chimeric antigen receptor enhances cytotoxic activity ofNK cells and overcomes NK-resistance of lymphoma and leukemia cells," Cancer Immunol. Immunother. (2008); 57: 411-423.
Mungra et al., "Targeted human cytolytic fusion proteins at the cutting edge: harnessing the apoptosis-inducing properties of human enzymes for the selective elimination of tumor cells" Oncotarget, vol. 10, No. 8, 2019, pp. 897-915.
Munn et al., "Role of Low-Affinity Fe Receptors in Antibody-dependent Tumor Cell Phagocytosis by Human Monocvte-derived Macrophages," Cancer Research 51, 1117-1123, Feb. 15, 1991.

(56) References Cited

OTHER PUBLICATIONS

Nam, K, et al., "Cross-Linking of 4-1BB Activates TCR-Signaling Pathways in CD8 T Lymphocytes1," The Journal of Immunology; 1898-1905.

National Cancer Institute. CAR T-Cell Therapy: Engineering Patients' Immune Cells to Treat Their Cancers, Cancer Research Updates, Updated: Oct. 16, 2014; 5 pages; retrieved Nov. 17, 2014 from http://www.cancer.gov/cancertopics/research-updates/2013/CAR-T-Cells.

Nelson, Aaron L., "Antibody fragments," mAbs 2010, Landes Bioscience, vol. 2, Issue 1, pp. 77-83.

Nieba, L. et al., "Disrupting the hydrophobic patches at the antibody variable/constant domain interface: improved in vivo folding and physical characterization of an engineered scFv fragment," Protein Eng., 1997, 10, 435-444.

Oelke et al., "Ex vivo induction and expansion of antigen-specific cytotoxic T cells by HLA-Ig-coated artificial antigen- presenting cells," Nature Medicine (2003); 9(5):619-624.

Oelsner, S., et al., "Continuously expanding CAR NK-92 cells display selective cytotoxicity against B-cell leukemia and lymphoma", Cytotherapy, 2017; 19: 235-249.

Okazaki et al., "PD-I immunoreceptor inhibits B cell receptormediated signaling by recruiting src homology 2-domain-containing tyrosine phosphatase 2 to phosphotyrosine", PNAS Nov. 20, 2001, vol. 98, No. 24, 13866-13871.

Orr, B et al., "Rapid method for measuring ScFv thermal stability by yeast surface display," Biotechnol Prag., 2003. 19, 631-638.

Pages et al., "Two Distinct Intracytoplasmic Regions of the T-cell Adhesion Molecule CD28 Participate in Phosphatidylinositol 3-Kinase Association" The Journal of Biological Chemistry, vol. 271, No. 16, Apr. 19, 1996, pp. 9403-9409.

Paillard, F. "Immunotherapy with T cells bearing chimeric antitumor receptors," Hum. Gene Ther. (1999); 10: 151-153.

Paillasse, M, et al., "Insights into the Cholecystokinin 2 Receptor Binding Site and Processes of Activation," The American Society for Pharmacology and Experimental Therapeutics (2006); 70:1935-1945.

Pameijer, C.R., et al., "Conversion of a tumor-binding peptide identified by phage display to a functional chimeric T cell antigen receptor," Cancer Gene Ther., 2007, 14, 91-97.

Park et al., "Treating cancer with genetically engineered T cells" Trends Biotechnol. Nov. 29, 2011(11): 550-557.

Parkhurst et al. "Characterization of genetically modified T-cell receptors that recognize the CEA:691-699 peptide in the context of HLA-A2.1 on human colorectal cancer cells" (2009) Clin Cancer Res. Jan. 1, 2009;15(1):169-80.

Patel et al., "T -cell killing of heterogenous tumor or viral targets with bispecific chimeric immune receptors," Cancer Gene Therapy (2000); 7(8): 1127-1134.

Patel Jaina M et al: "Cancer CARtography: charting out a new approach to cancer immunotheraDv", Immunotherapy. 2014;6(6):675-8.

Peprotech, Recombinant Human 4-1BB Receptor, https://www.peprotech.com/recombinant-human-4-1bb-receptor, downloaded Jul. 25, 2018.

Pierce, et al., "Computational Design of the Affinity and Specificity of a Therapeutic T Cell Receptor" PLOS Computational Biology (Feb. 13, 2014); 10(2): e1003478 (11 pages).

Pinto, RD, et al., "Molecular cloning and characterization of sea bass (*Dicentrarchus labrax* L.) CD8a," Veterinary Immunology and Immunopathology, 110, 169-177, 2006.

Pizarro, J.C., et al., "Structural and functional characterization of a monoclonal antibody specific for the preSI region of hepatitis B virus," FEBS letters (2001); 509: 463-468.

Pochitaloff et al., "Human CD28 and CTLA-4 Ig superfamily genes are located on chromosome 2 at bands q33-Q34," Abstract. Immunoaenetics 1990; 31(3): 198-201.

Pollock et al., Inducible T cell antigen 4-1BB. Analysis of expression and function, J Immunol1993; 150:771-781.

Porter DL, et al. "Chimeric antigen receptor T cells persist and induce sustained remissions in relapsed refractory chronic lymphocytic leukemia". Science translational medicine. 2015;7(303):303-39. doi: 10. I 126/scitranslmed.aac5415. PubMed PMID: 26333935.

Porter, D.L. et al., "Chimeric antigen receptor-modified T cells in chronic lymphoid leukemia," N. Engl. J. Med., 2011, 365, 725-733.

Prasad et al., "T-cell antigen CD28 interacts with the lipid kinase phosphatidylinositol 3-kinase by a cytoplasmic Tyr(P)-Met-Xaa-Met motif", Proc. Natl. Acad. Sci. USA, vol. 91, pp. 2834-2838, Mar. 1994.

Product brochure for the Engineered Autologous Cell Therapy (eACT™) Platform, available from Kite Pharma, retrieved Oct. 25, 2015 from http://www.kitepharma.com/c/products/eact.php.

Protein Lounge, 4-1BB Pathway, http://www.proteinlounge.com/Pathway/4-1BB%20Pathway, downloaded Jul. 25, 2018.

Qin et al., "Incorporation of a hinge domain improves the expansion of chimeric antigen receptor T cells," Journal of Hematoloi:,y & Oncology (2017) 10:68.

Rabu, C, et al., "Production of Recombinant Human Trimeric CD137L (4-IBBL) Cross-Linking Is Essential To Its T Cell Costimulation Activity," J. Biol. Chem, 280(50), 41472-41481, 2005.

Rader, "DARTs take aim at BiTEs," Blood (Apr. 28, 2011); 117(17):4403-4.

Rai et al., "Expression systems for production of heterologous proteins," Current Science 2001, vol. 80, No. 9, DD. 1121-1128.

Receptors, NK Cell Lectin-Like MeSH Descriptor Data 2018, NIH U.S. National Library of Medicine, Jul. 25, 2018.

Reddy et al., "Elimination of Fe Receptor-Dependent Effector Functions of a Modified IgG4 Monoclonal Antibody to Human CD4," J Immunol 2000; 164: 1925-1933.

Redmond et al., "The role of OX40-mediated co-stimulation in T cell activation and survival," Grit. Rev. Immunol. 2009, 29(3): 187-201.

Reichert, J. "Day 1, Emerging Disruptive Technologies and Cutting-Edge Analytical Techniques," MAbs, 2009, 1, 190-209.

Restifo, N.P., et al., "Adoptive immunotherapy for cancer: harnessing the T cell response," Nat Rev Immunol (Mar. 22, 2012); 12(4): 269-81.

Reubi, Jean Claude, "Peptide Receptors as Molecular Targets for Cancer Diagnosis and Therapy," Endocrine Reviews 24(4): 389-427.

Riha et al., "CD28 co-signaling in the adaptive immune response" Self/Nonself 1:3, 231-240; July/Aug./Sep. 2010.

Riley et al., "The CD28 family: a T-cell rheostat for therapeutic control of T-cell activation", Blood, Jan. 1, 2005, vol. 105, No. 1, DD. 13-21.

Riviere, I., Gallardo, H.F., Hagani, AB. & Sadelain, M. Retroviral-mediated gene transfer in primary murine and human T-lymphocytes. Mal. Biotechnol. 15, 133-142 (2000).

Roberts et al., "Chemistry for peptide and protein PEGylation," Advanced Drug Delivery Reviews (2002); 54:459-476.

Roberts, et al., "Antigen-specific cytolysis by neutrophils and NK cells expressing chimeric immune receptors bearing zeta or gamma signaling domains," J. Immunol. (1998); 161:375-84.

Rodgers, D. et al., "Switch-mediated activation and retargeting of CAR-T cells for B-cell malignancies," Proc. Natl. Acad. Sci., 2016, 113, E459-468.

Rombach, et al., J Immunol (2004); 173: 695: (Erratum to Rombach, et al., Tumor-specific T cell activation by recombinant immunoreceptors: CD3 zeta signaling and CD28 costimulation are simultaneously required for efficient IL-.

Rombach, et al., "Tumor-specific T cell activation by recombinant immunoreceptors: CD3 zeta signaling and CD28 costimulation are simultaneously required for efficient IL-2 secretion and can be integrated into one combined CD28/CD3 zeta signaling receptor molecule," J Immunol. (2001); 167:6123-31.

Romeo, C. at al., "Sequence requirements for induction of cytolysis by the T cell antigen/Fe receptor zeta chain," Cell (1992); 68:889-897.

Romeo, C., et al., "Cellular immunity to HIV activated by CD4 fused to T cell or Fe receptor polypeptides," Cell (1991); 64:1037-1046.

(56) References Cited

OTHER PUBLICATIONS

Rosenberg "Cell transfer immunotherapy for metastatic solid cancer—what clinicians need to know" (2011) Nat Rev Clin Oneal. 8(10):577-85).
Rosenberg SA, Restifo N P, Yang JC, Morgan RA, Dudley M E. Adoptive cell transfer: a clinical path to effective cancer immunotherapy. Nat Rev Cancer. Apr. 2008; 8(4):299-308.
Rosenberg, S. A. et al., "Adoptive cell therapy for the treatment of patients with metastatic melanoma," Current Opinion in Immunology, 2009, 21, 233-240.
Rossi, et al., "2730 Phase 1 Biomarker Analysis of the ZUMA-1 (KTE-CI9-101) Study: A Phase 1-2 Multi-Center Study Evaluating the Safety and Efficacy of Anti-CD19 CART Cells (KTEC19) in Subjects with Refractory Aggressive Non-Hodgkin Lymphoma (NHL)," American Society of Hematology (2015) (https://ash.confex.com/ash/2015/webprogramscheduler/Paper80339.html) (2 pages) (presentation date Dec. 6, 2015).
Rotz Seth J. et al. "Severe cytokine release syndrome in a patient receiving PD-1-directed therapy" Pediatr Blood Cancer. Dec. 2017;64(12). Epub May 24, 2017 (4 pages).
Rueckert et al., "A monoclonal antibody as an effective therapeutic agent in breast cancer: trastuzumab" Expert Opin Biol Ther. Jun. 2005;5(6):853-66.
Sadelain et al., "Targeting Tumours with Genetically Enhanced T Lymphocytes," Nat Rev Cancer (Jan. 2003); 3( I): 35-45.
Sadelain, et al., "The promise and potential pitfalls of chimeric antigen receptors," Current Opinion in Immunology (2009); 21: 215-223.
Sadelain, M et al., . . . The basic principles of chimeric antigen receptor design, Cancer Discov., 2013, 3. 388-398.
Saoulli, C, et al., "CD28-independent, TRAF2-dependent Costimnlation of Resting T Cells by 4-188 LiQand," Department of Immunology University of Toronto (1998); 1-67.
Saraswat et al., "DNA as Therapeutics; an Update," Indian J Pharm Sci. Sep.-Oct. 2009;71(5): 488-498.
Scholler, J., et al., "Decade-long safety and function of retroviral-modified chimeric antigen receptor T cells," Sci Transl Med (May 2, 2012); 4(132): 132ra53 (7 pages).
Schonfeld, K, et al., "Selective Inhibition of Tumor Growth by Clonal NK Cells Expressing an Erb82/HER2-Specific Chimeric Antigen Receptor", Mal. Ther., vol. 23 No. 2, 330-338 Feb. 2015.
Schreiber, S.L., "Organic synthesis toward small-molecule probes and drugs" PNAS, vol. 108, No. 17, Apr. 26, 2011, pp. 6699-6702.
Schutsky, K, et al., "Rigorous optimization and validation of potent RNA CAR T cell therapy for the treatment of common epithelial cancers expressing folate receptor," Oncotarget (Oct. 6, 2015); 6(30):28911-28.
Scott, D., et al., "Immunogenicity of biotinylated hapten-avidin complexes," Mol Immunol (1984); 21(11): 1055-60.
Sega, E. et al., "Tumor detection using folate receptor-targeted imaging agents," Cancer Metastasis Rev., 2008, 27, 655-664.
Sentman "Challenges of creating effective chimeric antigen receptors for cancer therapy" Immunotherapy. Aug. 2013;5(8) :783-5.
Serghides et al., "Evaluation of OX40 Ligand as a Costimulator of Human Antiviral Memory CDS T Cell Responses: Comparison with B7.1 and 4-1BBL," The Journal of Immunology 175:6368-6377 (2005).
Shields et al., "High Resolution Mapping of the Binding Site on Human IgG1 for FcγRI, FcγRII, FcγRIII, and FcRn and Design of IgG1 Variants with Improved Binding to the FcγR*," The Journal of Bioloaical Chemistry 2001, vol. 276, No. 9, Issue of March 2, pp. 6591-6604.
Shirasu, N. et al., "Construction and Molecular Characterization of Human Chimeric T-Cell Antigen Receptors Specific for Carcinoembryonic Antigen," Anticancer Research (2010); 30:2731-2738.
Sobota et al., "Binding of IgG-Opsonized Particles to FcγR Is an Active Stage of Phagocytosis That Involves Receptor Clustering and Phosphorylation," The Journal of Immunology 2005; 175:4450-4457.
Song et al., "In vivo persistence, tumor localization and anti-tumor activity of CAR engineered T cells is enhanced by costimulatory signaling through CD137 (4-IBB)," Cancer Research (2011); 71:4617-27.
Song, DG, et al., "CD27 costimulation augments the survival and antitumor activity of redirected human T cells in vivo," Blood (Jan. 19, 2012); 119(3):696-706 (Epub Nov. 23, 2011).
Song, DG, et al., "A fully human chimeric antigen receptor with potent activity against cancer cells but reduced risk for off-tumor toxicity," Oncotarget (Aug. 28, 2015) ;6(25):21533-46.
Stancovski et al., "Targeting of T Lymphocytes to Neu/HERZ-Expressing Cells Using Chimeric Single Chain Fv Receptors," J. Immunol. (1993); 151( 11):6577-6582.
Stein et al.,"The Cytoplasmic Domain of CD28 Is both Necessary and Sufficient for Costimulation of Interleukin-2 Secretion and Association with Phosphatidylinositol 3'-Kinase," Molecular And Cellular Biology, (May 1994) 14(5): 3392-3402.
Stein, P, et al., The Cytoplasmic Domain of CD28 Is both Necessary and Sufficient for Costimulation of Interleukin-2 Secretion and Association with Phosphatidylinositol 3'-Kinase, American Society for Microbiology (1994); 14: 3392-3402.
Stephan et al., "T cell-encoded CDSO and 4-1BBL induce auto- and transcostimulation, resulting in potent tumor rejection," Nature Medicine (Dec. 2007); 13(12): 1440-1449.
Stevens et al., "Generation of Tumor-Specific CTLs from Melanoma Patients by Using Peripheral Blood Stimulated with Allogeneic Melanoma Tumor Cell Lines," J. Immunol (1995); 154:762-771.
Stone, J.D., et al., "A sensitivity scale for targeting T cells with chimeric antigen receptors (CARs) and bispecific T-cell Engagers (BiTEs)," Oncoimmunology (Sep. 2012); 1(6): 863-873.
Suhoski, M.M., et al., Engineering artificial antigen-presenting cells to express a diverse array of co-stimulatory molecules. Mal Ther, 2007. 15(5): p. 981-8.
Swanson et al., "The coordination of signaling during Fe receptor-mediated phagocytosis," Journal of Leukocyte Biology, vol. 76, Dec. 2004, DD. 1093-1103.
Tam et al., "Functional, Biophysical, and Structural Characterization of Human IgG1 and IgG4 Fe Variants with Ablated Immune Functionality," *Antibodies* 2017, 6, 12.
Tamada et al., "Redirecting gene-modified T cells toward various cancer types using tagged antibodies," Clinical Cancer Research (2012); 18: 6436-6445 (Epub Oct. 2, 2012) AND Correction at Clin Cancer Res. (Feb. 15, 2013); 19(4):951 (Published OnlineFirst Jan. 25, 2013).
Tamada (2013) Correction: Redirecting Gene-Modified T Cells toward Various Cancer Types Using tagged Antibodies—Feb. 14, 2013.
Tamada, K. et al: Redirecting Gene-Modified T Cells toward Various Cancer Types Using Tagged Antibodies, Clinical Cancer Research, vol. 18, No. 23, Oct. 2, 2012 (Oct. 2, 2012), pp. 6436-6445.
Tan, et al. "Influence of the Hinge Region on Complement Activation, Clq Binding, and Segmental Flexibility in Chimeric Human Immunoglobulins," Proceedings of the National Academy of Sciences (Jan. 1990); 87:162-6.
Tanaka, Toshio et al. "Immunotherapeutic implications of IL-6 blockade for cytokine storm." Immunotherapy. Jul. 2016;8(8) :959-70.
Teachey D. T. et al. "Cytokine release syndrome after blinatumomab treatment related to abnormal macrophage activation and ameliorated with cytokine-directed therapy" Blood. Jun. 27, 2013;121(26):5154-7. doi: 10.1182/blood-2013-02-485623. Epub May 15, 2013.
Terakura, S., et al., "Generation of CD19-chimeric antigen receptor modified CDS+ T cells derived from virus-specific central memory T cells" Blood (2012); 119(1): 72-82 (Epub Oct. 26, 2011).
The LTR Retroviral Promoter; Long Terminal Repeats: The Retroviral Promoter. https://web.stanford.edu/group/nolan/_OldWebsite/tutorials/retcl_3_1trs.html retrieved Jul. 26, 2018.
Themeli, M., et al., "Generation of tumor-targeted human T lymphocytes from induced pluripotent stem cells for cancer therapy," Nat Biotechnol (2013); 31(10):928-33 (Eoub Aug. 11, 2013).

(56) References Cited

OTHER PUBLICATIONS

Till, et al., "Adoptive immunotherapy for indolent non-Hodgkin lymphoma and mantle cell lymphoma using genetically modified autologous CD20-specific T cells," Blood (2008); 112:2261-2271.
Traversari, C., et al., "The potential immunogenicity of the TK suicide gene does not prevent full clinical benefit associated with the use of TK-transduced donor lymphocytes in HSCT for hematologic malignancies," Blood (2007); 109(11): 4708-15.
Tsukahara et al. "CD19 target-engineered T-cells accumulate at tumor lesions in humanB-cell lymphoma xenograft mouse models" (2013) Biochem Biophys Res Commun 438(1): 84-9. Epub Jul. 17, 2013.
Turatti, F., et al., "Redirected activity of human antitumor chimeric immune receptors is governed by antigen and receptor expression levels and affinity of interaction," J Immunother (2007); 30(7): 684-93.
Turtle et al., "Engineered T cells for anti-cancer therapy" Curr. Opin. Immunol., Oct. 2012; 24(5): 633-39. Epub Jul. 18, 2012.
Uherek, C, et al., "Chimeric antigen receptors for the retargeting of cytotoxic effector cells," J. Hematother. Stem Cell Res. (2001); 10: 523-534.
UniProtKB—043914, "TYRO protein tyrosine kinase-binding protein", oo.1-15.
UniProtKB—P01732 (CD8A_HUMAN). T-cell surface glycoprotein CD8 alpha chain; 11 pages; retrieved on May 13, 2016 from http://www.uniprot.org/uniprot/POI732.
UniProtKB—P02701, AVidin Precursor—Gallus Chicken.
UniProtKB—P10747 (CD28 Human).
UniProtKB—P10966 (CD88 Human).
UniProtKB—P20963 (CD3Z_HUMAN). T-cell surface glycoprotein CD3 zeta chain; 12 pages; retrieved on May 13, 2016 from http://www.uniprot.org/uniprot/P20963.
UniProtKB—Q07011 (TNR9_HUMAN). Tumor necrosis factor receptor superfamily member 9; 14 pages; retrieved on May 13, 2016 from http://www.uniprot.org/uniprot/Q070I I
Urba. W.J. et al., "Redirecting T cells," New Engl. J. Med., 2011, 365, 754-757.
Urbanska, K. et al., "Development of a novel universal immune receptor for antigen targeting: To Infinity and beyond," Oncoimmunology (Aug. 2012 I); 1(5): p. 777-779.
Urbanska, K. et al., "A universal strategy for adoptive immunotherapy of cancer through use of a novel T-cell antigen receptor," Cancer Res., 2012, 72, 1844-1852.
Urbanska, K., et al., "A Universal Immune Receptor Expressed by T Cells for the Targeting of Diverse and Multiple Tumor Associated Antigens" IN Abstracts for the 26th Annual Scientific Meeting of the Society for Immunotherapy of Cancer (SITC), J Immunother, vol. 34, No. 9, Nov.-Dec. 2011 (62 pages), p. 381.
Uttenthal, B.J., et al., Challenges in T cell receptor gene therapy. J Gene Med (Jun. 2012); 14(6): 386-99.
Van Dam, G. et al., "Intraoperative tumor-specific fluorescence imaging in ovarian cancer by folate receptor-a targeting: first in-human results," Nature Medicine, 2011, 17, 1315-1319.
Vaughan et al., "Human antibodies with sub-nanomolar affinities isolated from a large non-immunized phage display library," Nat Biotechnol. Mar. 1996; 14(3):309-14.
Verdine et al., "The Challenge of Drugging Undruggable Targets in Cancer: Lessons Learned from Targeting BCL-2 Family Members" Clin. Cancer Res. vol. 13, No. 24, Dec. 15, 2007, pp. 7264-7270.
Verhoeven et al. "Lentiviral vector gene transfer into human T cells" (2009) Methods Mal Biol. 506: 97-114.
Wang et al. "Phenotypic and functional attributes of lentivirus-modified CD19-specific human CDS+ central memory T cells manufactured at clinical scale" (2012) J Immunother. 35(9) :689-701.
Wayua, C. et al., "Evaluation of a Cholecystokinin 2 Receptor-Targeted Near-Infrared Dye for Fluorescence-Guided Surgery of Cancer," Molecular Pharmaceutics, 2014, 11, 468-476.

Weijtens, M. E. et al., "Single chain Ig/gamma gene-redirected human T lymphocytes produce cytokines, specifically lyse tumor cells, and recycle lytic capacity.," J. Immunol. (Jul. 15, 1996); 157(2):836-43.
Weissman et al., "Molecular cloning and chromosomal localization of the human T-cell receptor zeta chain: Distinction from the molecular CD3 complex" Proc. Natl. Acad. Sci. vol. 85, Dec. 1988, pp. 9709-9713.
Weissman et al., "Role of the zeta chain in the expression of the T cell antigen receptor: genetic reconstitution studies" The EMBO Journal, vol. 8, No. 12, 1989, pp. 3651-3656.
Wen, T, et al., "4-188 Ligand-Mediated Costimulation of Human T Cells Induces CD4 and CDS T Cell Expansion, Cytokine Production, and the Development of Cytolytic Effector Function1," 4897-4906.
Wesolowski, J, et al., "Single domain antibodies: promising experimental and therapeutic tools in infection and immunity", Med Microbiol Immunol (2009) 198:157-174.
Wikicedia, Amino acid, https://en.wikicedia.on::i/wiki/Amino acid, downloaded Jul. 30, 2018.
Wikipedia, Antibody, https://en.wikipedia .org/w/index.php?title=Antibody&oldid=851456273, downloaded Jul. 22, 2018.
Wikipedia, Fe receptor, https:l/en.wikipedia.org/w/index.php?title=Fc_receptor&oldid=845940301, downloaded Jun. 15, 2018.
Wikipedia, CD28, https://en.wikipedia.org/w/index.php?title=CD28&oldid=831459950, downloaded Mar. 20, 2018.
Wikipedia, IL-2 receptor, https://en.wikipedia.org/w/index.php?title=IL-2_receptor&oldid=847173411, downloaded Jun. 23, 2018.
Wikipedia, Killer-cell immunoglobulin-like receptor, https://en.wikipedia.org/wiki/Killer-cell immunoglobulin-like_receptor, downloaded Jul. 25, 2018.
Wikipedia, CD137, https://en.wikipedia.org/w/index.php?title=CD137&oldid=788581779, downloaded Jul. 2, 2017.
Wikipedia, Folate, https://en.wikipedia.org/w/index.php?title=Folate&oldid=851466622, downloaded Jun. 22, 2018.
Wikipedia, Single-domain antibody, https://en.wikipedia.org/wiki/Single-domain_antibody, downloaded Jul. 27, 2018.
Wikipedia, FOLR2, https://en.wikipedia.org/w/index.php?title=FOLR2&oldid=798129670, downloaded Aug. 31, 2017.
Wikipedia, CD3 (immunology), https://en.wikipedia.org/wiki/CD3_(immunology), downloaded Jul. 24, 2018.
Wikipedia, Folate receptor, https://en.wikipedia.org/w/index.php?title=Folate_receptor&oldid=834246297, downloaded Apr. 4, 2018.
Wikipedia, Cytokine I https://en.wikipedia.org/w/index.php?title=Cytokine&oldid=847147607, downloaded Jun. 23, 2018.
Wikipedia, Interferon, https:l/en.wikipedia.org/w/index.php?title=Interferon&oldid=848844304, downloaded Jul. 4, 2018.
Wikipedia, Interleukin-1 family, https://en.wikipedia.org/w/index.php?title=Interleukin-1 family&oldid=847253010, downloaded Jun. 24, 2018.
Wikipedia, CDS, https://en.wikipedia.org/w/index.php?title=CDB&oldid=840166968, downloaded May 8, 2018.
Wikipedia, Cholecystokinin B receptor, https://en.wikipedia.org/w/index.php?title=Cholecystokinin_B_receptor&oldid=837355377, downloaded Apr. 20, 2018.
Wikipedia, Folate receptor 1, https:1/en.wikipedia.org/w/index.php?title=Folate_receptor_1&oldid=845790606, downloaded Jun. 14, 2018.
Wikipedia, Folate receptor gamma, https:llen.wikipedia.org/w/index.php?title=Folate_receptor_gamma&oldid=621589158, downloaded Aug. 17, 2014.
Wikipedia, Interleukin 2, https:1/en.wikipedia.org/w/index.php?title=Interleukin_2&oldid=838351127, downloaded Apr. 26, 2018.
Wikipedia, Single-chain variable fragment, https:1/en.wikipedia.org/w/index.php?title=Single- chain_variable_fragment&oldid=841449115, downloaded May 15, 2018.
Wikipedia, TNF receptor superfamily, https:1/en.wikipedia.org/w/index.php?title=TNF_receptor_superfamily&oldid=850804991, downloaded Jul. 18, 2018.
Wikipedia, Avidin, (2018) retrieved from https://en.wikipedia.org/w/index.php?title=Avidin&oldid=849308130.
Wikipedia, Avidin, https://en.wikipedia.org/wiki/Avidin, downloaded Aug. 24, 2018.

(56) References Cited

OTHER PUBLICATIONS

Wikipedia, C-type lectin, https://en.wikipedia.org/wiki/C-type lectin, downloaded Jul. 25, 2018.
Wikipedia, Glutamate carboxypeptidase II, https://en.wikipedia.org/w/index.php?title=Glutamate_carboxypeptidase_II&oldid=845231234, downloaded Jun. 10, 2018.
Wikipedia, Glvcosvlation, https://en.wikipedia.org/wiki/Glycosylation, downloaded Jul. 31, 2018.
Wikipedia, Interleukin 10, https:llen.wikipedia.org/w/index.php?title=Interleukin_10&oldid=835415026, downloaded Apr. 8, 2018.
Wikipedia, KLRA1, https://en.wikipedia.orQ/wiki/KLRA1, downloaded Jul. 25, 2018.
Wikipedia, NKG2D, https://en.wikipedia.org/wiki/NKG2D, downloaded Jul. 25, 2018.
Wikipedia, Paratope, https://en.wikipedia.org/wiki/Paratope, downloaded Jul. 25, 2018.
Wikipedia, Protein, https://en.wikipedia.org/w/index.php?title=Protein&oldid=861574349, downloaded Oct. 15, 2018.
Wikipedia, Small molecule, https://en.wikipedia.org/wiki/Small molecule, downloaded Jul. 27, 2018.
Wikipedia, Transforming growth factor beta superfamily, https://en.wikipedia.org/w/index.php?title=Transforming_growth factor beta superfamily&oldid=850390369, downloaded Jul. 15, 2018.
Wikipedia. "Chimeric antigen receptor"; 9 pages; retrieved on Nov. 13, 2014 from http://en.wikipedia.org/wiki/Chimeric_antigen_receptor.
Wilkie et al., "Retargeting of Human T Cells to Tumor-Associated MUC1: The Evolution of a Chimeric Antigen Receptor," The Journal of Immunology Apr. 2008, pp. 4901-4909.
Wilson, et al. "DAPI2 and KAP IO (DAPIO)-novel transmembrane adapter proteins of the CD3zeta family," Immunol Res. (2000); 22(1):21-42.
WO2010/025177—Sequence Listing (Mar. 4, 2010).
Wu et al., "Adoptive T-cell therapy using autologous tumor-infiltrating lymphocytes for metastatic melanoma: current status and future outlook" Cancer, Mar. 18, 2012(2): 160-75.
Wu et al., "An Activating Immunoreceptor Complex Formed by NKG2D and DAP1O," Science, New Series, 285(5428): 730-732 (Jul. 30, 1999).
Wu, et al., "Remote control of therapeutic T cells through a small molecule-gated chimeric receptor," Science (Oct. 16, 2015); 350(6258): 293 and aab4077-I through aab4077-I0 (epub Sep. 24, 2015) (12 pages).
Xu et al., "Cytokine release syndrome in cancer immunotherapy with chimeric antigen receptor engineered T cells" Cancer Lett. Feb. 28, 2014;343(2):172-8. Epub Oct. 16, 2013.
Xu, X.J., et al., "Efficacy and safety of adoptive immunotherapy using anti-CD 19 chimeric antigen receptor transduced T-cells: a systematic review of phase I clinical trials," Leuk Lymphoma (2013); 54(2): 255-60 (Published online: Sep. 8, 2012).
Ye, H, et al., "The Structural Basis for the Recognition of Diverse Receptor Sequences by TRAF2," The Weill Medical College and Graduate School of Medical Sciences of Cornell University; v: 321-330.
Yee, C., et al., "Prospects for Adoptive T Cell Therapy," Current Opinion in Immunology (1997); 9(5):702-708.
Zacchetti, A, "Antitumor effects of a human dimeric antibody fragment 131I-AFRA-DFM5.3 in a mouse model for ovarian cancer," J Nucl Med (Dec. 2011); 52(12): 1938-46 (Epub Nov. 8, 2011).
Zhang et al., "Phase I Escalating-Dose Trial of CAR-T Therapy Targeting CEA+ Metastatic Colorectal Cancers," Molecular Therapy (2017), 25(5): 1248-1258.
Zhang, et al., "Chimeric NKG2D modified T cells inhibit systemic T-cell lymphoma growth in a manner involving multiple cytokines and cytotoxic pathways," Cancer Res. (2007); 67(22): 11029-36.
Zhang, et al., "Generation of antitumor responses by genetic modification of primary human T cells with a chimeric NKG2D receptor," Cancer Res. (2006); 66(11):5927-33.
Zhang, et al., "Chimeric NK-receptor-bearing T cells mediate antitumor immunotherapy," Blood (2005); 106(5):1544-1551.
Zhang, H., et al., 4-1BB is superior to CD28 costimulation for generating CDS+ cytotoxic lymphocytes for adoptive immunotherapy. J Immunol, 2007. 179(7): p. 4910-8.
Zhao, Y. et al., "A herceptin-based chimeric antigen receptor with modified signaling domains leads to enhanced survival of transduced T lymphocytes and antitumor activity," J. Immunol, 2009, 183, 5563-5574.
Zheng et al., "Arming Tumor-Reactive T Cells with Costimulator B7-1 Enhances Therapeutic Efficacy of the T Cells," Cancer Research, 2006, vol. 66, No. 13, pp. 6793-6799.
Zhong, et al., "Chimeric Antigen Receptors Combining 4-IBB and CD28 Signaling Domains Augment PI3kinase/AKT/Bcl-XL Activation and Cds+ T Cell-mediated Tumor Eradication," Molecular Therapy (Feb. 2010); 18(2): 413-420.
Zhong, et al., "Integrated CD28 and 4-1B8 Signals Strongly Potentiate CDS+ T Cell Mediated Eradication of Metastatic Prostate Cancer," Molecular Therapy (Jan. 1, 2006); 13: p. S103, Abstract.
Extended European Search Report issued by the European Patent Office for Application No. 19204092.1, dated Mar. 16, 2020, 8 pages.
Farkas A, et al., "Proarrhythmic effects of intravenous quinidine, amiodarone, D-sotalol, and almokalant in the anesthetized rabbit model of torsade de pointes", Journal of Cardiovascular Pharmacology, Feb. 2002, vol. 39(2), pp. 287-297.
GenBank: AMZ04818.1, Zah, E. et al., dated Apr. 24, 2016, 6 pages.
Ren B Y, et al., "Safety Strategies of Genetically Engineered T Cells in Cancer Immunotherapy", Current Pharmaceutical Design, 2018, vol. 24(1), pp. 78-83.
Zah, E., et al., "T Cells Expressing CD19/CD20 Bispecific Chimeric Antigen Receptors Prevent Antigen Escape by Malignant B Cells," Cancer Immunology Research, Jun. 2016, vol. 4 (6), pp. 498-508.
"International Application Serial No. PCT US2013 076986, Written Opinion mailed Apr. 28, 2014", 9 pgs.
"European Application Serial No. 19204092.1, Response filed Feb. 18, 21 to Extended European Search Report mailed Mar. 20, 2020", 54 pgs.
"European Application Serial No. 19204092.1, Noting of loss of rights pursuant to Rule 112(1) EPC mailed Dec. 11, 2020", 1 pg.
"European Application Serial No. 19204092.1, Intention to Grant mailed Nov. 21, 2022", 100 pgs.
"European Application Serial No. 19204092.1, Communication Pursuant to Article 94(3) EPC mailed Jun. 23, 2022", 1 pgs.
"European Application Serial No. 19204092.1, Response filed Jul. 19, 2022 to Communication Pursuant to Article 94(3) EPC mailed Jun. 23, 2022", 3 pgs.
"European Application Serial No. 23169858.0, Response filed Aug. 20, 2024 to Noting a Loss of Rights pursuant to Rule 112(1) EPC", 14 pgs.

SCHEME 1. Synthesis of the Folate-(PEG)$_{12}$-FITC Spacer Unit:
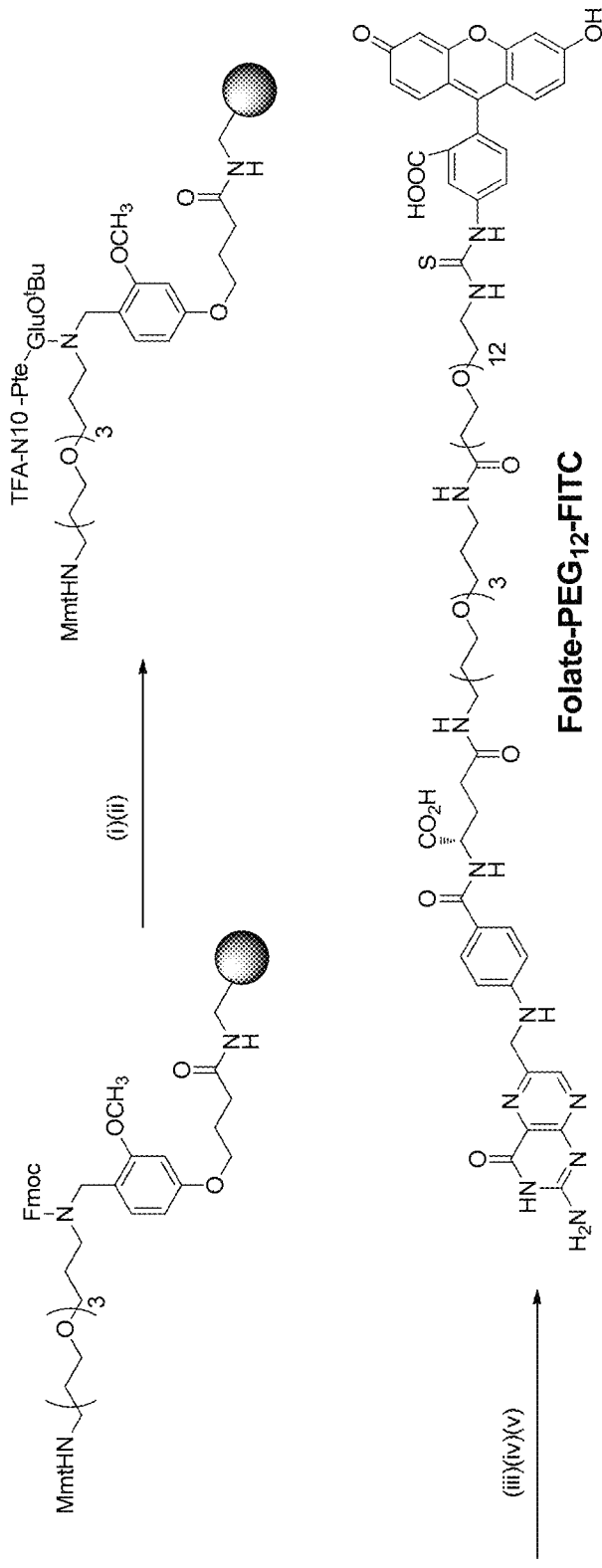
Reagents and conditions: (i) a) 20%piperidine, DMF; b) Fmoc-NH-Glu(O$^t$Bu)-COOH, PyBOP,DIPEA, DMF; (ii) a) 20%piperidine, DMF; b) N$^{10}$-(Trifluoroacetyl)pteroic acid,PyBOP,DIPEA,DMF; (iii) a) 1M HOBT in DCM:TFE (1:1); b) Fmoc-NH-PEG$_{12}$CH$_2$CH$_2$COOH, PyBOP, DIPEA, DMF;(iv) a) 20%piperidine, DMF; b) FITC, DIPEA, DMF; (v) a) 2% NH$_2$NH$_2$ ,DMF; b) TFA, water, i-Pr$_3$SiH.

SCHEME 1. Synthesis of the DUPA-(PEG)₁₂-EDA Spacer Unit[a]

[a]Reagents and conditions: (i) Fmoc-NH(PEG)₁₂-COOH, PyBop, DIPEA, DMF; (ii) 20%piperidine, DMF; (iii) Fmoc-Phe-OH, PyBop, DIPEA, DMF; (iv) Fmoc-8-amino octanoic acid, PyBop, DIPEA, DMF; (v) DUPA, PyBop, DIPEA, DMF; (vi) TFA, water, i-Pr₃SiH.

SCHEME 2. Synthesis of the DUPA-(PEG)12-EDA-FITC

SCHEME 3. Synthesis of the Z360-(PEG)₁₂-EDA Spacer Unit[a]

[a]Reagents and conditions: (i) Fmoc-NH(PEG)₁₂-COOH, PyBop, DIPEA, DMF; (ii) 20%piperidine, DMF; (iii) Z360, PyBop, DIPEA, DMF; (iv) TFA, water, i-Pr₃SiH.

SCHEME 4. Synthesis of the Z360-(PEG)₁₂-EDA-FITC

SEQUENCE LISTING

<160> NUMBER OF SEQ ID NOS: 2

<210> SEQ ID NO 1
<211> LENGTH: 8561
<212> TYPE: DNA
<213> ORGANISM: Artificial Sequence
<220> FEATURE:
<223> OTHER INFORMATION: lentivirus expression construct encoding a
      chimeric antigen receptor

<400> SEQUENCE: 1

| | | | | | | |
|---|---|---|---|---|---|---|
| acgcgtgtag | tcttatgcaa | tactcttgta | gtcttgcaac | atggtaacga | tgagttagca | 60 |
| acatgcctta | caaggagaga | aaaagcaccg | tgcatgccga | ttggtggaag | taaggtggta | 120 |
| cgatcgtgcc | ttattaggaa | ggcaacagac | gggtctgaca | tggattggac | gaaccactga | 180 |
| attgccgcat | tgcagagata | ttgtatttaa | gtgcctagct | cgatacataa | acgggtctct | 240 |
| ctggttagac | cagatctgag | cctgggagct | ctctggctaa | ctagggaacc | cactgcttaa | 300 |
| gcctcaataa | agcttgcctt | gagtgcttca | agtagtgtgt | gcccgtctgt | tgtgtgactc | 360 |
| tggtaactag | agatccctca | gacccttttta | gtcagtgtgg | aaaatctcta | gcagtggcgc | 420 |
| ccgaacaggg | acttgaaagc | gaaagggaaa | ccagaggagc | tctctcgacg | caggactcgg | 480 |
| cttgctgaag | cgcgcacggc | aagaggcgag | gggcggcgac | tggtgagtac | gccaaaaatt | 540 |
| ttgactagcg | gaggctagaa | ggagagagat | gggtgcgaga | gcgtcagtat | taagcggggg | 600 |
| agaattagat | cgcgatggga | aaaaattcgg | ttaaggccag | ggggaaagaa | aaaatataaa | 660 |
| ttaaaacata | tagtatgggc | aagcagggag | ctagaacgat | tcgcagttaa | tcctggcctg | 720 |
| ttagaaacat | cagaaggctg | tagacaaata | ctgggacagc | tacaaccatc | ccttcagaca | 780 |
| ggatcagaag | aacttagatc | attatataat | acagtagcaa | ccctctattg | tgtgcatcaa | 840 |
| aggatagaga | taaagacac | caaggaagct | ttagacaaga | tagaggaaga | gcaaaacaaa | 900 |
| agtaagacca | ccgcacagca | agcggccact | gatcttcaga | cctggaggag | gagatatgag | 960 |
| ggacaattgg | agaagtgaat | tatataaata | taaagtagta | aaaattgaac | cattaggagt | 1020 |
| agcacccacc | aaggcaaaga | gaagagtggt | gcagagagaa | aaaagagcag | tgggaatagg | 1080 |
| agctttgttc | cttgggttct | tgggagcagc | aggaagcact | atgggcgcag | cgtcaatgac | 1140 |
| gctgacggta | caggccagac | aattattgtc | tggtatagtg | cagcagcaga | acaatttgct | 1200 |
| gagggctatt | gaggcgcaac | agcatctgtt | gcaactcaca | gtctggggca | tcaagcagct | 1260 |
| ccaggcaaga | atcctggctg | tggaaagata | cctaaaggat | caacagctcc | tgggatttg | 1320 |
| gggttgctct | ggaaaactca | tttgcaccac | tgctgtgcct | tggaatgcta | gttggagtaa | 1380 |
| taaatctctg | gaacagattt | ggaatcacac | gacctggatg | gagtgggaca | gagaaattaa | 1440 |
| caattacaca | agcttaatac | actccttaat | tgaagaatcg | caaaaccagc | aagaaaagaa | 1500 |
| tgaacaagaa | ttattggaat | tagataaatg | ggcaagtttg | tggaattggt | ttaacataac | 1560 |
| aaattggctg | tggtatataa | aattattcat | aatgatagta | ggaggcttgg | taggtttaag | 1620 |
| aatagttttt | gctgtacttt | ctatagtgaa | tagagttagg | cagggatatt | caccattatc | 1680 |
| gtttcagacc | cacctcccaa | ccccgagggg | acccgacagg | cccgaaggaa | tagaagaaga | 1740 |
| aggtggagag | agagacagag | acagatccat | tcgattagtg | aacggatctc | gacggtatcg | 1800 |
| gttaactttt | aaaagaaaag | gggggattgg | ggggtacagt | gcagggaaa | gaatagtaga | 1860 |
| cataatagca | acagacatac | aaactaaaga | attacaaaaa | caaattacaa | aattcaaaat | 1920 |
| tttatcgata | ctagtaagga | tctgcgatcg | ctccggtgcc | cgtcagtggg | cagagcgcac | 1980 |

```
atcgcccaca gtccccgaga agttgggggg aggggtcggc aattgaacgg gtgcctagag    2040
aaggtggcgc ggggtaaact gggaaagtga tgtcgtgtac tggctccgcc ttttcccga     2100 gggtggggga gaaccgtata taagtgcagt agtcgccgtg aacgttcttt ttcgcaacgg    2160
gtttgccgcc agaacacagc tgaagcttcg aggggctcgc atctctcctt cacgcgcccg    2220
ccgccctacc tgaggccgcc atccacgccg gttgagtcgc gttctgccgc ctcccgcctg    2280
tggtgcctcc tgaactgcgt ccgccgtcta ggtaagttta aagctcaggt cgagaccggg    2340
cctttgtccg gcgctccctt ggagcctacc tagactcagc cggctctcca cgctttgcct    2400
gaccctgctt gctcaactct acgtctttgt ttcgtttttct gttctgcgcc gttacagatc   2460
caagctgtga ccggcgccta ctctagagct agcgaattcg aatttaaatc ggatccgcgg    2520
ccgccgactg tgccttctag ttgccagcca tctgttgttt gcccctcccc cgtgccttcc    2580
ttgaccctgg aaggtgccac tcccactgtc ctttcctaat aaaatgagga aattgcatcg    2640
cattgtctga gtaggtgtca ttctattctg ggggtgggg tggggcagga cagcaagggg    2700
gaggattggg aagacaatag caggcatgct ggggatgcgg tgggctctat ggcctctggc    2760
ctcgcacaca ttccacatcc accggtaggc gccaaccggc tccgttcttt ggtggcccct    2820
tcgcgccacc ttctactcct cccctagtca ggaagttccc ccccgcccg cagctcgcgt     2880 cgtgcaggac gtgacaaatg gaagtagcac gtctcactag tctcgtgcag atggacagca    2940
ccgctgagca atgaagcggg gtaggccttt ggggcagcgg ccaatagcag ctttgctcct    3000
tcgctttctg ggctcagagg ctgggaaggg gtgggtccgg gggcgggctc aggggcgggc    3060
tcaggggcgg ggcgggcgcc cgaaggtcct ccggaggccc ggcattctgc acgcttcaaa    3120
agcgcacgtc tgccgcgctg ttctcctctt cctcatctcc gggcctttcg acctgcatct    3180
agagccgcca tggcttaccc atacgatgtt ccagattacg ctagttttggt gaggcagcag   3240 agaccgatgg agagcgacga gagcggcctg cccgccatgg agatcgagtg ccgcatcacc    3300
ggcaccctga acggcgtgga gttcgagctg gtgggcggcg agagggcac ccccaagcag     3360 ggccgcatga ccaacaagat gaagagcacc aaaggcgccc tgaccttcag cccctacctg    3420
ctgagccacg tgatgggcta cggcttctac cacttcggca cctaccccag cggctacgag    3480
aaccccttcc tgcacgccat caacaacggc ggctacacca cacccgcat cgagaagtac     3540 gaggacggcg cgtgctgca cgtgagcttc agctaccgct acgaggccgg ccgcgtgatc    3600
ggcgacttca aggtggtggg caccggcttc cccgaggaca gcgtgatctt caccgacaag    3660
atcatccgca gcaacgccac cgtggagcac ctgcacccca tgggcgataa cgtgctggtg    3720
ggcagcttcg cccgcaccttt cagcctgcgc gacggcggct actacagctt cgtggtggac    3780
agccacatgc acttcaagag cgccatccac cccagcatcc tgcagaacgg ggcccccatg    3840
ttcgccttcc gccgcgtgga ggagctgcac agcaacaccg agctgggcat cgtggagtac    3900
cagcacgcct tcaagacccc catcgccttc gccagatccc gcgctcagtc gtccaattct    3960
gccgtggacg gcaccgccgg acccggctcc accggatctc gcgagggcag aggaagtctt    4020
ctaacatgcg gtgacgtgga ggagaatccc ggccctatga ccgagtacaa gcccacggtg    4080
cgcctcgcca cccgcgacga cgtccccagg gccgtacgca ccctcgccgc gcgttcgcc     4140 gactaccccg ccacgcgcca caccgtcgat ccggaccgcc acatcgagcg ggtcaccgag    4200
ctgcaagaac tcttcctcac gcgcgtcggg ctcgacatcg gcaaggtgtg ggtcgcggac    4260 gacgcgccc cggtggcggt ctggaccacg ccggagagcc tcgaagcggg gcggtgttc      4320 gccgagatcg gcccgcgcat ggccgagttg agcggttccc ggctggccgc gcagcaacag    4380
```

```
atggaaggcc tcctggcgcc gcaccggccc aaggagcccg cgtggttcct ggccaccgtc    4440
ggcgtctcgc ccgaccacca gggcaagggt ctgggcagcg ccgtcgtgct ccccggagtg    4500
gaggcggccg agcgcgccgg ggtgcccgcc ttcctggaga cctccgcgcc ccgcaacctc    4560
cccttctacg agcggctcgg cttcaccgtc accgccgacg tcgaggtgcc cgaaggaccg    4620
cgcacctggt gcatgacccg caagcccggt gcctgaaatc aacctctgga ttacaaaatt    4680
tgtgaaagat tgactggtat tcttaactat gttgctcctt ttacgctatg tggatacgct    4740
gctttaatgc ctttgtatca tgctattgct cccgtatgg ctttcatttt ctcctccttg     4800
tataaatcct ggttgctgtc tctttatgag gagttgtggc ccgttgtcag caacgtggc     4860 gtggtgtgca ctgtgtttgc tgacgcaacc cccactggtt ggggcattgc caccacctgt    4920
cagctccttt ccgggacttt cgcttttccc ctccctattg ccacggcgga actcatcgcc    4980
gcctgccttg cccgctgctg gacaggggct cggctgttgg gcactgacaa ttccgtggtg    5040
ttgtcgggga atcatcgtc ctttccttgg ctgctcgcct gtgttgccac ctggattctg     5100
cgcgggacgt ccttctgcta cgtcccttcg gccctcaatc agcggacct tccttcccgc     5160 ggcctgctgc cggctctgcg gcctcttccg cgtctccgcc ttcgccctca gacgagtcgg    5220
atctcccttt ggccgcctcc ccgcctggta cctttaagac caatgactta caaggcagct    5280
gtagatctta gccactttt aaaagaaaag gggggactgg aagggctaat tcactcccaa     5340
cgaagataag atctgctttt tgcttgtact gggtctctct ggttagacca gatctgagcc    5400
tgggagctct ctggctaact agggaaccca ctgcttaagc ctcaataaag cttgccttga    5460
gtgcttcaag tagtgtgtgc ccgtctgttg tgtgactctg gtaactagag atccctcaga    5520
cccttttagt cagtgtggaa aatctctagc agtagtagtt catgtcatct tattattcag    5580
tatttataac ttgcaaagaa atgaatatca gagagtgaga ggaacttgtt tattgcagct    5640
tataatggtt acaaataaag caatagcatc acaaatttca caaataaagc attttttca     5700 ctgcattcta gttgtggttt gtccaaactc atcaatgtat cttatcatgt ctggctctag    5760
ctatcccgcc cctaactccg cccagttccg cccattctcc gccccatggc tgactaattt    5820
tttttattta tgcagaggcc gaggccgcct cggcctctga ctattccag aagtagtgag     5880 gaggcttttt tggaggccta acttttgca gagacggccc aaattcgtaa tcatggtcat     5940
agctgtttcc tgtgtgaaat tgttatccgc tcacaattcc acacaacata cgagccggaa    6000
gcataaagtg taaagcctgg ggtgcctaat gagtgagcta actcacatta attgcgttgc    6060
gctcactgcc cgctttccag tcgggaaacc tgtcgtgcca gctgcattaa tgaatcggcc    6120
aacgcgcggg gagaggcggt ttgcgtattg ggcgctcttc cgcttcctcg ctcactgact    6180
cgctgcgctc ggtcgttcgg ctgcggcgag cggtatcagc tcactcaaag gcggtaatac    6240
ggttatccac agaatcaggg gataacgcag gaaagaacat gtgagcaaaa ggccagcaaa    6300
aggccaggaa ccgtaaaaag gccgcgttgc tggcgttttt ccataggctc cgcccccctg    6360
acgagcatca caaaaatcga cgctcaagtc agaggtggcg aaacccgaca ggactataaa    6420
gataccaggc gtttccccct ggaagctccc tcgtgcgctc tcctgttccg accctgccgc    6480
ttaccggata cctgtccgcc tttctccctt cgggaagcgt ggcgctttct catagctcac    6540
gctgtaggta tctcagttcg gtgtaggtcg ttcgctccaa gctgggctgt gtgcacgaac    6600 ccccgttca gcccgaccgc tgcgccttat ccggtaacta tcgtcttgag tccaacccgg     6660
taagacacga cttatcgcca ctggcagcag ccactggtaa caggattagc agagcgaggt    6720
```

| | |
|---|---|
| atgtaggcgg tgctacagag ttcttgaagt ggtggcctaa ctacggctac actagaagga | 6780 |
| cagtatttgg tatctgcgct ctgctgaagc cagttacctt cggaaaaaga gttggtagct | 6840 |
| cttgatccgg caaacaaacc accgctggta gcggtggttt ttttgtttgc aagcagcaga | 6900 |
| ttacgcgcag aaaaaaagga tctcaagaag atcctttgat cttttctacg gggtctgacg | 6960 |
| ctcagtggaa cgaaaactca cgttaaggga ttttggtcat gagattatca aaaaggatct | 7020 |
| tcacctagat ccttttaaat taaaaatgaa gttttaaatc aatctaaagt atatatgagt | 7080 |
| aaacttggtc tgacagttac caatgcttaa tcagtgaggc acctatctca gcgatctgtc | 7140 |
| tatttcgttc atccatagtt gcctgactcc ccgtcgtgta gataactacg atacgggagg | 7200 |
| gcttaccatc tggccccagt gctgcaatga taccgcgaga cccacgctca ccggctccag | 7260 |
| atttatcagc aataaaccag ccagccggaa gggccgagcg cagaagtggt cctgcaactt | 7320 |
| tatccgcctc catccagtct attaattgtt gccgggaagc tagagtaagt agttcgccag | 7380 |
| ttaatagttt gcgcaacgtt gttgccattg ctacaggcat cgtggtgtca cgctcgtcgt | 7440 |
| ttggtatggc ttcattcagc tccggttccc aacgatcaag gcgagttaca tgatccccca | 7500 |
| tgttgtgcaa aaaagcggtt agctccttcg gtcctccgat cgttgtcaga agtaagttgg | 7560 |
| ccgcagtgtt atcactcatg gttatggcag cactgcataa ttctcttact gtcatgccat | 7620 |
| ccgtaagatg cttttctgtg actggtgagt actcaaccaa gtcattctga atagtgta | 7680 |
| tgcggcgacc gagttgctct tgcccggcgt caatacggga taataccgcg ccacatagca | 7740 |
| gaactttaaa agtgctcatc attggaaaac gttcttcggg gcgaaaactc tcaaggatct | 7800 |
| taccgctgtt gagatccagt tcgatgtaac ccactcgtgc acccaactga tcttcagcat | 7860 |
| cttttacttt caccagcgtt tctgggtgag caaaaacagg aaggcaaaat gccgcaaaaa | 7920 |
| agggaataag ggcgacacgg aaatgttgaa tactcatact cttccttttt caatattatt | 7980 |
| gaagcattta tcagggttat tgtctcatga gcggatacat atttgaatgt atttagaaaa | 8040 |
| ataaacaaat aggggttccg cgcacatttc cccgaaaagt gccacctgac gtctaagaaa | 8100 |
| ccattattat catgacatta acctataaaa ataggcgtat cacgaggccc tttcgtctcg | 8160 |
| cgcgtttcgg tgatgacggt gaaaacctct gacacatgca gctcccggag acggtcacag | 8220 |
| cttgtctgta agcggatgcc gggagcagac aagcccgtca gggcgcgtca gcgggtgttg | 8280 |
| gcgggtgtcg ggctggctt aactatgcgg catcagagca gattgtactg agagtgcacc | 8340 |
| atatgcggtg tgaaataccg cacagatgcg taaggagaaa ataccgcatc aggcgccatt | 8400 |
| cgccattcag gctgcgcaac tgttgggaag ggcgatcggt gcgggcctct tcgctattac | 8460 |
| gccagctggc gaaagggggga tgtgctgcaa ggcgattaag ttgggtaacg ccagggtttt | 8520 |
| cccagtcacg acgttgtaaa acgacggcca gtgccaagct g | 8561 |

<210> SEQ ID NO 2
<211> LENGTH: 1533
<212> TYPE: DNA
<213> ORGANISM: Artificial Sequence
<220> FEATURE:
<223> OTHER INFORMATION: polynucleotide sequence encoding chimeric antigen receptor CAR4-1BBZ

<400> SEQUENCE: 2

| | |
|---|---|
| atggcctcac cgttgacccg ctttctgtcg ctgaacctgc tgctgctggg tgagtcgatt | 60 |
| atcctgggga gtggagaagc tgatgtcgtg atgacccaga ccccctcag cctcccagtg | 120 |
| tccctcggtg accaggcttc tattagttgc agatccagcc agtccctcgt gcactctaac | 180 |

-continued

```
ggtaatacct acctgagatg gtatctccag aagcccggac agagccctaa ggtgctgatc      240
tacaaagtct ccaaccgggt gtctggagtc cctgaccgct tctcagggag cggttccggc      300
accgacttca ccctgaagat caaccgggtg gaggccgaag acctcggcgt ctatttctgc      360
tctcagagta cacatgtgcc ctggaccttc ggcggaggga ccaagctgga gatcaaaagc      420
tccgcagacg atgccaagaa agatgccgct aagaaagacg atgctaagaa agacgatgca      480
aagaaagacg gtggcgtgaa gctggatgaa accggaggag gtctcgtcca gccaggagga      540
gccatgaagc tgagttgcgt gaccagcgga ttcacctttg ggcactactg gatgaactgg      600
gtgcgacagt ccccagagaa ggggctcgaa tgggtcgctc agttcaggaa caaaccctac      660
aattatgaga catactattc agacagcgtg aagggcaggt ttactatcag tagagacgat      720
tccaaatcta gcgtgtacct gcagatgaac aatctcaggg tcgaagatac aggcatctac      780
tattgcacag gggcatccta tggtatggag tatctcggtc aggggacaag cgtcacagtc      840
agtgtgaact ctactactac caagccagtg ctgcgaactc cctcacctgt gcaccctacc      900
gggacatctc agccccagag accagaagat tgtcggcccc gtggctcagt gaaggggacc      960
ggattggact tcgcctgtga tatttacatc tgggcaccct tggccggaat ctgcgtggcc     1020
cttctgctgt ccttgatcat cactctcatc tctgtgctca aatggatcag gaaaaaattc     1080
ccccacatat tcaagcaacc atttaagaag accactggag cagctcaaga ggaagatgct     1140
tgtagctgcc gatgtccaca ggaagaagaa ggaggaggag gaggctatga gctgagagca     1200
aaattcagca ggagtgcaga gactgctgcc aacctgcagg accccaacca gctctacaat     1260
gagctcaatc tagggcgaag agaggaatat gacgtcttgg agaagaagcg ggctcgggat     1320
ccagagatgg gaggcaaaca gcagaggagg aggaaccccc aggaaggcgt atacaatgca     1380
ctgcagaaag acaagatggc agaagcctac agtgagatcg gcacaaaagg cgagaggcgg     1440
agaggcaagg ggcacgatgg cctttaccag ggtctcagca ctgccaccaa ggacacctat     1500
gatgccctgc atatgcagac cctggcccct cgc                                  1533
```

CHIMERIC ANTIGEN RECEPTOR-EXPRESSING T CELLS AS ANTI-CANCER THERAPEUTICS

CROSS-REFERENCE TO RELATED APPLICATIONS

This application is a continuation of U.S. patent application Ser. No. 15/296,666, filed on Oct. 18, 2016, which is a continuation of U.S. patent application Ser. No. 14/654,227, filed on Jun. 19, 2015, which is the national stage entry of International Patent Application No. PCT/US2013/076986, filed on Dec. 20, 2013, which claims benefit of priority to U.S. Provisional Application No. 61/740,384, filed on Dec. 20, 2012, each of which is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is UMOJ_026_04US_ST25. The text file is 14 KB, created on Sep. 23, 2021, and is being submitted electronically via EFS-Web.

BACKGROUND

Immunotherapy based on adoptive transfer of lymphocytes (e.g., T cells) into a patient can play an important role in eliminating cancer. Among many different types of immunotherapeutic agents, one of the most promising therapeutic methods being developed is T cells expressing Chimeric Antigen Receptors (CAR). CARs are genetically engineered receptors that are designed to target a specific antigen of a selected tumor [1]. For example, T cells that have cytotoxic activity are transfected with and grown to express CARs such that T cells expressing CARs can target and kill tumors via tumor-associated antigens.

First generation CARs are composed of two main regions. First, a recognition region, e.g., a single chain fragment variable (scFv) region derived from a tumor-targeted antibody, is used to recognize and bind tumor-associated antigens. Second, an activation signaling domain, e.g., the CD3ζ chain of T cells, serves as a T cell activation signal in CARs [2]. Although T cells transduced to express such constructs showed positive results in vitro, they have been found to have limited performance in eliminating tumor cells in clinical trials. The main limitation has been the relative inability to prolong and expand the T cells population and achieve sustained antitumor effects in vivo.

To address these problems, a co-stimulation domain (e.g. CD137, CD28 or CD134) is included in second generation CARs to achieve full, prolonged activation of T cells. Addition of a co-stimulation domain enhances the in vivo proliferation and survival of T cells containing CARs, and initial clinical data have shown that such constructs are a promising therapeutic agent in the treatment of tumors [3].

Although use of CAR-expressing T cells as an immunotherapeutic agent shows promise, there remain several challenges to overcome in order to achieve significant clinical outcomes. First, 'off-target' toxicities may result due to the fact that it is difficult to target only cancer cells via tumor-associated antigens because in many cases normal cells also express the tumor-associated antigen. For example, CD19 is a tumor-associated antigen that is expressed on malignant B cells. CARs containing anti-CD19 antibody were generated and used treated to patients. Although remission of malignant B cells was found, normal B cells were depleted in the patients as well because normal B cells also express CD19 [4]. Another example pertains to carbonic anhydrase IX (CAIX) which is overexpressed in clear cell renal carcinoma. Liver toxicity was found in subjects of the first clinical trial using CAR-targeting CAIX, likely due to the fact that CAIX is also expressed in bile duct epithelial cells and as such, the T cells targeted normal tissue as well [5].

Second, 'unregulated CAR activity' may be found where the rapid eradication of cancer cells by CARs induces a constellation of metabolic disturbances, called tumor lysis syndrome or a cytokine storm, which can be a fatal consequence to patients [1, 4, 6]. This is a result because transduced T cells expressing CARs cannot be easily regulated. Once transduced T cells are infused to patients, it is currently very difficult to regulate or control the activation of the cells.

Therefore, while CAR-expressing T cells show great promise as a tool in the treatment of cancer, the next generation of the CAR system is needed that provides reduced off-target toxicity and greater control of activation. The present invention is directed to this and other important ends.

BRIEF SUMMARY

The invention relates to a Chimeric Antigen Receptor (CAR) system and methods for using the system in the treatment of subjects with cancer. The CAR system of the present invention includes cytotoxic lymphocytes expressing CARs that target a moiety that is not produced or expressed by cells of the subject being treated. This CAR system thus allows for focused targeting of the cytotoxic lymphocytes to target cells, such as cancer cells. The targeted moiety is part of a small conjugate molecule (SCM) that also comprises a ligand of a tumor cell receptor. Administration of a SCM along with the CAR-expressing cytotoxic lymphocytes results in the targeting of the cytotoxic lymphocyte response to only those cells expressing the tumor receptor to which the SCM is bound.

In a first embodiment, the invention is directed to CAR-expressing cytotoxic lymphocytes. The CAR is a fusion protein comprising a recognition region, at least one co-stimulation domain, and an activation signaling domain. The CAR has binding specificity for a selected targeted moiety or can be bound by a targeted moiety.

In certain aspects of this embodiment, the recognition region of the CAR is a single chain fragment variable (scFv) region of an antibody with binding specificity for the targeted moiety. In a particular aspect, the recognition region of the CAR is a single chain fragment variable (scFv) region of an anti-FITC antibody.

In certain aspects of this embodiment, the co-stimulation domain of the CAR is selected from the group consisting of CD28, CD137 (4-1BB), CD134 (OX40), and CD278 (ICOS).

In certain aspects of this embodiment, the activation signaling domain of the CAR is the T cell CD3ζ chain or Fc receptor γ.

In certain aspects of this embodiment, the cytotoxic lymphocytes are one or more of cytotoxic T cells, natural killer (NK) cells, and lymphokine-activated killer (LAK) cells.

In a particular aspect of this embodiment, the recognition region is a single chain fragment variable (scFv) region of an anti-FITC antibody, the co-stimulation domain is CD137 (4-1BB), and the activation signaling domain is the T cell CD3ζ chain.

In certain aspects of this embodiment, the targeted moiety is a molecule selected from the group consisting of 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester (PFP), tetrafluorophenyl ester (TFP), a knottin, a centyrin, and a DARPin.

In certain aspects of this embodiment, the binding specificity of the CAR for the targeted moiety has an affinity of at least about 100 pM.

In a second embodiment, the invention is directed to small conjugate molecules (SCM) comprising a targeted moiety conjugated to a tumor receptor ligand, wherein the tumor receptor ligand is folate, 2-[3-(1,3-dicarboxypropyl)ureido]pentanedioic acid (DUPA), or cholecystokinin 2 receptor (CCK2R) ligand.

Targeted moieties that may be used in the SCMs of the invention include, but are not limited to, 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester (PFP), tetrafluorophenyl ester (TFP), a knottin, a centyrin, and a DARPin.

In certain aspects of this embodiment, the targeted moiety and the ligand are conjugated via a linker domain. Linker domains include, but are not limited to, polyethylene glycol (PEG), polyproline, a hydrophilic amino acid, a sugar, an unnatural peptideoglycan, polyvinylpyrrolidone, and pluronic F-127. In a particular aspect, the linker domain is $(PEG)_{12}$.

In certain aspects of this embodiment, the targeted moiety is FITC.

In certain aspects of this embodiment, the targeted moiety is FITC and the linker is $(PEG)_{12}$.

In particular aspects of this embodiment, the SCM is FITC-folate, FITC-DUPA, FITC-CCK2R ligand, FITC-$(PEG)_{12}$-folate, FITC-$(PEG)_{12}$-DUPA, or FITC-$(PEG)_{12}$-CCK2R ligand.

In a third embodiment, the invention is directed to a two component cancer therapeutic comprising:
(a) a small conjugate molecule (SCM) comprising a targeted moiety conjugated to a tumor receptor ligand, wherein the tumor receptor ligand is folate, DUPA, or CCK2R ligand; and
(b) chimeric antigen receptor (CAR)-expressing cytotoxic lymphocytes, wherein the CAR is a fusion protein comprising a recognition region, a co-stimulation domain and an activation signaling domain, and wherein the CAR has binding specificity for the targeted moiety.

Targeted moieties that may be used in the SCMs include, but are not limited to, 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester (PFP), tetrafluorophenyl ester (TFP), a knottin, a centyrin, and a DARPin.

In certain aspects of this embodiment, the targeted moiety and the ligand are conjugated via a linker domain. Linker domains include, but are not limited to, polyethylene glycol (PEG), polyproline, a hydrophilic amino acid, a sugar, an unnatural peptideoglycan, polyvinylpyrrolidone, and pluronic F-127. In a particular aspect, the linker domain is $(PEG)_{12}$.

In certain aspects of this embodiment, the targeted moiety is FITC.

In certain aspects of this embodiment, the targeted moiety is FITC and the linker is $(PEG)_{12}$.

In particular aspects of this embodiment, the SCM is FITC-folate, FITC-DUPA, FITC-CCK2R ligand, FITC-$(PEG)_{12}$-folate, FITC-$(PEG)_{12}$-DUPA, or FITC-$(PEG)_{12}$-CCK2R ligand.

In certain aspects of this embodiment, the recognition region of the CAR is a single chain fragment variable (scFv) region of an antibody with binding specificity for the targeted moiety. In a particular aspect, the recognition region of the CAR is a single chain fragment variable (scFv) region of an anti-FITC antibody.

In certain aspects of this embodiment, the co-stimulation domain of the CAR is CD28, CD137 (4-1BB), CD134 (OX40), or CD278 (ICOS).

In certain aspects of this embodiment, the activation signaling domain of the CAR is the T cell CD3ζ chain or Fc receptor γ.

In certain aspects of this embodiment, the cytotoxic lymphocytes are one or more of cytotoxic T cells, natural killer (NK) cells, and lymphokine-activated killer (LAK) cells.

In a particular aspect of this embodiment, the recognition region is a single chain fragment variable (scFv) region of an anti-FITC antibody, the co-stimulation domain is CD137 (4-1BB), and the activation signaling domain is the T cell CD3ζ chain.

In certain aspects of this embodiment, the binding specificity of the CAR for the targeted moiety is an affinity of at least about 100 pM.

In a fourth embodiment, the invention is directed to a method of treating cancer in a subject. In a first aspect the method comprises:
(a) culturing a population of cytotoxic lymphocytes under conditions promoting activation;
(b) transfecting the lymphocyte population of (a) with a vector encoding a chimeric antigen receptor (CAR), wherein the CAR is a fusion protein comprising a recognition region, a co-stimulation domain and an activation signaling domain;
(c) administering a therapeutically effective number of the transfected lymphocytes of (b) to a subject having cancer; and
(d) administering a small conjugate molecule (SCM) comprising a targeted moiety conjugated to a tumor receptor ligand to the subject, wherein the ligand is recognized and bound by a receptor on the surface of a cell of the cancer, and wherein the CAR has binding specificity for the targeted moiety or can be bound by the targeted moiety;
thereby treating cancer in a subject.

In a related embodiment the method comprises:
(a) culturing a population of cytotoxic lymphocytes under conditions promoting activation;
(b) transfecting the lymphocyte population of (a) with a vector encoding a chimeric antigen receptor (CAR), wherein the CAR is a fusion protein comprising a recognition region, a co-stimulation domain and an activation signaling domain;
(c) administering a small conjugate molecule (SCM) comprising a targeted moiety conjugated to a tumor receptor ligand to a subject having cancer, wherein the ligand is recognized and bound by a receptor on the surface of a cell of the cancer; and
(d) administering a therapeutically effective number of the transfected T cells of (b) to the subject, and wherein the CAR has binding specificity for the targeted moiety or can be bound by the targeted moiety;

thereby treating cancer in a subject.

In a further related embodiment the method comprises:

(a) culturing a population of cytotoxic lymphocytes under conditions promoting activation;

(b) transfecting the lymphocytes population of (a) with a vector encoding a chimeric antigen receptor (CAR), wherein the CAR is a fusion protein comprising a recognition region, a co-stimulation domain and an activation signaling domain, and wherein the CAR has binding specificity for a targeted moiety or can be bound by the targeted moiety;

(c) incubating the lymphocytes of (b) with a small conjugate molecule (SCM) comprising a targeted moiety conjugated to a tumor receptor ligand;

(d) administering a therapeutically effective number of the transfected lymphocytes of (c) to a subject having cancer;

thereby treating cancer in a subject.

In these three related embodiments the cytotoxic lymphocytes may be autologous or heterologous cells, with respect to the subject being treated, or a combination of both.

In these three related embodiments the culturing conditions of (a) may comprise culturing the population of lymphocytes in the presence of anti-CD3ζ antibodies or anti-CD28 antibodies, or both.

In certain aspects of these three related embodiments, the recognition region of the CAR is a single chain fragment variable (scFv) region of an antibody with binding specificity for the targeted moiety. In a particular aspect, the recognition region of the CAR is a single chain fragment variable (scFv) region of an anti-FITC antibody.

In certain aspects of these three related embodiments, the co-stimulation domain of the CAR is CD28, CD137 (4-1BB), CD134 (OX40), or CD278 (ICOS).

In certain aspects of these three related embodiments, the activation signaling domain of the CAR is the T cell CD3ζ chain or Fc receptor γ.

In certain aspects of these three related embodiments, the cytotoxic lymphocytes are one or more of cytotoxic T cells, natural killer (NK) cells, and lymphokine-activated killer (LAK) cells.

In certain aspects of these three related embodiments, the recognition region is a single chain fragment variable (scFv) region of an anti-FITC antibody, the co-stimulation domain is CD137 (4-1BB), and the activation signaling domain is the T cell CD3ζ chain.

In certain aspects of these three related embodiments, the targeted moiety is a molecule selected from the group consisting of 2,4-dinitrophenol (DNP), 2,4,6-trinitrophenol (TNP), biotin, digoxigenin, fluorescein, fluorescein isothiocyanate (FITC), NHS-fluorescein, pentafluorophenyl ester (PFP), tetrafluorophenyl ester (TFP), a knottin, a centyrin, and a DARPin. In a particular aspect, the targeted moiety is FITC.

In certain aspects of these three related embodiments, the ligand is folate, DUPA, CCK2R ligand.

In certain aspects of these three related embodiments, the targeted moiety and the ligand are conjugated via a linker domain. The linker domain may be, for example, polyethylene glycol (PEG), polyproline, a hydrophilic amino acid, a sugar, an unnatural peptideoglycan, polyvinylpyrrolidone, or pluronic F-127.

In certain aspects of these three related embodiments, the targeted moiety is FITC and the linker is $(PEG)_{12}$.

In certain aspects of these three related embodiments, the vector is a lentivirus vector.

In certain aspects of these three related embodiments, the binding specificity of the CAR for the targeted moiety is an affinity of at least about 100 pM.

In certain aspects of these three related embodiments, the subject is a human.

In certain embodiments of these three related embodiments, the cancer is one or more of a cancer of the brain, thyroid, lung, pancreas, kidney, stomach, gastrointestinal stroma, endometrium, breast, cervix, ovary, colon, prostate, leukemias, lymphomas, other blood-related cancers or head and neck cancer.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

FIG. 2 shows confocal microscopy of copGFP expression in transduced T cells containing CAR 4-1BBZ (top row) and FITC-folate binding on CAR-1BBZ transduced T cells (middle row). The bottom row shows the same view in the absence of fluorescence.

FIG. 3A shows the binding of FITC-Folate conjugates to KB cancer cells. FIG. 3B shows the binding of FITC-Folate conjugates to L1210A cancer cells. FIG. 3C shows the binding of FITC-$(PEG)_{12}$-Folate conjugates to KB cancer cells. FIG. 3D shows the binding of FITC-(PEG)$_{12}$-Folate conjugates to L1210A cancer cells. The competitor was 50× excess folate acid.

FIG. 5 shows an illustrative synthetic scheme.

DETAILED DESCRIPTION

I. Definitions

Figure 1A:
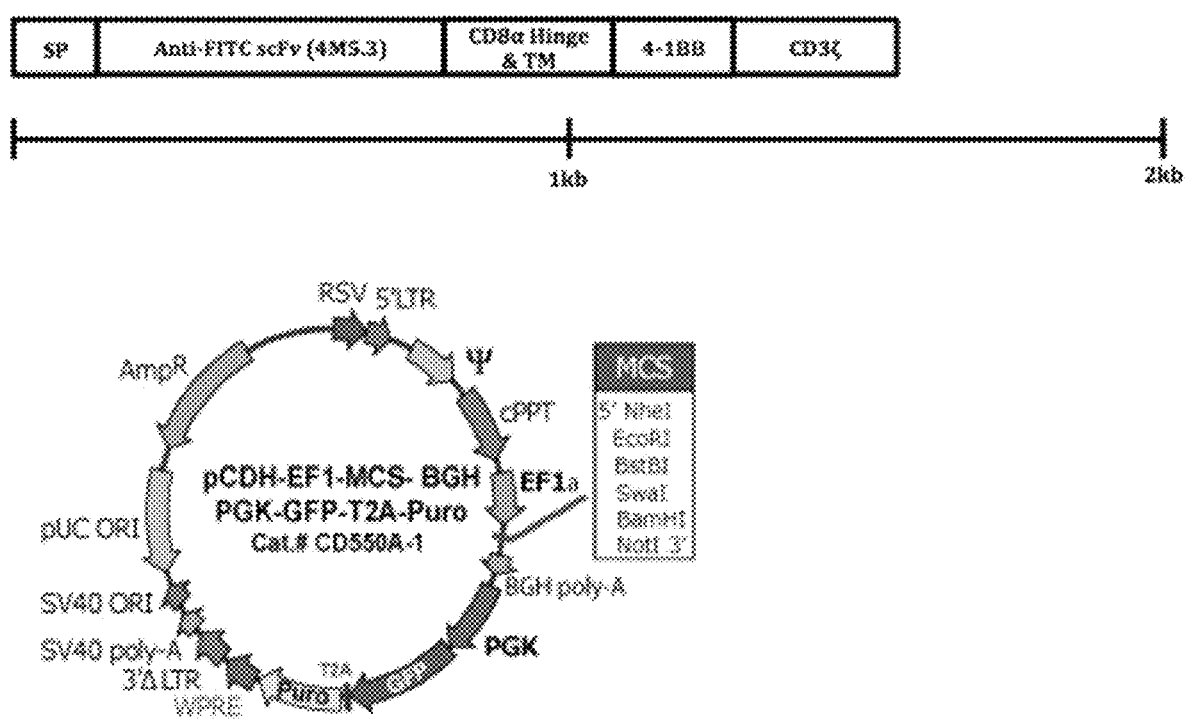
FIG. 1A is a schematic showing the CAR4-1BBZ construct.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, "treat" and all its forms and tenses (including, for example, treat, treating, treated, and treatment) refer to both therapeutic treatment and prophylactic or preventative treatment.

II. The Present Invention

The present invention is directed to a CAR system for use in the treatment of subjects with cancer. The CAR system of the present invention (e.g., cytotoxic lymphocytes expressing novel CARs and cognate small conjugate molecules (SCM)) makes use of CARs that target a moiety that is not produced or expressed by cells of the subject being treated. This CAR system thus allows for focused targeting of the cytotoxic lymphocytes to target cells, such as cancer cells. The targeted moiety is part of a small conjugate molecule (SCM) that also comprises a ligand of a tumor cell receptor. Because small organic molecules are typically used as the targeted moiety, clearance of the SCM from the bloodstream can be achieved within about 20 minutes. By administration of a SCM along with the CAR-expressing cytotoxic lymphocytes, the lymphocyte response can be targeted to only those cells expressing the tumor receptor, thereby reducing off-target toxicity, and the activation of lymphocytes can be more easily controlled due to the rapid clearance of the SCM. As an added advantage, the CAR-expressing lymphocytes can be used as a "universal" cytotoxic cell to target a wide variety of tumors without the need to prepare separate CAR constructs. The targeted moiety recognized by the CAR may also remain constant. It is only the ligand portion of the SCM that needs to be altered to allow the system to target cancer cells of different identity.

One embodiment of the invention provides an illustration of this novel CAR system. In this embodiment, and as a first component, a SCM is prepared that comprises FITC linked to a ligand of a selected tumor cell receptor. As a second component, cytotoxic T cells are transduced to express a CAR that comprises anti-FITC scFv. This CAR thus targets Fluorescein Isothiocyanate (FITC) instead of a tumor-associated antigen that might also be expressed by healthy, non-target cells. The two components are administered to a subject having cancer and the FITC-SCM (first component) is bound by the target tumor cells (through binding of the ligand portion of the molecule to cognate tumor cell receptor). The FITC portion of the SCM is then recognized and bound by the anti-FITC CAR expressed by the T cells (second component). Upon FITC binding, the anti-FITC CAR-expressing T cells are activated and the tumor cell is killed. As will be apparent to the skilled artisan, the cytotoxic T cells cannot kill cells with first binding to a tumor cell. As it will be further apparent, T cells will not bind to non-target cells because the recognition region of the CAR will only recognize and bind FITC, which is not produce or expressed by cells of the subject. The SCM thus acts as a bridge between the cytotoxic T cells and the target tumor cells. As long as the targeted moiety of the SCM is a moiety not found in the host, the activity of the T cells can be limited to the target cells. Further, the activation of the CAR-expressing T cells can be regulated by limiting the amount of SCM administered to a subject, for example, by manipulating infusion of the small conjugate molecule if a side effect is detected. Thus, the CAR system of the present invention overcomes problems associated with conventional CAR therapy.

Small Conjugate Molecules (SCM)

The CAR system of the present invention utilizes small conjugate molecules (SCMs) as the bridge between cytotoxic lymphocytes and targeted cancer cells. The SCMs are conjugates comprising a targeted moiety on one end of the molecule and a tumor receptor ligand on the other, optionally connected by a bridge domain. The targeted moiety is a molecule that is recognized by a CAR of a transduced lymphocyte or that can bind to a region of the CAR. The identity of the targeted moiety is limited only in that it must be a molecule that can be recognized and bound by CAR expressed by a lymphocyte, or recognized and bind the CAR itself, in both cases preferably with specificity, and that it have a relatively low molecular weight. Exemplary targeted moieties are haptens that can be recognized and bound by CARs and include small molecular weight organic molecules such as DNP (2,4-dinitrophenol), TNP (2,4,6-trinitrophenol), biotin, and digoxigenin, along with fluorescein and derivatives thereof, including FITC (fluorescein isothiocyanate), NHS-fluorescein, and pentafluorophenyl ester (PFP) and tetrafluorophenyl ester (TFP) derivatives. Suitable targeted moieties that themselves bind to one or more regions of a CAR include knottins [16], centyrins and DARPins [7].

The tumor receptor ligands that comprise the SCMs of the present invention are molecules recognized and bound by receptors expressed by target tumor cells, typically expressed on the surface of the tumor cells. Suitable ligands include: 1) DUPA (DUPA-(99m)Tc), a ligand bound by PSMA-positive human prostate cancer cells with nanomolar affinity ($K_D$=14 nM; [8]); 2) CCK2R ligand, a ligand bound by CCK2R-positive cancer cells (e.g., cancers of the thyroid, lung, pancreas, ovary, brain, stomach, gastrointestinal stroma, and colon; [9]); 3) folate, a ligand bound by the folate receptor on cells of cancers that include cancers of the ovary, cervix, endometrium, lung, kidney, brain, breast, colon, and head and neck cancers [10].

The targeted moiety and the ligand can be directly conjugated through such means as reaction between the isothiocyanate group of FITC and free amine group of small ligands (e.g. folate, DUPA and CCK2R ligand). However, the use of a linking domain to connect the two molecules can be helpful as it can provide flexibility and stability to the SMC depending on the identity of the components comprising the SCM. Examples of suitable linking domains include: 1) polyethylene glycol (PEG); 2) polyproline; 3) hydrophilic amino acids; 4) sugars; 5) unnatural peptideoglycans; 6) polyvinylpyrrolidone; 7) pluronic F-127. Linkers lengths that are suitable include, but are not limited to, linkers having 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40, or more atoms.

While the affinity at which the ligands and cancer cell receptors bind can vary, and in some cases low affinity binding may be preferable (such as about 1 µM), the binding affinity of the ligands and cancer cell receptors will generally be at least about 100 µM, 1 nM, 10 nM, or 100 nM, preferably at least about 1 pM or 10 pM, even more preferably at least about 100 pM.

The skilled artisan will understand and recognize that various means can be used to prepare SMCs comprised of a targeted moiety, a linking domain, and a ligand. Examples are provided in the Examples included herein.

Prior to being administered to a subject, the SCMs are prepared in a pharmaceutically acceptable formulation. Such formulations may contain a pharmaceutically acceptable carrier or diluent.

Exemplary SCMs included within the scope of the invention include the following molecules.

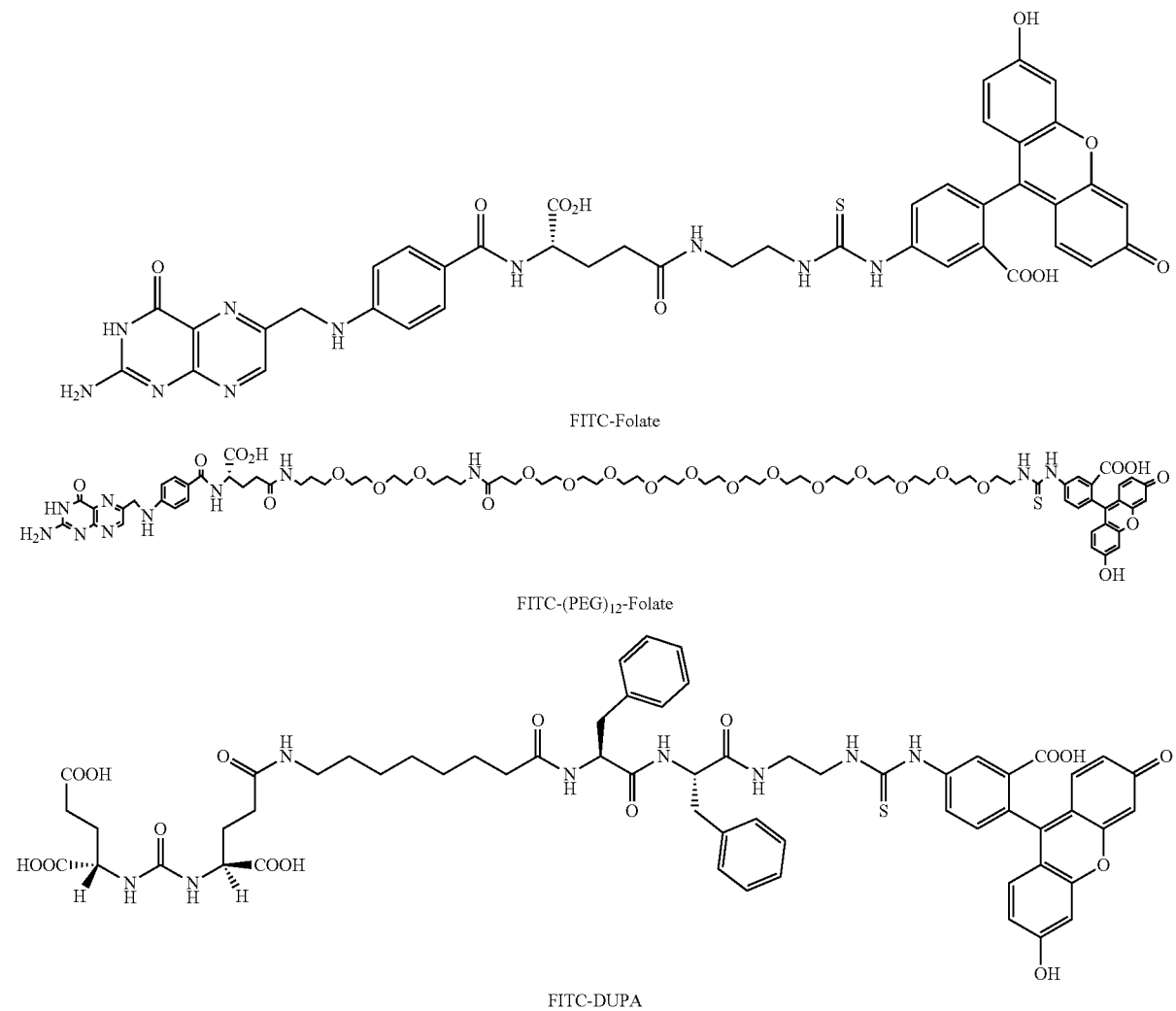

-continued

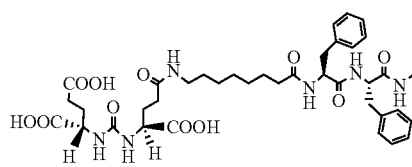

FITC-(PEG)₁₂-DUPA

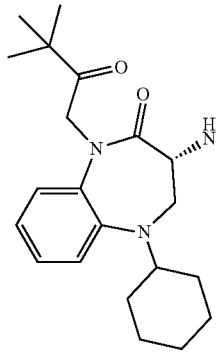

FITC-CCK2R ligand

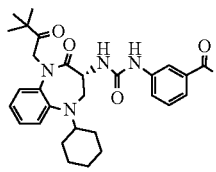

FITC-(PEG)₁₂-CCK2R ligand

Chimeric Antigen Receptors (CARs)

The CAR system of the present invention also utilizes cytotoxic lymphocytes engineered to express chimeric antigen receptors (CARs) that recognize and bind the targeting moiety of the SCMs. The CARs used in the CAR system comprise three domains. The first domain is the recognition region which, as the name suggests, recognizes and binds the targeting moiety. The second domain is the co-stimulation domain which enhances the proliferation and survival of the lymphocytes. The third domain is the activation signaling domain which is a cytotoxic lymphocyte activation signal. The three domains, together in the form of a fusion protein, comprise the CARs of the present invention.

As suggested above, the recognition region is the portion of a CAR that recognizes and binds a targeting moiety. The recognition regions comprising the CARs of the present invention are single chain fragment variable (scFv) regions of antibodies that bind the targeted moiety. Preferably, the scFv regions bind the targeted moiety with specificity. The identity of the antibody used in the production of the recognition region is limited only in that it binds the targeted moiety of the SCM. Thus, as non-limiting examples, scFv regions of antibodies that bind one of the following targeted moieties are included within the scope of the invention: DUPA, CCK2R ligand, folate. The scFv regions can be prepared from (i) antibodies known in the art that bind a targeted moiety, (ii) antibodies newly prepared using a selected targeted moiety as a hapten, and (iii) sequence variants derived from the scFv regions of such antibodies, e.g., scFv regions having at least about 80% sequence identity to the amino acid sequence of the scFv region from which they are derived. The use of unaltered (i.e., full size) antibodies, such as IgG, IgM, IgA, IgD or IgE, in the CAR or as the CAR is excluded from the scope of the invention.

The co-stimulation domain serves to enhance the proliferation and survival of the cytotoxic lymphocytes upon binding of the CAR to a targeted moiety. The identity of the co-stimulation domain is limited only in that it has the ability to enhance cellular proliferation and survival activation upon binding of the targeted moiety by the CAR. Suitable co-stimulation domains include: 1) CD28 [11]; 2) CD137 (4-1BB), a member of the tumor necrosis factor (TNF) receptor family [12]; 3) CD134 (OX40), a member of the TNFR-superfamily of receptors [13]; 4) CD278 (ICOS), a CD28-superfamily co-stimulatory molecule expressed on activated T cells [14]. The skilled artisan will understand that sequence variants of these noted co-stimulation domains can be used without adversely impacting the invention, where the variants have the same or similar activity as the domain on which they are modeled. Such variants will have at least about 80% sequence identity to the amino acid sequence of the domain from which they are derived.

In some embodiments of the invention, the CAR constructs comprise two co-stimulation domains. While the particular combinations include all possible variations of the four noted domains, specific examples include: 1) CD28+ CD137 (4-1BB) and 2) CD28+CD134 (OX40).

The activation signaling domain serves to activate cytotoxic lymphocytes upon binding of the CAR to a targeted moiety. The identity of the activation signaling domain is limited only in that it has the ability to induce activation of the selected cytotoxic lymphocyte upon binding of the targeted moiety by the CAR. Suitable activation signaling domains include the T cell CD3ζ chain and Fc receptor γ. The skilled artisan will understand that sequence variants of these noted activation signaling domains can be used without adversely impacting the invention, where the variants have the same or similar activity as the domain on which they are modeled. Such variants will have at least about 80% sequence identity to the amino acid sequence of the domain from which they are derived.

Constructs encoding the CARs of the invention are prepared through genetic engineering. As an example, a plasmid or viral expression vector can be prepared that encodes a fusion protein comprising a recognition region, one or more co-stimulation domains, and an activation signaling domain, in frame and linked in a 5' to 3' direction. However, the CARs of the present invention are not limited in this arrangement and other arrangements are acceptable and include: (i) a recognition region, an activation signaling domain, and one or more co-stimulation domains, and (ii) a recognition region, a co-stimulation domain, and an activation signaling domain, linked in a 5' to 3' direction. It will be understood that because the recognition region must be free to bind the targeted moiety, the placement of the recognition region in the fusion protein will generally be such that display of the region on the exterior of the cell is achieved. In the same manner, because the co-stimulation and activation signaling domains serve to induce activity and proliferation of the cytotoxic lymphocytes, the constructs will generally encode a fusion protein that displays these two domains in the interior of the cell.

The CARs may include additional elements, such a signal peptide to ensure proper export of the fusion protein to the cells surface, a transmembrane domain to ensure the fusion protein is maintained as an integral membrane protein, and a hinge domain that imparts flexibility to the recognition region and allows strong binding to the targeted moiety.

An example of an exemplary CAR of the present invention is shown in FIG. 1A where the fusion protein is encoded by a lentivirus expression vector and where "SP" is a signal peptide, the CAR is an anti-FITC CAR, a CD8a hinge is present, a transmembrane domain is present ("TM"), the co-stimulation domain is 4-1BB, and the activation signaling domain is CD3ζ. The sequence of the CAR-encoding vector is provided as SEQ ID NO:1.

In addition to the use of plasmid and viral vectors, cytotoxic lymphocytes can be engineered to express CARs of the invention through retrovirus, lentivirus (viral mediated CAR gene delivery system), sleeping beauty, and piggyback (transposon/transposase systems that include a non-viral mediated CAR gene delivery system).

While the affinity at which the CARs, expressed by the cytotoxic lymphocytes, bind to the targeted moiety can vary, and in some cases low affinity binding may be preferable (such as about 50 nM), the binding affinity of the CARs to the targeted ligand will generally be at least about 100 nM, 1 pM, or 10 pM, preferably at least about 100 pM, 1 fM or 10 fM, even more preferably at least about 100 fM.

CAR-Expressing Cytotoxic Lymphocytes

The cells used in the CAR system of the present invention are cytotoxic lymphocytes selected from (i) cytotoxic T cells (also variously known as cytotoxic T lymphocytes, CTLs, T killer cells, cytolytic T cells, CD8$^+$ T cells, and killer T cells), natural killer (NK) cells, and lymphokine-activated killer (LAK) cells. Upon activation, each of these cytotoxic lymphocytes triggers the destruction of target tumor cells. For example, cytotoxic T cells trigger the destruction of target tumor cells by either or both of the following means. First, upon activation T cells release cytotoxins such as perforin, granzymes, and granulysin. Perforin and granulysin create pores in the target cell, and granzymes enter the cell and trigger a caspase cascade in the cytoplasm that induces apoptosis (programmed cell death) of the cell. Second, apoptosis can be induced via Fas-Fas ligand interaction between the T cells and target tumor cells.

The cytotoxic lymphocytes will preferably be autologous cells, although heterologous cells can also be used, such as when the subject being treated using the CAR system of the invention has received high-dose chemotherapy or radiation treatment to destroy the subject's immune system. Under such circumstances, allogenic cells can be used.

The cytotoxic lymphocytes can be isolated from peripheral blood using techniques well known in the art, include Ficoll density gradient centrifugation followed by negative selection to remove undesired cells.

Cytotoxic lymphocytes can be engineered to express CAR constructs by transfecting a population of lymphocytes with an expression vector encoding the CAR construct. Appropriates means for preparing a transduced population of lymphocytes expressing a selected CAR construct will be well known to the skilled artisan, and includes retrovirus, lentivirus (viral mediated CAR gene delivery system), sleeping beauty, and piggyback (transposon/transposase systems that include a non-viral mediated CAR gene delivery system), to name a few examples.

Transduced cytotoxic lymphocytes are grown in conditions that are suitable for a population of cells that will be introduced into a subject such as a human. Specific considerations include the use of culture media that lacks any animal products, such as bovine serum. Other considerations include sterilized-condition to avoid contamination of bacteria, fungi and mycoplasma.

Prior to being administered to a subject, the cells are pelleted, washed, and resuspended in a pharmaceutically acceptable carrier or diluent. Exemplary formulations comprising CAR-expressing cytotoxic lymphocytes include formulations comprising the cells in sterile 290 mOsm saline, infusible cryomedia (containing Plasma-Lyte A, dextrose, sodium chloride injection, human serum albumin and DMSO), 0.9% NaCl with 2% human serum albumin or any other sterile 290 mOsm infusible materials.

Methods of Treatment

The CAR system of the present invention can be used in the treatment of a subject having cancer. The methods of treatment encompassed by the invention generally includes the steps of (i) obtaining a population of autologous or heterologous cytotoxic lymphocytes, (ii) culturing the lymphocytes under conditions that promote the activation of the cells, (iii) transfecting the lymphocytes with an expression vector encoding a CAR, (iv) administering a formulation comprising the transfected lymphocytes to a subject having cancer, and (v) administering a formulation comprising SCM to the subject.

The invention also includes variations on this theme such, as administering the formulation comprising SMC to the subject before the formulation comprising the transfected lymphocytes, or at the same time as the formulation comprising the transfected lymphocytes. A further variation includes culturing the formulation comprising the transfected lymphocytes with the SCM prior to administration to the subject.

The population of cytotoxic lymphocytes can be obtained from a subject by means well known in the art. For example, cytotoxic T cells can be obtained by collecting peripheral blood from the subject, subjecting the blood to Ficoll density gradient centrifugation, and then using a negative T cell isolation kit (such as EasySep™ T Cell Isolation Kit) to isolate a population of cytotoxic T cells from the blood. While the population of cytotoxic lymphocytes need not be pure and may contain other blood cells such as T cells, monocytes, macrophages, natural killer cells and B cells, depending of the population being collected, preferably the population comprises at least about 90% of the selected cell type. In particular aspects, the population comprises at least about 90%, 91%, 92%, 93%, 94%, 95%, 96%, 97%, 98%, 99%, or even 100% of the selected cell type. As indicated earlier, the population of cells may come from the subject to be treated, from one or more different subjects, or the population may be a combination of cells from the subject to be treated and one or more different subjects.

After the population of cytotoxic lymphocytes is obtained, the cells are cultured under conditions that promote the activation of the cells. The culture conditions will be such that the cells can be administered to a subject without concern for reactivity against components of the culture. For example, when the population will be administered to a human, the culture conditions will not include bovine serum products, such as bovine serum albumin. The activation of the lymphocytes in the culture can be achieved by introducing known activators into the culture, such as anti-CD3 antibodies in the case of cytotoxic T cells. Other suitable activators include anti-CD28 antibodies. The population of lymphocytes will generally be cultured under conditions promoting activation for about 1 to 4 days. The appropriate level of cellular activation can be determined by cell size, proliferation rate or activation markers by flow cytometry.

After the population of cytotoxic lymphocytes has been cultured under conditions promoting activation, the cells are transfected with an expression vector encoding a CAR. Such vectors are described above, along with suitable means of transfection. After transfection, the resulting population of cells can be immediately administered to a subject or the cells can be culture for at least about 1, 2, 3, 4, 5, 6, 7, 8, 9, 10, 11, 12, 13, 14, 15, 16, 17, 18 or more days, or between about 5 and 12 days, between about 6 and 13 days, between about 7 and 14 days, or between about 8 and 15 days, for example, to allow time for the cells to recover from the transfection. Suitable culture conditions with be the same as those conditions under which the cells were culture while activation was being promoted, either with or without the agent that was used to promote activation and expansion.

When the transfected cells are ready a formulation comprising the cells is prepared and administered to a subject having cancer. Prior to administration, the population of cells can be washed and resuspended in a pharmaceutically acceptable carrier or diluent to form the formulation. Such carriers and diluents include, but are not limited to, sterile 290 mOsm saline, infusible cryomedia (containing Plasma-Lyte A, dextrose, sodium chloride injection, human serum albumin and DMSO), 0.9% NaCl with 2% human serum albumin or any other sterile 290 mOsm infusible materials. Alternatively, depending on the identity of the culture media used in the previous step, the cells can be administered in the culture media as the formulation, or concentrated and resuspended in the culture media before administration. The formulation can be administered to the subject via suitable means, such as parenteral administration, e.g., intradermally, subcutaneously, intramuscularly, intraperitoneally, intravenously, or intrathecally.

The total number of cells and the concentration of cells in the formulation administered to a subject will vary depending on a number of factors including the type of cytotoxic lymphocytes being used, the binding specificity of the CAR, the identity of the targeted moiety and the ligand, the identity of the cancer or tumor to be treated, the location in the subject of the cancer or tumor, the means used to administer the formulations to the subject, and the health, age and weight of the subject being treated. However, suitable formulations comprising transduced lymphocytes include those having a volume of between about 5 ml and 200 ml, containing from about $1 \times 10^5$ to $1 \times 10^{15}$ transduced cells. Typical formulations comprise a volume of between about 10 ml and 125 ml, containing from about $1 \times 10^7$ to $1 \times 10^{10}$ transduced cells. An exemplary formulation comprises about $1 \times 10^9$ transduced cells in a volume of about 100 ml.

The final step in the method is the administration of a formulation comprising SCM to the subject. As described above, the SCM will be prepared in a formulation appropriate for the subject receiving the molecules. The concentration of SCM in a SCM formulation will vary depending on factors that include the binding specificity of the CAR, the identity of the targeted moiety and the ligand, the identity of the cancer or tumor to be treated, the location in the subject of the cancer or tumor, the means used to administer the formulations to the subject, and the health, age and weight of the subject being treated. However, suitable formulations comprising SCM include those having a volume of between about 1 ml and 50 ml and contain between about 20 ug/kg body weight and 3 mg/kg body weight SCM. Typical formulations comprise a volume of between about 5 ml and 20 ml and contain between about 0.2 mg/kg body weight and 0.4 mg/kg body weight SCM. An exemplary formulation comprises about 50 ug/kg body weight SCM in a volume of about 10 ml.

The timing between the administration of transduced lymphocyte formulation and the SCM formation may range widely depending on factors that include the type of cytotoxic lymphocytes being used, the binding specificity of the CAR, the identity of the targeted moiety and the ligand, the identity of the cancer or tumor to be treated, the location in the subject of the cancer or tumor, the means used to administer the formulations to the subject, and the health, age and weight of the subject being treated. Indeed, the SCM formation may be administered prior to, simultaneous with, or after the lymphocyte formulation. In general, the SCM formation will be administered after the lymphocyte formulation, such as within 3, 6, 9, 12, 15, 18, 21, or 24 hours, or within 0.5, 1, 1.5, 2, 2.5, 3, 4 5, 6, 7, 8, 9, 10 or more days. When the SCM formation is administered before the lymphocyte formulation, the lymphocyte formulation will generally be administered within about 0.25, 0.5, 0.75, 1, 2, 3, 4, 5, 6, 7, 8, 9, 10, 11, 12 or more hours. When the SCM formation and the lymphocyte formulation are added simultaneously, it is preferable that the formations are not combined and thus administered separately to the subject.

Depending on the cancer being treatment the step of administering the lymphocyte formulation, or the step of administering the SCM formulation, or both, can be repeated one or more times. The particular number and order of the steps is not limited as the attending physician may find that a method can be practiced to the advantage of the subject using one or more of the following methodologies, or others not named here: (i) administering the lymphocyte formulation (A) followed by the SCM formulation (B), i.e., A then B; (ii) B then A; (iii) A then B then A then B; (iv) A then B then A; (v) B then A then B then A; (vi) A then A then B; (vii) B then A then A; (vii) B then B then A.

The formulations can be administered as single continuous doses, or they can be divided and administered as a multiple-dose regimen depending on the reaction (i.e., side effects) of the patient to the formulations.

The types of cancers which may be treated using the methods of the invention will be governed based on the identity of the ligand used in the SCM. When the ligands defined above are used (i.e., DUPA, CCK2R ligand, folate) cancers that may be treated using the CAR system and methods of the present invention generally include solid tumors, and more specifically include prostate cancer adenocarcinoma, hepatoma, colorectal liver metastasis, and cancers of neuroendocrine origin.

In each of the embodiments and aspects of the invention, the subject is a human, a non-human primate, bird, horse, cow, goat, sheep, a companion animal, such as a dog, cat or rodent, or other mammal.

III. Examples

1. Generation of CAR4-1BBZ and Transduction of Mouse T Cells to Express CAR

To generate modified T cells containing CAR that target cancer cells by FITC-ligand small molecule conjugates, CAR constructs were designed and generated as shown in FIG. 1.

A) Generation of Chimeric Antigen Receptor (CAR) in Lentiviral Vector

Figure 1B:
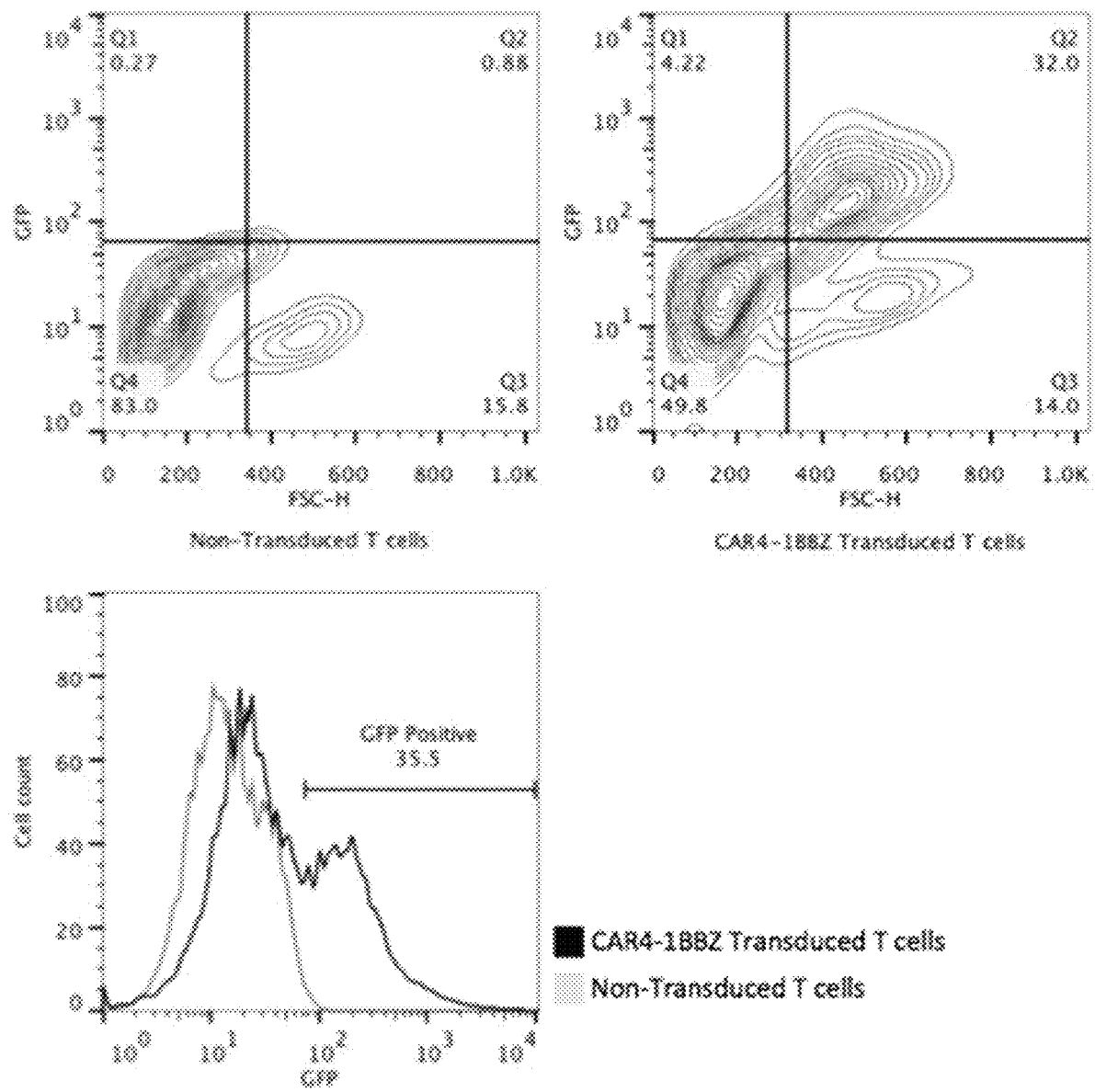
FIG. 1B shows the transduction efficiency into T cells of the CAR4-1BBZ construct. 96 h after transduction, the expression of CAR4-1BBZ was identified through copGFP expression by flow cytometry. As shown in the figure, approximately 30% of transduced T cells expressed CAR4-1BBZ.
Figure 1C:
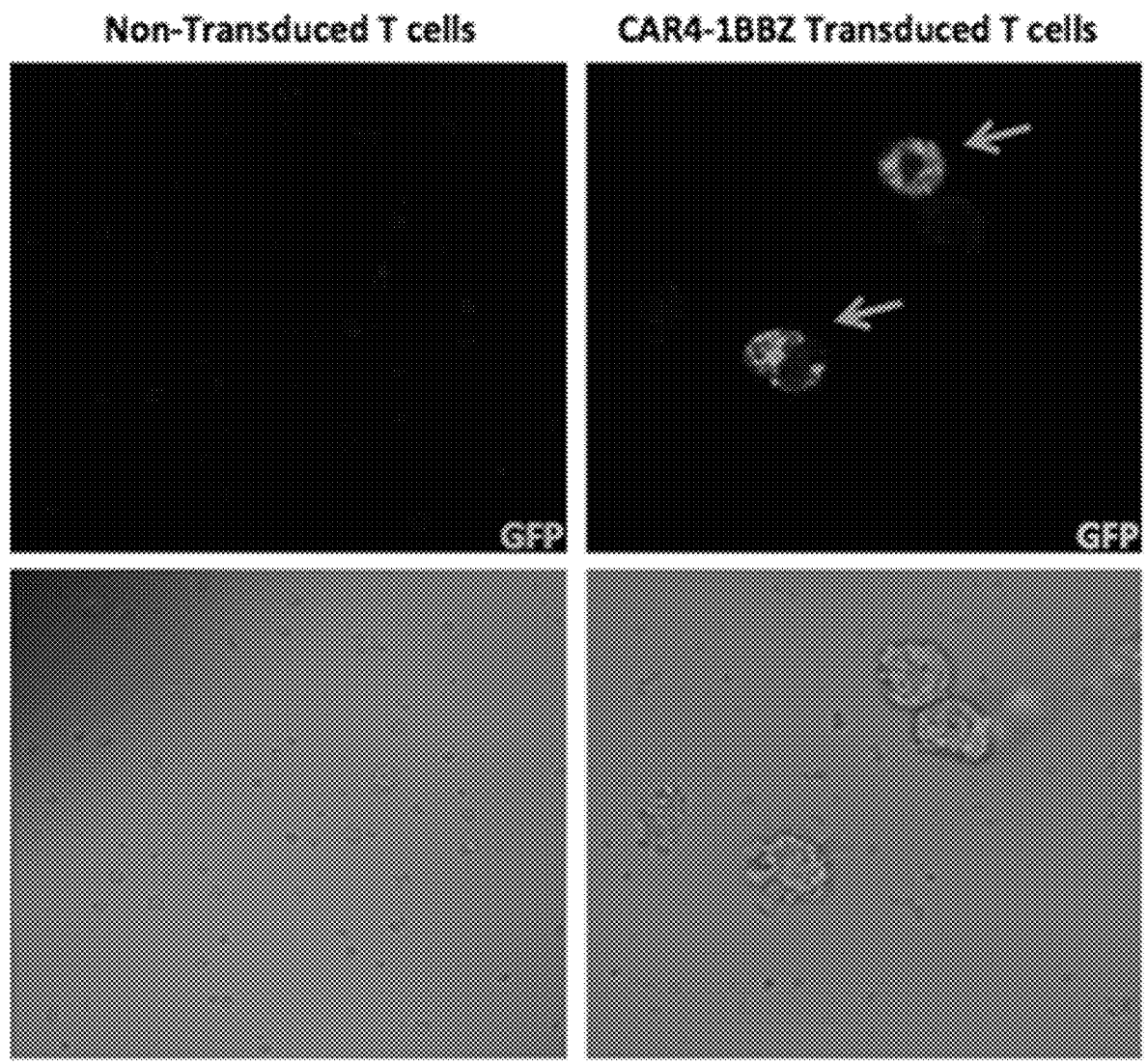
FIG. 1C shows the expression of CAR4-1BBZ on transduced T cells using confocal microscopy. copGFP was expressed on positive transduced T cells containing CAR4-1BBZ (arrows). However, copGFP expression was not detected on non-transduced T cells that do not express CAR4-1BBZ.

An overlap PCR method was used to generate CAR constructs comprising scFv against FITC (CAR4-1BBZ). scFV against FITC, 4M5.3 (Kd=270 fM, 762 bp) derived from anti-fluorescence (4-4-20) antibody, was synthesized based on a previous report [15]. As shown in FIG. 1, sequence encoding the mouse CD8a signal peptide (SP, 81 bp), the hinge and transmembrane region (207 bp), the cytoplasmic domain of 4-1BB (CD137, 144 bp) and the CD3ζ chain (339 bp) were fused with the anti-FITC scFV by overlapping PCR. The resulting CAR construct (CAR4-1BBZ) (1533 bp; SEQ ID NO:2) was inserted into NheI/NotI cleaved lentiviral expression vector pCDH-EF1-MCS-BGH-PGK-GFP-T2A-Puro (System Biosciences, Mountain View, CA). CAR4-1BBZ expression is regulated by EF1α promoter in the lentiviral vector. The sequence of CAR constructs in lentiviral vector (CAR4-1BBZ) was confirmed by DNA sequencing (Purdue Genomic Core Facility) and is provided in SEQ ID NO:1. copGFP expression encoded in the lentiviral vector was monitored to identify CAR4-1BBZ expression (FIG. 1C).

B) Isolation and Transduction of Mouse T Cells

T cells were isolated from mouse spleen or peripheral blood. To isolate T cells, mouse splenocytes and peripheral blood mononuclear cells (PBMC) were isolated by Ficoll density gradient centrifugation (GE Healthcare Lifesciences). After washing away remaining Ficoll solution, T cells were isolated by EasySep™ Mouse T Cell Isolation Kit (STEM CELL technologies). Purified T cells are cultured in RPMI 1640 with 10% heat inactivated fetal bovine serum (FBS), 1% penicillin and streptomycin sulfate, 10 mM HEPES. To prepare lentiviral virus containing CAR4-1BBZ, 293TN packaging cell line was co-transfected with CAR4-1BBZ lentiviral vector and packaging plasmids. After 48 and 72 hours transfection, supernatants containing CAR4-1BBZ lentivirus were harvested and virus particles were concentrated for transduction. For transduction of mouse T cells, isolated T cells were activated with Dynabeads coupled with anti-CD3/CD28 antibodies (Life Technologies) for 12-24 hours in the presence of mouse IL-2 (50 units/ml), then infected with lentiviral expression vector containing CAR4-1BBZ. Mouse IL-2 (50 units/ml) was provided every other day. After 96 hours, cells were harvested and the expression of CAR on transduced T cells was identified by flow cytometry. As shown in FIG. 1B, approximately 30% of transduced T cells expressed CAR4-1BBZ.

C) Flow Cytometry

The expression of CAR4-1BBZ on transduced T cells was determined by flow cytometry. Since lentiviral expression backbone also encodes copGFP expression, CAR4-1BBZ transduced T cells were verified by copGFP expression. FIG. 1C shows the expression of CAR4-1BBZ on transduced T cells. Transduced T cells were further confirmed by confocal microscope. copGFP was expressed on positive transduced T cells containing CAR4-1BBZ (arrows). However, copGFP expression was not detected on non-transduced T cells that do not express CAR4-1BBZ. Data was analyzed with FlowJo software.

Based on these result, it was evident that that the CAR4-1BBZ constructs was successfully transduced to mouse T cells and that the transduced T cells express CAR4-1BBZ.

D) Cell Culture

Two cancer cell lines were used in this study: L1210A and KB. L1210A is a murine leukemia cell line. KB is a human epidermoid carcinoma cell line. Both of them have higher folate receptor expression on cell surface.

L1210A and KB cells were cultured in folic acid-deficient RPMI medium, 10% of heat inactivated fetal bovine serum (FBS), 1% penicillin and streptomycin sulfate were included in the culture media.

2. Generation of Small Conjugate Molecules Comprising FITC and Ligands

A) Synthesis of FITC-Folate

Folate-γ-ethylenediamine was coupled to FITC isomer I (Sigma-Aldrich, St. Louis, MO) in anhydrous dimethylsulfoxide in the presence of tetramethylguanidine and diisopropylamine. The crude product was loaded onto an Xterra RP18 preparative HPLC column (Waters) and eluted with gradient conditions starting with 99% 5 mM sodium phosphate (mobile phase A, 047.4) and 1% acetonitrile (mobile phase B) and reaching 90% A and 10% B in 10 min at a flow rate of 20 mL/min. Under these conditions, the folate-FITC main peak typically eluted at 27-50 min. The quality of folate-FITC fraction was monitored by analytical reverse-phase HPLC with a UV detector. Fractions with greater than 98.0% purity (LCMS) were lyophilized to obtain the final folate-FITC product.

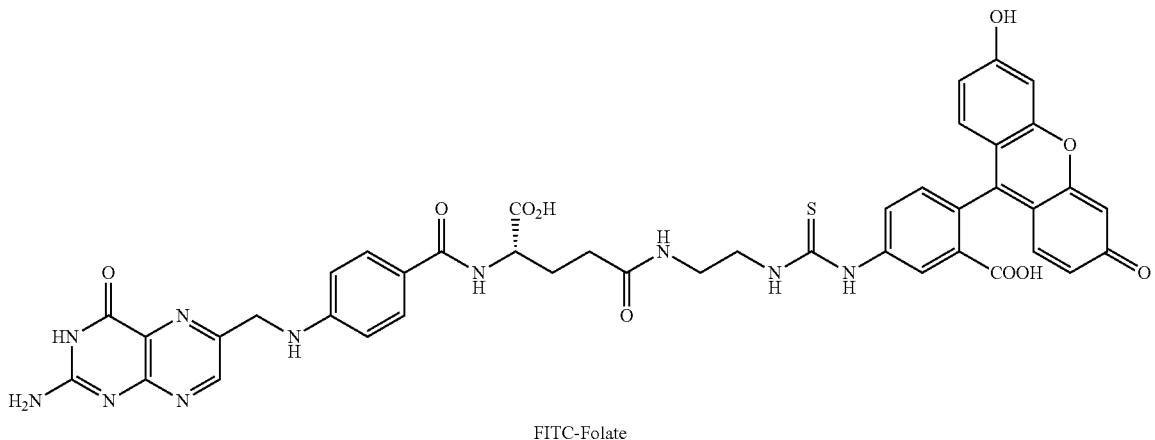 [SMILES: Nc1nc2ncc(CNc3ccc(C(=O)N[C@@H](CCC(=O)NCCNC(=S)Nc4ccc(-c5c6ccc(=O)cc-6oc6cc(O)ccc56)c(C(=O)O)c4)C(=O)O)cc3)nc2c(=O)[nH]1]

FITC-Folate

B) Synthesis of FITC-(PEG)$_{12}$-Folate

Universal PEG Nova Tag™ resin (0.2 g) was loaded into a peptide synthesis vessel and washed with i-PrOH (3×10 mL), followed by DMF (3×10 mL). Fmoc deprotection was carried out using 20% piperidine in DMF (3×10 mL). Kaiser tests were performed to assess reaction completion. To the vessel was then introduced a solution of Fmoc-Glu-(O-t-Bu)-OH (23.5 mg) in DMF, i-Pr$_2$NEt (4 equiv), and PyBOP (2 equiv). Fmoc deprotection was carried out using 20% piperidine in DMF (3×10 mL). To the vessel was then introduced a solution of N10-TFA-Pte-OH (22.5 mg), DMF, i-Pr$_2$NEt (4 equiv), and PyBOP (2 equiv). Argon was bubbled for 2 h, and resin was washed with DMF (3×3 mL) and i-PrOH (3×3 mL). After swelling the resin in DCM, a solution of 1M HOBT in DCM/TFE (1:1) (2×3 mL) was added for removal of Mmt group. Argon was bubbled for 1 h, the solvent was removed and resin was washed with DMF (3×3 mL) and i-PrOH (3×3 mL). After swelling the resin in DMF, a solution of Fmoc-NH-(PEG)$_{12}$-COOH (46.3 mg) in DMF, i-Pr$_2$NEt (4 equiv), and PyBOP (2 equiv) was added. Argon was bubbled for 2 h, and resin was washed with DMF (3×3 mL) and i-PrOH (3×3 mL). Fmoc deprotection was carried out using 20% piperidine in DMF (3×10 mL). Kaiser tests were performed to assess reaction completion. To the vessel was then introduced a solution of FITC (21.4 mg) in DMF, i-Pr$_2$NEt (4 equiv), then Argon was bubbled for 2 h, and resin was washed with DMF (3×3 mL) and i-PrOH (3×3 mL). Then to the vessel was added 2% NH$_2$NH$_2$ in DMF (2×2 mL). Final compound was cleaved from resin using a TFA:H$_2$O:TIS (95:2.5:2.5) and concentrated under vacuum. The concentrated product was precipitated in Et$_2$O and dried under vacuum. The crude product was purified by using preparative RP-HPLC (mobile phase: A=10 mM ammonium acetate pH=7, B=ACN; method: 0% B to 30% B in 30 min at 13 mL/min). The pure fractions were pooled and freeze-dried, furnishing the FITC-(PEG)$_{12}$-Folate. FIG. 5 shows the synthetic scheme.

C) Synthesis of FITC-(PEG)$_{12}$-DUPA

Figure 6:
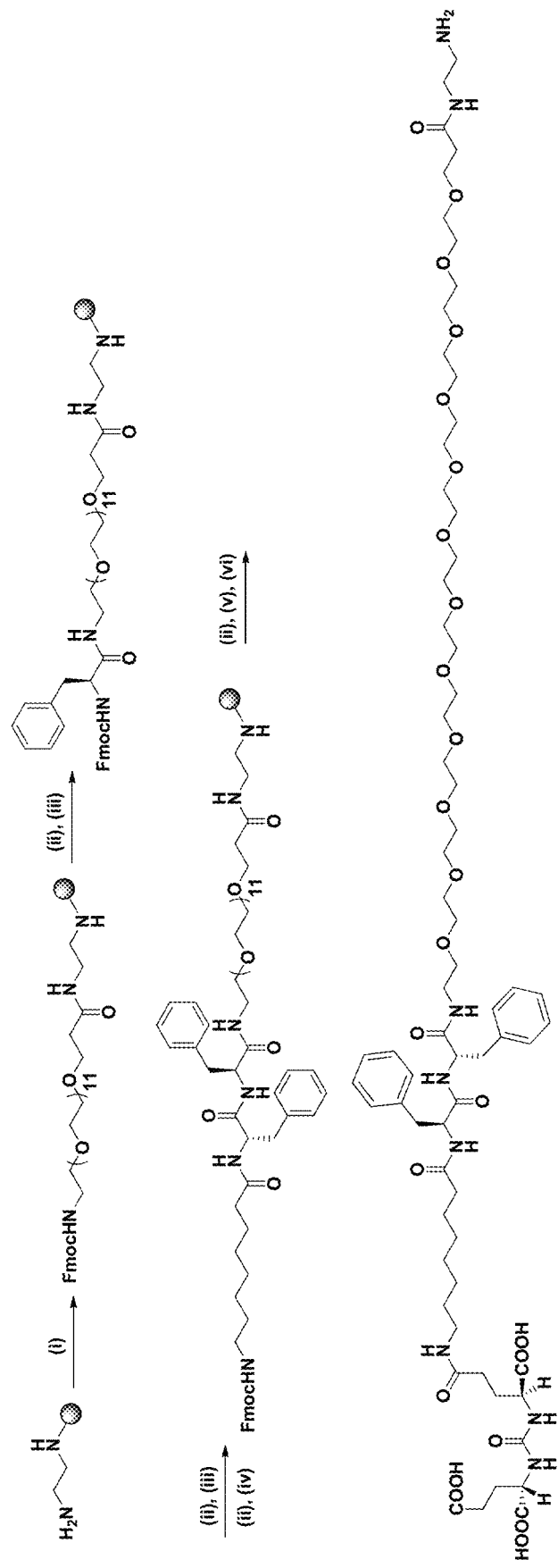
FIG. 6 shows an illustrative synthetic scheme.

Synthesis of DUPA-(PEG)$_{12}$-EDA: 1,2-Diaminoethane trityl-resin (0.025 g) was loaded into a peptide synthesis vessel and washed with i-PrOH (3×10 mL), followed by DMF (3×10 mL). To the vessel was then introduced a solution of Fmoc-NH-(PEG)$_{12}$-COOH (42.8 mg) in DMF, i-Pr$_2$NEt (2.5 equiv), and PyBOP (2.5 equiv). The resulting solution was bubbled with Ar for 1 h, the coupling solution was drained, and the resin washed with DMF (3×10 mL) and i-PrOH (3×10 mL). Kaiser tests were performed to assess reaction completion. Fmoc deprotection was carried out using 20% piperidine in DMF (3×10 mL). This procedure was repeated to complete the all coupling steps (2×1.5 equiv of Fmoc-Phe-OH and 1.5 equiv of 8-aminooctanoic acid and 1.2 equiv of DUPA were used on each of their respective coupling steps). After the DUPA coupling, the resin was washed with DMF (3×10 mL) and i-PrOH (3×10 mL) and dried under reduced pressure. The peptide was cleaved from the resin in the peptide synthesis vessel using a cleavage mixture consisting of 95% CF$_3$CO$_2$H, 2.5% H$_2$O, and 2.5% triisopropylsilane. Fifteen milliliters of the cleavage mixture was added to the peptide synthesis vessel, and the reaction was bubbled under Ar for 15 min. The resin was treated with two additional 10 mL quantities of the cleavage mixture for 5 min each. The cleavage mixture was concentrated to ca. 5 mL, and ethyl ether was added to induce precipitation. The precipitate was collected by centrifugation, washed with ethyl ether three times, and dried under high vacuum, resulting in the recovery of DUPA-(PEG)$_{12}$-EDA as crude material. FIG. 6 shows the synthetic scheme.

Figure 8:
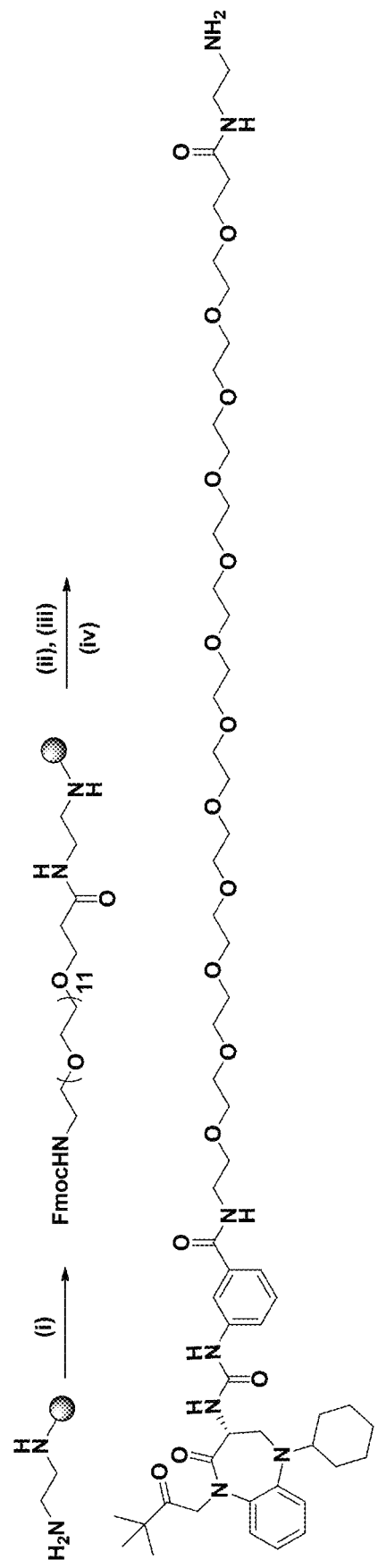
FIG. 8 shows an illustrative synthetic scheme.

Synthesis of FITC-(PEG)$_{12}$-DUPA: To a stirred solution of the crude DUPA-(PEG)$_{12}$-EDA (10 mg) and FITC (5.6 mg) in dimethylsulfoxide (DMSO, 1 mL) was added Pr$_2$NEt (5 equiv) at room temperature and stirring continued for 6 hr under argon. The reaction was monitored by LCMS and purified by preparative HPLC (mobile phase: A=10 mM ammonium acetate pH=7, B=ACN; method: 0% B to 50% B in 30 min at 13 mL/min). The pure fractions were pooled and freeze-dried, furnishing the FITC-(PEG)$_{12}$-DUPA. FIG. 8 shows the synthetic scheme.

D) Synthesis of FITC-(PEG)$_{12}$-CCK2R ligand (Z360)

Figure 7:
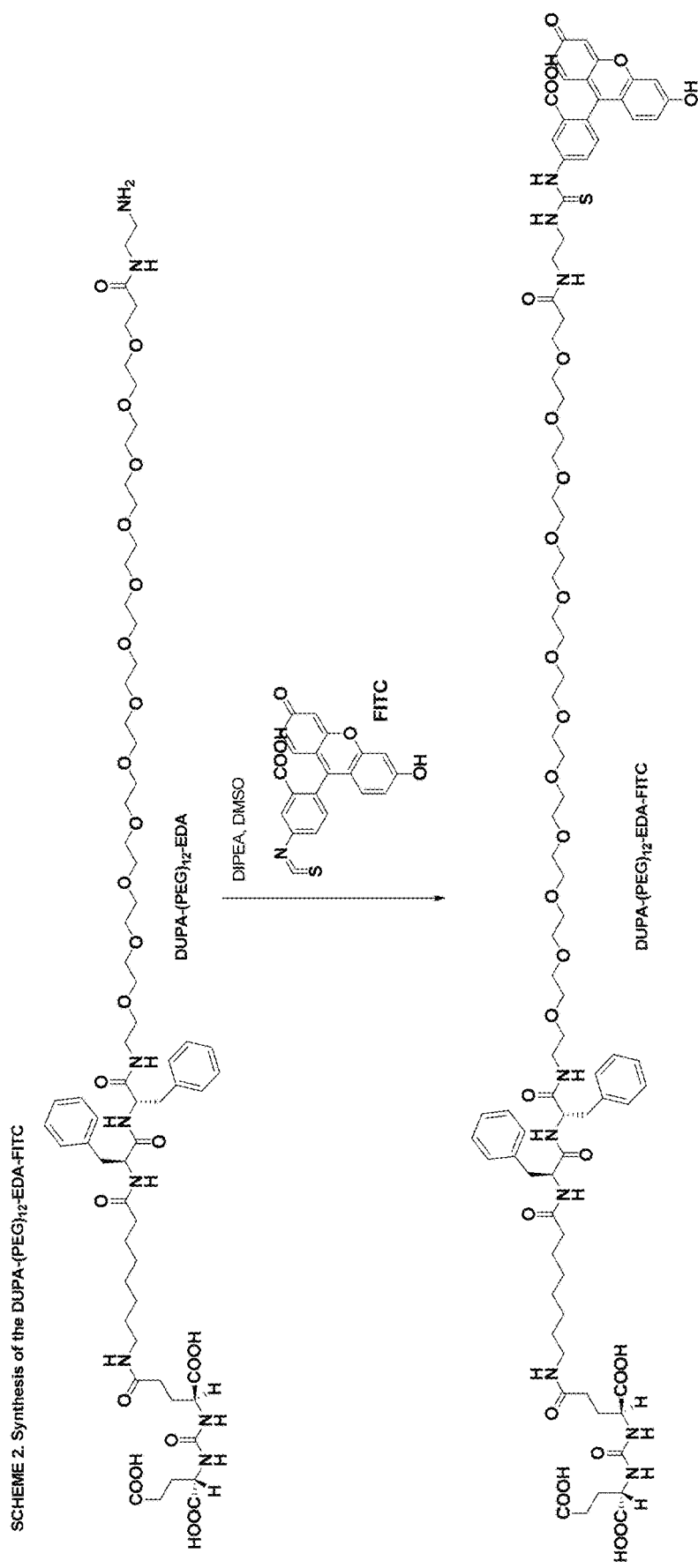
FIG. 7 shows an illustrative synthetic scheme.

Synthesis of CCK2R ligand-(PEG)$_{12}$-EDA: 1,2-Diaminoethane trityl-resin (0.025 g) was loaded into a peptide synthesis vessel and washed with i-PrOH (3×10 mL), followed by DMF (3×10 mL). To the vessel was then introduced a solution of Fmoc-NH-(PEG)$_{12}$-COOH (42.8 mg) in DMF, i-Pr$_2$NEt (2 equiv), and PyBOP (1 equiv). The resulting solution was bubbled with Ar for 1 h, the coupling solution was drained, and the resin washed with DMF (3×10 mL) and i-PrOH (3×10 mL). Kaiser tests were performed to assess reaction completion. Fmoc deprotection was carried out using 20% piperidine in DMF (3×10 mL). Then added Z360 (10 mg) in DMF, i-Pr$_2$NEt (2.5 equiv), and PyBOP (2.5 equiv). After the Z360 coupling, the resin was washed with DMF (3×10 mL) and i-PrOH (3×10 mL) and dried under reduced pressure. The peptide was cleaved from the resin in the peptide synthesis vessel using a cleavage mixture consisting of 95% $CF_3CO_2H$, 2.5% $H_2O$, and 2.5% triisopropylsilane. Fifteen milliliters of the cleavage mixture was added to the peptide synthesis vessel, and the reaction was bubbled under Ar for 15 min. The resin was treated with two additional 10 mL quantities of the cleavage mixture for 5 min each. The cleavage mixture was concentrated to ca. 5 mL, and ethyl ether was added to induce precipitation. The precipitate was collected by centrifugation, washed with ethyl ether three times, and dried under high vacuum, resulting in the recovery of crude material. FIG. 7 shows the synthetic scheme.

Figure 9:
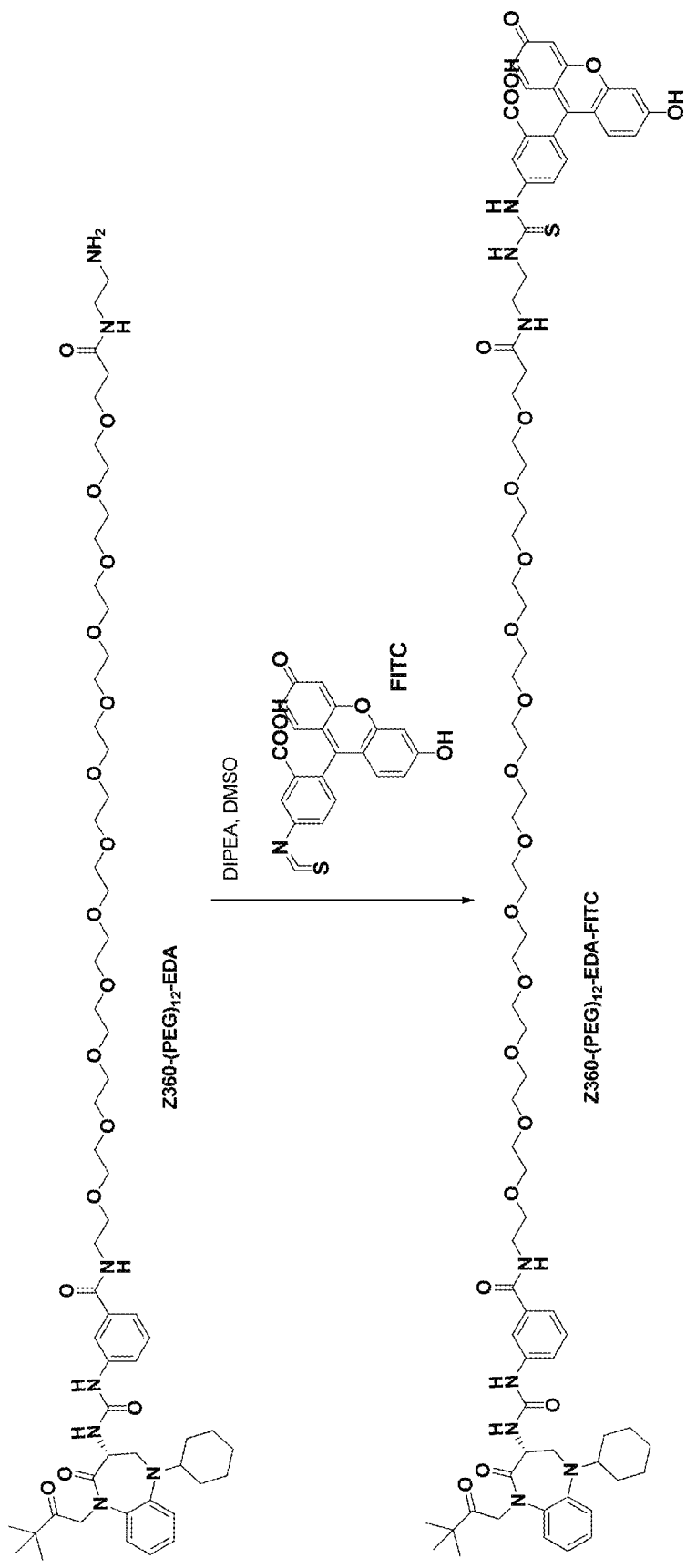
FIG. 9 shows an illustrative synthetic scheme.

Synthesis of FITC-$(PEG)_{12}$-CCK2R ligand: To a stirred solution of the crude CCK2R ligand-$(PEG)_{12}$-EDA (10 mg) and FITC (6 mg) in dimethylsulfoxide (DMSO, 1 mL) was added $Pr_2NEt$ (5 equiv) at room temperature and stirring continued for 6 hr under argon. The reaction was monitored by LCMS and purified by preparative HPLC (mobile phase: A=10 mM ammonium acetate pH=7, B=ACN; method: 0% B to 50% B in 30 min at 13 mL/min). The pure fractions were pooled and freeze-dried, furnishing the FITC-$(PEG)_{12}$-CCK2R ligand. FIG. 9 shows the synthetic scheme.

3. Binding of FITC-Folate and FITC-$(PEG)_{12}$-Folate Conjugates to Transduced T Cells Through Anti-FITC scFV in CAR4-1BBZ To examine the ability of the transduced T cells containing CAR4-1BBZ to bind the FITC-Folate conjugates, binding assays with the FITC-Folate conjugate and the FITC-$(PEG)_{12}$-Folate conjugate were performed. Since the excitation wavelength of FITC in the FITC-Folate conjugates overlapped with copGFP in CAR4-1BB transduced T cells, it was difficult to distinguish between FITC binding and copGFP expression. Therefore, an anti-Folate Acid (FA) monoclonal antibody and a fluorephore (excitation 640 nm)-labeled anti-mouse IgG antibody were utilized.

Figure 2:
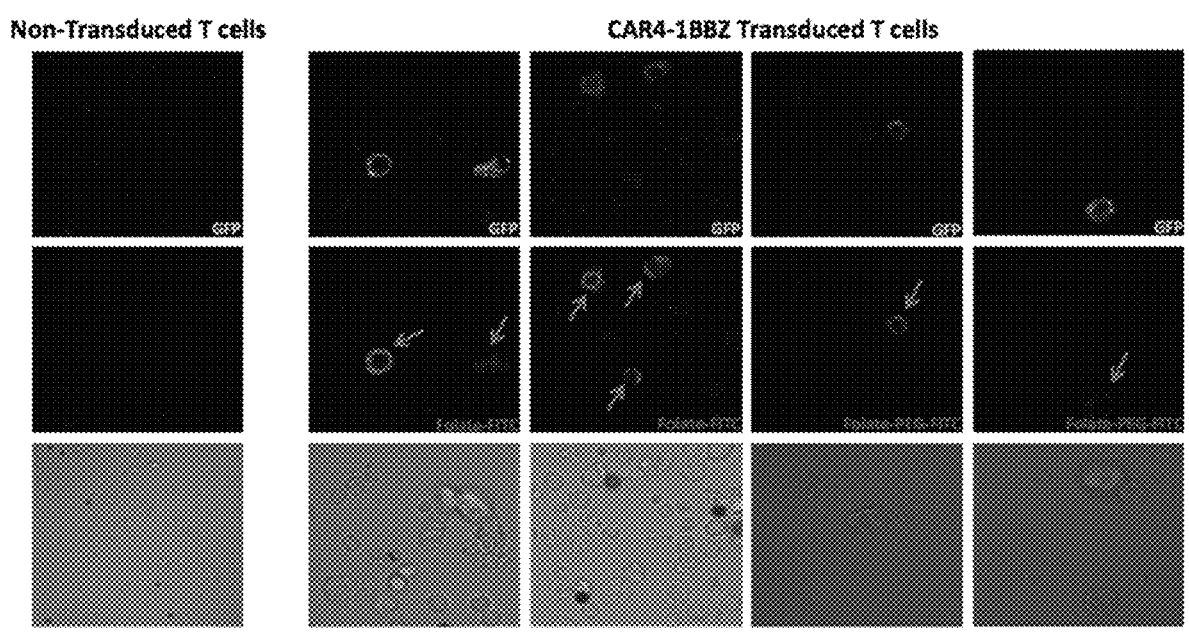
FIG. 2 shows binding of FITC-Folate and FITC-$(PEG)_{12}$-Folate conjugates to CAR-transduced T cells.

First, the transduced T cells were incubated with FITC-Folate or FITC-$(PEG)_{12}$-Folate conjugates at room temperature for 1 hour. After washing with 1×PBS, transduced T cells were incubated with anti-FA monoclonal antibody (1:15 dilution) for 1 hour. After another washing with 1×PBS, transduced T cells further were incubated with fluorophore (excitation 640 nm) labeled anti-mouse IgG antibody (1:50 dilution). Finally, unbound antibodies were washed away and a confocal microscope was used to confirm the FITC-Folate and FITC-$(PEG)_{12}$-Folate conjugates binding ability. All data was analyzed by Olympus Fluoview software. As shown in FIG. 2, copGFP expression was observed on the transduced T cells containing CAR 4-1BBZ (top row), but not in non-transduced T cells. As shown in the middle panel, FITC-folate binding was observed on CAR-1BBZ transduced T cells, but not on non-transduced T cells. More importantly, only those transduced T cells showing copGFP expression (top row) also show FITC-Folate conjugates binding (middle row). By confocal microscopy, it was confirmed that FITC-Folate and FITC-$(PEG)_{12}$-Folate conjugates were successfully bound to anti-FITC in transduced T cells, but not to non-transduced T cells. Simultaneously, binding of FITC-Folate and FITC-$(PEG)_{12}$-Folate conjugates (arrows) were also detected on the CAR4-1BBZ transduced T cells. Based on this data, it was concluded that transduced T cells express CAR4-1BBZ, and that FITC-Folate conjugates can bind to transduced T cells through anti-FITC scFv expressed by CAR4-1BBZ transduction.

4. The Binding of FITC-Folate Conjugates to FR Positive Cancer Cells

The ability of the FITC-Folate and FITC-$(PEG)_{12}$-Folate conjugates to bind folate receptor (FR) positive cancer cells was next investigated. FR positive cells lines L1210A (Mouse lymphocytic leukemia) and KB (Mouth epidermal carcinoma), which are FR positive cell lines, were used to test the binding affinity of the FITC-Folate conjugates. Briefly, $3-4×10^4$ cancer cells were prepared to perform binding affinity assays with FITC-Folate and FITC-$(PEG)_{12}$-Folate conjugates. With two different concentrations (e.g. 20 nM, 70 nM), the two FITC-Folate conjugates were incubated with cancer cells at room temperature for 1 hour. Since both FITC-Folate conjugates have fluorescence, the binding ability of FITC-Folate conjugates to cancer cells can be detected by florescence microscopy. After two washes with 1× phosphate buffered saline (PBS) to remove all unbound compound, the cancer cells were observed by confocal microscope. In order to specify whether FITC-Folate conjugates bind to cancer cells via FR on the surface of cancer cells, Folate Acid was also incubated with cancer cells as a competition compound. As shown in FIGS. 3A, 3B, 3C, and 3D, the FITC-Folate conjugates can bind to both cancer cells (KB, L1210A) via FR on the cell surface. As shown in competition panel, addition of 50× excess folate acid blocked FITC-Folate binding with these cancer cells, which indicates the specific binding is between folate acid and FR on cell surface.

Figure 3A:
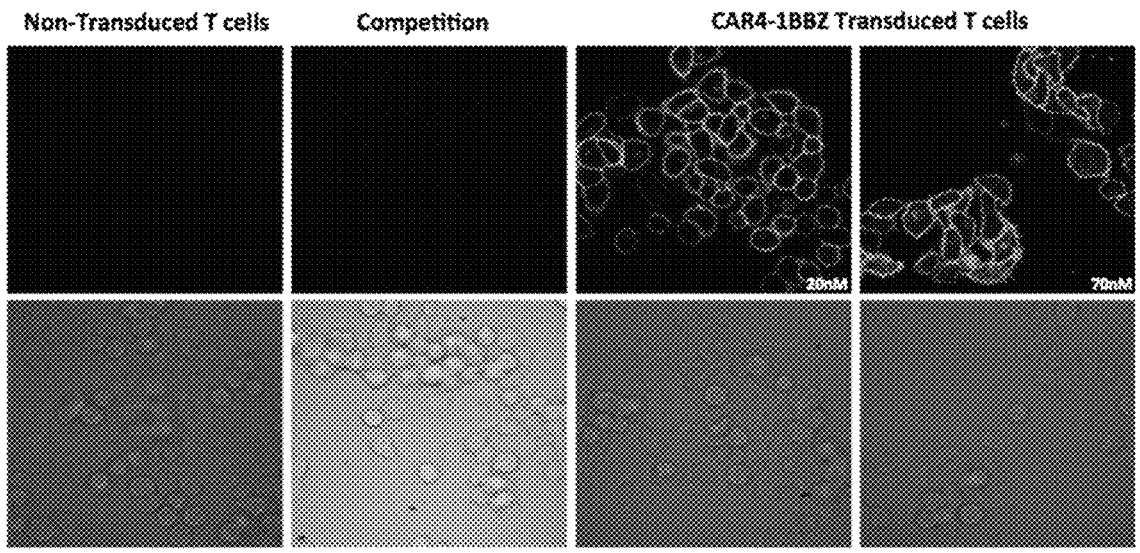
FIGS. 3A-3D show the binding ability of FITC-Folate conjugates to cancer cells via florescence microscopy.
Figure 3B:
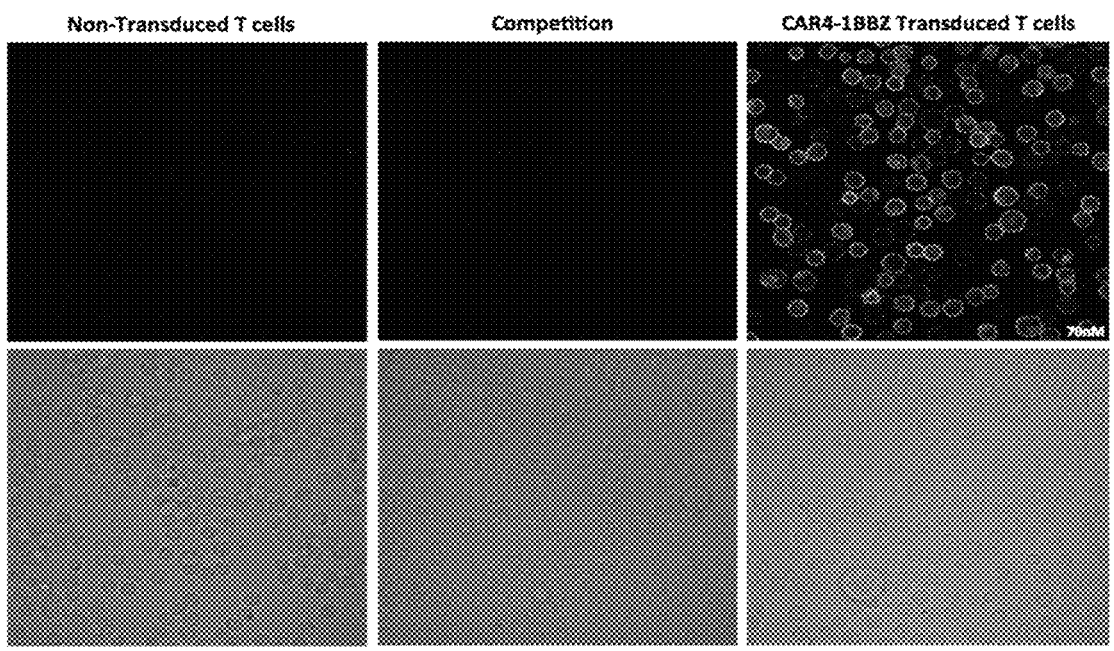
Figure 3C:
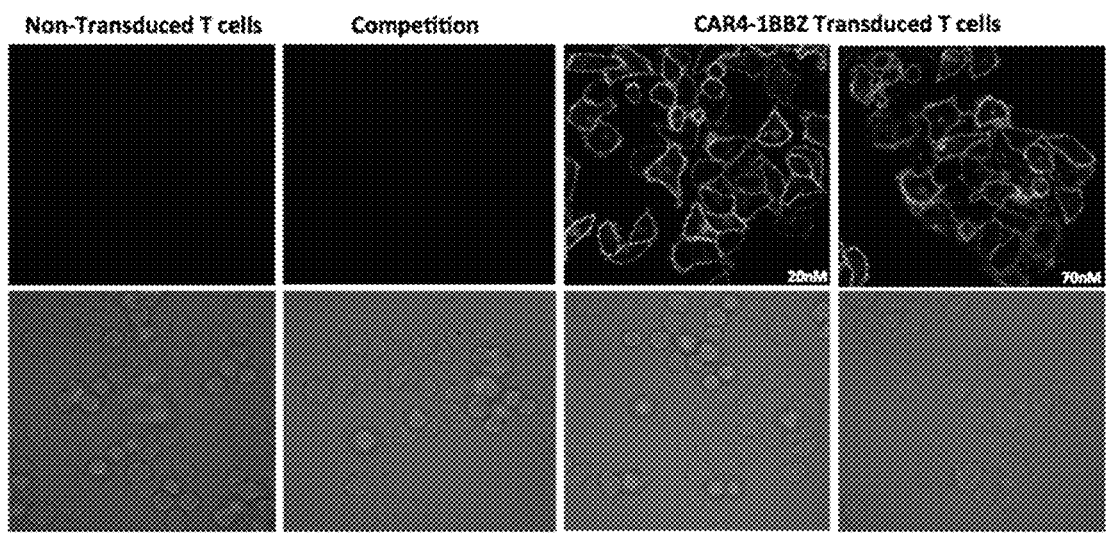
Figure 3D:
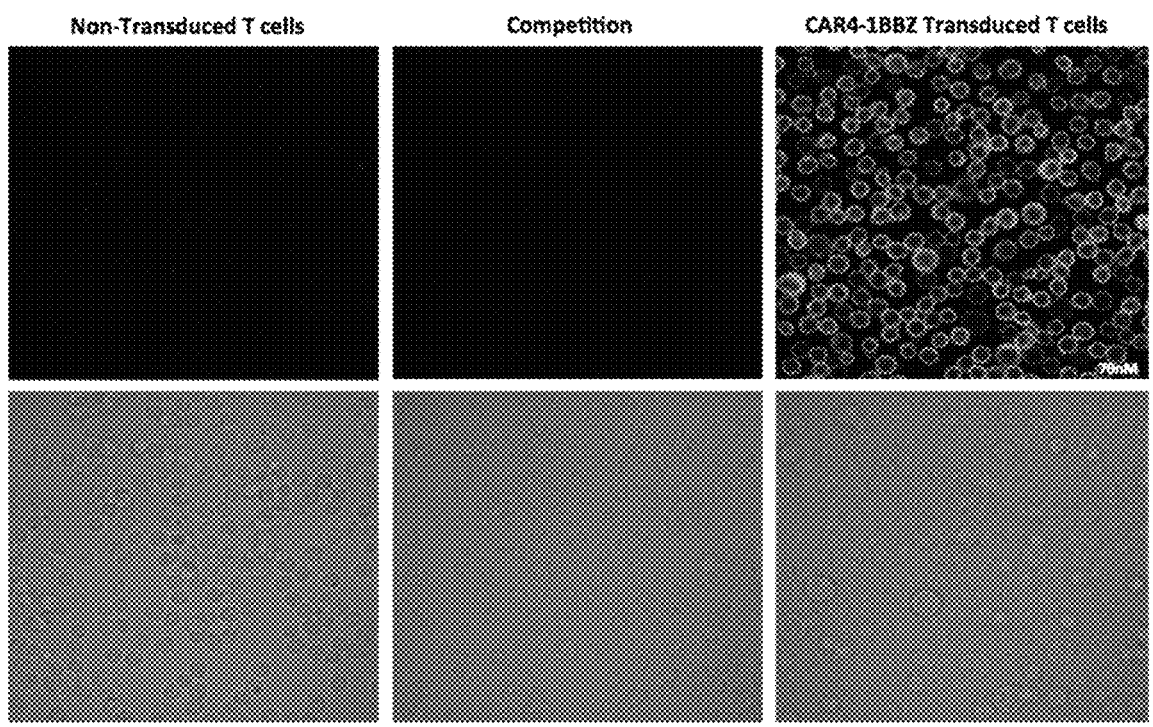

As shown in FIG. 3A, the FITC-Folate conjugate was internalized into KB cell cytoplasm, caused by FR mediated endocytosis. However, as shown in FIG. 3C, the FITC-$(PEG)_{12}$-Folate conjugate, which has a $(PEG)_{12}$ linker between Folate and FITC, stayed on the extracellular surface of the KB cells.

From this data it was concluded that the FITC-Folate and FITC-$(PEG)_{12}$-Folate conjugates can bind to cancer cells through FR on the surface of cancer cells. It was also found that the PEG linker between Folate and FITC can prohibit the internalization of FITC-Folate conjugate. Surface localization of FITC-Folate conjugate would help increase the chance for cancer cells to be recognized by transduced T cell containing CAR4-1BBZ. If FITC-Folate conjugates are internalized via FR mediated endocytosis, transduced T cells cannot target cancer cells through FITC-Folate conjugates.

5. Cytotoxicity of Anti-FITC CAR-Modified T Cells Against Folate Receptor Positive (FR+) Cancer Cells In order to explore whether CAR-expressing T cells can kill cancer cells, $^{51}$Chromium release assays were conducted. In this assay, cancer cells are labeled with $^{51}$Cr. When cancer cells are lysed, $^{51}$Cr would be released from cancer cells to supernatant. By measuring $^{51}$Cr in supernatant, the number of cancer cells killed can be determined.

First, target cancer cells L1210A were incubated in 50 μL growth medium containing 50 μCi $^{51}$Chromium to get labeled. After washing with PBS×3, L1210A cells were resuspended and incubated at 37° C. for 1 hour in the growth medium containing 70 nM FITC-Folate conjugate or FITC-$(PEG)_{12}$-Folate conjugate. After washing away excess FITC conjugates, $5×10^3$ target cancer cells were added in each well of 96-well plates. When adhesive KB cells were used as the target, they were treated similar as L1210A cells, except KB cells were grown in 96-well plates for 24 hours before $^{51}$Cr labeling and FITC-Folate conjugates binding were performed in 96-well plates. Effector T cells were then harvested, resuspended in growth media and added to the wells containing target cancer cells. The effector T cell to target cancer cell ratio was 20:1. After incubation for 4-10 hours, 20 μL aliquots of cell-free supernatant were harvested and $^{51}$Cr in the supernatants was measured with a scintillation counter or a γ-counter.

Percent specific cytolysis was calculated using following formula:

% cytolysis=(Experimental $^{51}$Cr release–control $^{51}$Cr release)/(Maximum $^{51}$Cr release–control $^{51}$Cr release)×100

Control wells contained only target cancer cells, effector T cells were never added in these wells. Maximum $^{51}$Cr release was determined by measuring $^{51}$Cr release from labeled target cells treated with 2.5% SDS to lyse all cells.

Figure 4A:
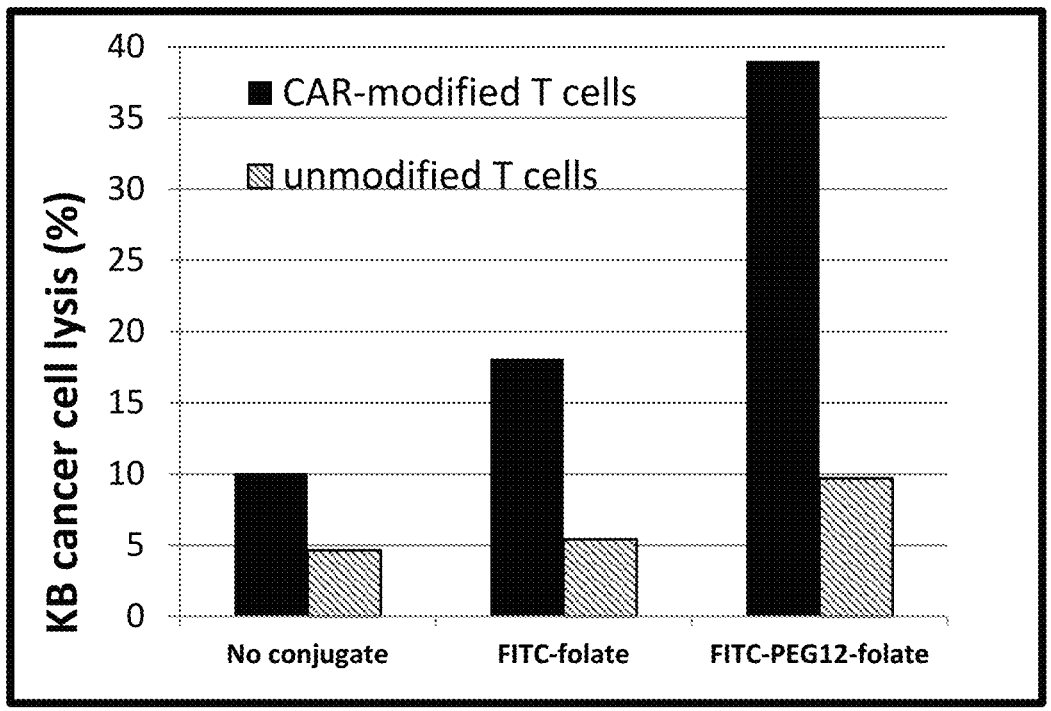
FIGS. 4A-4B show the results of assays to determine whether CAR-expressing T cells are cytotoxic to cancer cells in the presence or absence of FITC-Folate conjugates using KB cells (FIG. 4A) or L1210A cells (FIG. 4B).

As shown in FIG. 4A, in the absence of FITC-Folate conjugates, CAR-expressing T cells showed negligible activity (~5%) on target KB cell cytolysis. In the presence of FITC-Folate conjugate, CAR-expressing T cells showed ~18% cancer cell cytolysis. It is implicated that FITC-Folate conjugate acts as a bridge to redirect anti-FITC CAR-expressing T cells to FR+ KB cells. Furthermore, in the presence of FITC-(PEG)$_{12}$-Folate conjugate, which has a ~40 Å (PEG)$_{12}$ spacer between FITC and Folate molecules, anti-FITC CAR-expressing T cells showed much higher activity (~39%) on cancer cell cytolysis. With ~40 Å distance between FITC and Folate, this conjugate can redirect CAR-expressing T cells to FR+ KB cells much better (39% vs. 18%). As the non-specific cytotoxicity control, unmodified T cells showed only 5-10% cytolysis. The existence or absence of the FITC-Folate conjugates did not show any effect on unmodified T cell cytotoxicity against FR+ KB cells.

Figure 4B:
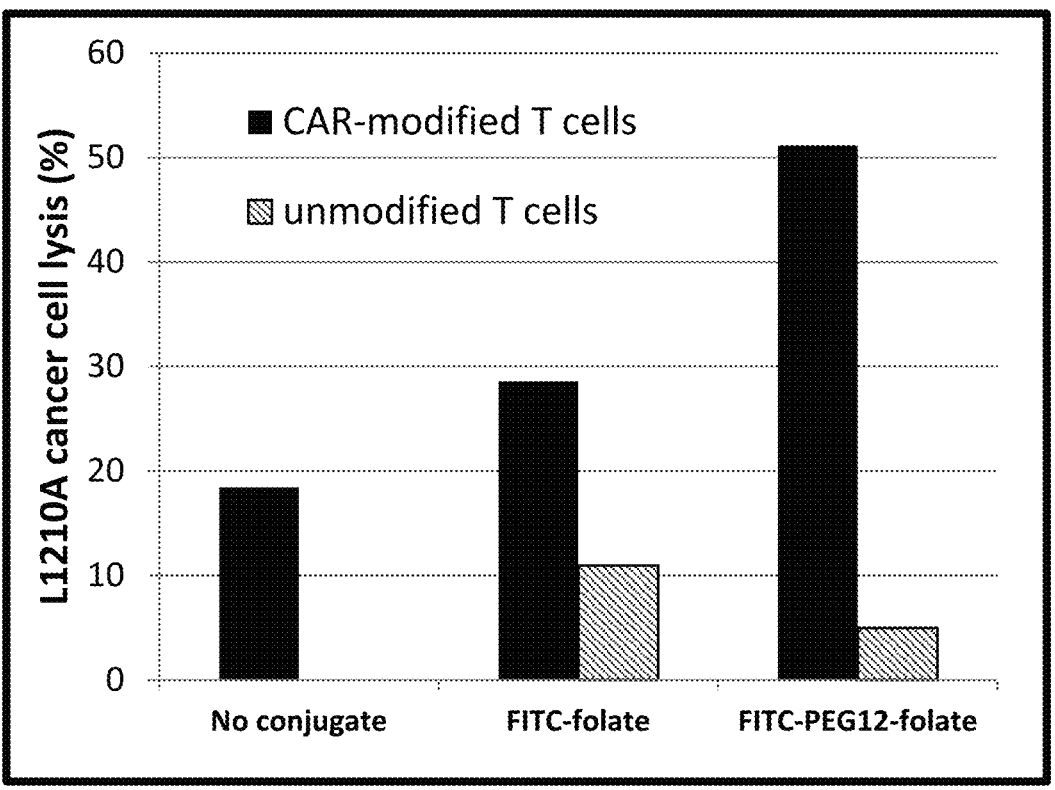

FIG. 4B shows cytotoxicity of anti-FITC CAR modified T cells against cancer cell line L1210A. In the absence of FITC-Folate conjugates, CAR-expressing T cells showed negligible activity (2-3%) on target L1210A cell cytolysis. In the presence of FITC-Folate conjugate, CAR-expressing T cells showed ~29% cancer cell cytolysis. It is implicated that FITC-Folate conjugate acts as a bridge to redirect anti-FITC CAR-expressing T cells to FR+ L1210A cells. Furthermore, in the presence of the FITC-(PEG)$_{12}$-Folate conjugate, which has a ~40 Å (PEG)$_{12}$ spacer between FITC and Folate molecules, anti-FITC CAR-expressing T cells showed much higher activity (~51%) on FR+L1210A cytolysis. With ~40 Å distance between FITC and Folate, this conjugate can redirect CAR-expressing T cells to FR+L1210A much better (51% vs. 29%). As the non-specific cytotoxicity control, unmodified T cells showed only 5-10% cytolysis as expected.

From this data it was concluded that anti-FITC CAR-expressing T cells do not have innate cytotoxicity against FR+ cancer cells. However, in the presence of the FITC-Folate conjugate, anti-FITC CAR-expressing T cells are redirected to FR+ cancer cells and cause specific cytolysis, and the activation of CAR-expressing T cells can be regulated by controlling of the addition of FITC-Folate conjugates. Further, the FITC-(PEG)$_{12}$-Folate conjugate, which has a ~40 Å spacer between the FITC and the Folate molecules, can redirect anti-FITC CAR-expressing T cells to FR+ cancer cells much better than the conjugate without the spacer.

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety. All of the following references have been cited in this application:

1. Sadelain, M. et al., The basic principles of chimeric antigen receptor design. *Cancer Discovery*. 2013. 3(4):388-98.
2. Cartellieri, M. et al., Chimeric antigen receptor-engineered T cells for immunotherapy of cancer. *J Biomedicine and Biotechnology*. 2010. Article ID 956304, 13 pages.
3. Urba, W. J. et al., Redirecting T cells. *N Engl J Med*. 2011. 365:8.
4. Porter, D. L. et al., Chimeric antigen receptor-modified T cells in chronic lymphoid leukemia. *N Engl J Med*. 2011. 365:725-33.
5. Cor, H. J. et al., Treatment of Metastatic Renal Cell Carcinoma With Autologous T-Lymphocytes Genetically Retargeted Against Carbonic Anhydrase IX: First Clinical Experience. *Clin Oncol*. 2006. 24(13):e20-2.
6. Kochenderfer, J. N. et al., B-cell depletion and remissions of malignancy along with cytokine-associated toxicity in clinical trial of anti-CD19 chimeric antigen receptor transduced T cells. *Blood*. 2012. 119(12):2790-20.
7. Reichert, J. M. Day 1, Emerging Disruptive Technologies and Cutting-Edge Analytical Techniques. *MAbs* 2009. 1(3):190-209.
8. Kularatne, S. A. et al., Prostate-specific membrane antigen targeted imaging and therapy of prostate cancer using a PSMA inhibitor as a homing ligand. *Mol Pharm*. 2009. 6(3):780-9.
9. Wayua. C. et al., Evaluation of a Cholecystokinin 2 Receptor-Targeted Near-Infrared Dye for Fluorescence-Guided Surgery of Cancer. *Molecular Pharmaceutics*. 2013. (ePublication).
10. Sega, E. I. et al., Tumor detection using folate receptor-targeted imaging agents. *Cancer Metastasis Rev*. 2008. 27(4):655-64.
11. Alvarez-Vallina, L. et al., Antigen-specific targeting of CD28-mediated T cell co-stimulation using chimeric single-chain antibody variable fragment-CD28 receptors. *Eur J Immunol*. 1996. 26(10):2304-9.
12. Imai, C. et al., Chimeric receptors with 4-1BB signaling capacity provoke potent cytotoxicity against acute lymphoblastic leukemia. *Leukemia*. 2004. 18:676-84.
13. Latza, U. et al., The human OX40 homolog: cDNA structure expression and chromosomal assignment of the ACT35 antigen. *Eur. J. Immunol*. 1994. 24:677.
14. Hutloff, A. et al., ICOS is an inducible T-cell costimulator structurally and functionally related to CD28. *Nature*. 1999. 397:263.
15. Orr, B. A., et al., Rapid Method for Measuring ScFv Thermal Stability by Yeast Surface Display. Biotechnol Prog. 2003. 19(2):631-8.
16. Kolmar, H. et al., Alternative binding proteins: biological activity and therapeutic potential of cysteine-knot miniproteins. *The FEBS Journal*. 2008. 275(11):26684-90

What is claimed is:

1. A method of killing folate receptor-positive (FR+) cancer cells, the method comprising:
   administering a fluorescein isothiocyanate-folate (FITC-folate) conjugate to a subject that has FR+ cancer cells; and
   contacting the FR+ cancer cells, the folate receptors of which are bound by fluorescein isothiocyanate-folate (FITC-folate) conjugates, with an effective amount of cytotoxic lymphocytes expressing a chimeric antigen receptor (CAR) that specifically binds FITC.

2. The method of claim 1, wherein the CAR is a fusion protein comprising a recognition region, a transmembrane domain, a co-stimulation domain, and an activation signaling domain, and wherein the recognition region of the CAR has binding specificity for FITC.

3. The method of claim 2, wherein the recognition region of the CAR is a single chain fragment variable (scFv) region of an anti-FITC antibody.

4. The method of claim 1, wherein the FITC-folate conjugates comprise a polyethylene glycol-12 ((PEG)$_{12}$) linker, and the FITC and the folate are conjugated via the linker (FITC-(PEG)$_{12}$-folate conjugates).

5. The method of claim 1, wherein the FITC-folate conjugates comprise an ethylenediamine linker, and the FITC and folate are conjugated via the linker (FITC-ethylenediamine-folate conjugates).

6. The method of claim 1, wherein a plurality of the FITC-folate conjugates are not endocytosed by the folate receptors of the FR+ cancer cells.

7. The method of claim 1, wherein induction of cytokine storm is reduced.

8. The method of claim 1, wherein the method comprises transfecting cytotoxic lymphocytes with a vector encoding the CAR that specifically binds FITC prior to contacting the FR+ cancer cells with the cytotoxic lymphocytes expressing the CAR that specifically binds FITC.

9. The method of claim 8, wherein the vector is a lentiviral vector.

10. The method of claim 1, wherein the method causes lysis of at least about 18% of the FR+ cancer cells.

11. The method of claim 1, wherein the method causes lysis of at least about 29% of the FR+ cancer cells.

12. The method of claim 1, wherein the method causes lysis of at least about 51% of the FR+ cancer cells.

13. The method of claim 1, wherein the method causes lysis of about 18% of the FR+ cancer cells.

14. The method of claim 1, wherein the method causes lysis of about 29% of the FR+ cancer cells.

15. The method of claim 1, wherein the method causes lysis of about 51% of the FR+ cancer cells.

16. The method of claim 1, wherein the cytotoxic lymphocytes are cytotoxic T lymphocytes.

17. The method of claim 16, wherein the CAR is a fusion protein comprising a recognition region, a transmembrane domain, a co-stimulation domain, and an activation signaling domain, and wherein the recognition region of the CAR has binding specificity for FITC.

18. The method of claim 17, wherein the recognition region of the CAR is a scFv region of an anti-FITC antibody.

19. The method of claim 16, wherein the FITC-folate conjugates comprise a polyethylene glycol-12 ((PEG)$_{12}$) linker, and the FITC and the folate are conjugated via the linker (FITC-(PEG)$_{12}$-folate conjugates).

20. The method of claim 16, wherein the FITC-folate conjugates comprise an ethylenediamine linker, and the FITC and the folate are conjugated via the linker (FITC-ethylenediamine-folate conjugates).

21. The method of claim 16, wherein a plurality of the FITC-folate conjugates are not endocytosed by the folate receptors of the FR+ cancer cells.

22. The method of claim 16, wherein the induction of cytokine storm is reduced.

23. The method of claim 16, wherein the method further comprises transfecting cytotoxic lymphocytes with a vector encoding the CAR that specifically binds FITC prior to contacting the FR+ cancer cells with the cytotoxic lymphocytes expressing the CAR that specifically binds FITC.

24. The method of claim 23, wherein the vector is a lentiviral vector.

25. The method of claim 16, wherein the method causes lysis of at least about 18% of the FR+ cancer cells.

26. The method of claim 16, wherein the method causes lysis of at least about 29% of the FR+ cancer cells.

27. The method of claim 16, wherein the method causes lysis of at least about 51% of the FR+ cancer cells.

28. The method of claim 16, wherein the method causes lysis of about 18% of the FR+ cancer cells.

29. The method of claim 16, wherein the method causes lysis of about 29% of the FR+ cancer cells.

30. The method of claim 16, wherein the method causes lysis of about 51% of the FR+ cancer cells.

31. A method of killing folate receptor-positive (FR+) cancer cells in a patient, which method comprises:
    administering to the patient, to whom has already been administered a fluorescein isothiocyanate-folate (FITC-folate) conjugate, an effective amount of cytotoxic lymphocytes expressing a chimeric antigen receptor (CAR) that specifically binds FITC,
    wherein the cytotoxic lymphocytes bind FITC-folate conjugate bound to folate receptors on the FR+ cancer cells in the patient.

* * * * *